US008003709B2

(12) United States Patent
Shen et al.

(10) Patent No.: US 8,003,709 B2
(45) Date of Patent: *Aug. 23, 2011

(54) CROSSLINKING OF POLYETHYLENE FOR LOW WEAR USING RADIATION AND THERMAL TREATMENTS

(75) Inventors: Fu-Wen Shen, Walnut, CA (US); Harry A. McKellop, Los Angeles, CA (US); Ronald Salovey, Rancho Palos Verdes, CA (US)

(73) Assignee: Orthopaedic Hospital, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/633,865

(22) Filed: Dec. 4, 2006

(65) Prior Publication Data

US 2007/0100017 A1    May 3, 2007

Related U.S. Application Data

(63) Continuation of application No. 10/936,149, filed on Sep. 7, 2004, which is a continuation of application No. 09/795,229, filed on Feb. 26, 2001, now Pat. No. 6,800,670, which is a continuation of application No. 09/214,586, filed as application No. PCT/US97/11947 on Jul. 8, 1997, now Pat. No. 6,228,900.

(60) Provisional application No. 60/017,852, filed on Jul. 9, 1996, provisional application No. 60/025,712, filed on Sep. 10, 1996, provisional application No. 60/044,390, filed on Apr. 29, 1997.

(51) Int. Cl.
*A61F 2/00* (2006.01)
*A61F 2/32* (2006.01)
*C08J 3/28* (2006.01)
*C08F 110/02* (2006.01)
*C08F 110/06* (2006.01)

(52) U.S. Cl. ........ 522/153; 522/154; 522/157; 522/161; 522/163; 522/164; 523/112; 523/115; 525/937; 526/351; 526/352; 623/18.11; 623/19.11; 623/19.12; 623/20.11; 623/20.14; 623/20.15; 623/20.19; 623/22.11; 623/22.15; 623/20.22; 623/22.21

(58) Field of Classification Search .................. 522/153, 522/154, 157, 161, 163, 164, 113, 115; 525/937; 526/351, 352; 529/357, 352
See application file for complete search history.

(56) References Cited

U.S. PATENT DOCUMENTS

| 2,948,668 | A |   | 11/1958 | De Whalley |
| 2,948,866 | A |   | 11/1958 | Oswald |
| 2,904,480 | A |   | 9/1959 | Rainer |
| 2,948,666 | A | * | 8/1960 | Lawton ........................ 23/313 R |
| 3,022,543 | A |   | 2/1962 | Baird, Jr. |
| 3,057,791 | A |   | 10/1962 | Anderson, Jr. |
| 3,090,770 | A |   | 5/1963 | Gregorian |
| 3,162,623 | A |   | 12/1964 | Cairns |
| 3,297,641 | A |   | 1/1967 | Werber et al. |
| 3,330,748 | A |   | 7/1967 | Lawton |
| 3,352,818 | A |   | 11/1967 | Meyer et al. |
| 3,563,869 | A |   | 2/1971 | Rainer |
| 3,616,365 | A |   | 10/1971 | Stastny |
| 3,646,155 | A |   | 2/1972 | Scott ............................ 260/827 |
| 3,671,477 | A |   | 6/1972 | Nesbitt ......................... 524/424 |
| 3,758,273 | A |   | 9/1973 | Johnston et al. |
| 3,832,827 | A |   | 9/1974 | Lemelson |
| 3,886,056 | A |   | 5/1975 | Kitamaru |
| 3,944,536 | A |   | 3/1976 | Lupton et al. |
| 3,944,538 | A |   | 3/1976 | Bodanszky |
| 4,055,662 | A |   | 10/1977 | Kurner |
| 4,055,769 | A |   | 10/1977 | Sander |
| 4,055,862 | A | * | 11/1977 | Farling ......................... 264/122 |
| 4,138,382 | A |   | 2/1979 | Polmanteer ................... 523/113 |
| 4,226,905 | A |   | 10/1980 | Harbourne |
| 4,241,463 | A |   | 12/1980 | Khovaylo |
| 4,281,420 | A | * | 8/1981 | Raab ............................. 128/898 |
| 4,336,618 | A |   | 6/1982 | Raab |
| 4,390,666 | A |   | 6/1983 | Moriguchi .................... 525/194 |
| 4,455,691 | A |   | 6/1984 | Van Aken Redinger et al. . 623/8 |
| 4,483,333 | A |   | 11/1984 | Wartman ....................... 128/90 |
| 4,518,552 | A |   | 5/1985 | Matsuo et al. ................ 264/126 |

(Continued)

FOREIGN PATENT DOCUMENTS

| BE | A-1001574 | 12/1989 |
| CA | 2297586 | 2/1997 |
| CA | 2246342 | 8/1997 |
| DE | 94 90 466 U1 | 2/1997 |
| EP | 0 169 259 | 7/1984 |
| EP | 0177552 | 4/1986 |
| EP | 0 190 889 A2 | 8/1986 |
| EP | 0218003 | 4/1987 |
| EP | 0 373 800 A1 | 6/1990 |
| EP | 0446300 | 9/1991 |

(Continued)

OTHER PUBLICATIONS

"Poly Two Carbon-Polyethylene Composite-A Carbon Fiber Reinforced Molded Ultra-High Molecular Weight Polyethylene", Technical Report, Zimmer (a Bristol-Myers Squibb Company), Warsaw (1977).

(Continued)

*Primary Examiner* — Sanza L. McClendon
(74) *Attorney, Agent, or Firm* — O'Melveny & Myers LLP

(57) ABSTRACT

The present invention discloses methods for enhancing the wear-resistance of polymers, the resulting polymers, and in vivo implants made from such polymers. One aspect of this invention presents a method whereby a polymer is irradiated, preferably with gamma radiation, then thermally treated, such as by remelting of annealing. The resulting polymeric composition preferably has its most oxidized surface layer removed. Another aspect of the invention presents a general method for optimizing the wear resistance and desirable physical and/or chemical properties of a polymer by crosslinking and thermally treating it. The resulting polymeric compositions is wear-resistant and may be fabricated into an in vivo implant.

35 Claims, 28 Drawing Sheets

U.S. PATENT DOCUMENTS

| | | | |
|---|---|---|---|
| 4,539,374 A | 9/1985 | Fenton et al. | 525/240 |
| 4,582,656 A | 4/1986 | Hoffman | |
| 4,582,856 A | 4/1986 | Lantzsch | |
| 4,586,995 A | 5/1986 | Randall | |
| 4,587,163 A | 5/1986 | Zachariades | |
| 4,655,769 A | 4/1987 | Zachariades | |
| 4,668,527 A | 5/1987 | Fujita et al. | 427/35 |
| 4,682,656 A | 7/1987 | Waters | |
| 4,701,288 A | 10/1987 | Cook | |
| 4,705,714 A | 11/1987 | Itaba | |
| 4,743,493 A | 5/1988 | Sioshansi et al. | |
| 4,747,990 A | 5/1988 | Gaussens et al. | |
| 4,813,210 A | 3/1989 | Masuda | |
| 4,816,517 A | 3/1989 | Wilkus | 524/520 |
| 4,820,466 A | 4/1989 | Zachariades | |
| 4,828,827 A | 5/1989 | Henderson et al. | 424/78.18 |
| 4,832,965 A | 5/1989 | Helin | |
| 4,876,049 A | 10/1989 | Aoyama et al. | |
| 4,888,369 A | 12/1989 | Moore, Jr. | 524/100 |
| 4,891,173 A | 1/1990 | Saitoh | |
| 4,892,552 A | 1/1990 | Ainsworth | |
| 4,902,460 A | 2/1990 | Yagi | 264/83 |
| 4,944,974 A | 7/1990 | Zachariades | |
| 4,950,151 A | 8/1990 | Zachariades | |
| 4,965,846 A | 10/1990 | Williamson, IV | |
| 5,001,008 A | 3/1991 | Tokita | |
| 5,001,206 A | 3/1991 | Bashir | |
| 5,005,053 A | 4/1991 | Kozuka | |
| 5,014,494 A | 5/1991 | George | |
| 5,017,627 A | 5/1991 | Bonfield | |
| 5,024,670 A | 6/1991 | Smith et al. | |
| 5,030,402 A | 7/1991 | Zachariades | |
| 5,037,928 A | 8/1991 | Li et al. | |
| 5,047,446 A | 9/1991 | DeNicola, Jr. | |
| 5,059,196 A | 10/1991 | Coates | |
| 5,066,755 A | 11/1991 | Lemstra | |
| 5,096,654 A | 3/1992 | Craggs | |
| 5,130,376 A | 7/1992 | Shih | 525/240 |
| 5,130,378 A | 7/1992 | Blum | |
| 5,133,757 A | 7/1992 | Sioshansi et al. | 623/18 |
| 5,137,688 A | 8/1992 | DeRudder | |
| 5,153,039 A | 10/1992 | Porter | |
| 5,160,464 A | 11/1992 | Ward et al. | |
| 5,160,472 A | 11/1992 | Zachariades | |
| 5,160,484 A | 11/1992 | Nikoloff | |
| 5,160,677 A | 11/1992 | Gravener | |
| 5,178,812 A | 1/1993 | Sanford | |
| 5,180,394 A | 1/1993 | Davidson | 623/18 |
| 5,180,484 A | 1/1993 | Frame | |
| 5,192,323 A | 3/1993 | Shetty et al. | 623/16 |
| 5,200,439 A * | 4/1993 | Asanuma | 522/157 |
| 5,210,130 A | 5/1993 | Howard | |
| 5,236,563 A | 8/1993 | Loh | 204/165 |
| 5,236,583 A | 8/1993 | Wang | |
| 5,264,214 A | 11/1993 | Rhee | |
| 5,270,118 A | 12/1993 | Sanford | |
| 5,292,584 A | 3/1994 | Howard | |
| 5,296,583 A | 3/1994 | Levy | |
| 5,334,640 A | 8/1994 | Desai et al. | 524/56 |
| 5,352,732 A | 10/1994 | Howard | |
| 5,356,998 A | 10/1994 | Hobes | |
| 5,376,122 A | 12/1994 | Pappas | |
| 5,407,623 A | 4/1995 | Zachariades et al. | |
| 5,414,049 A | 5/1995 | Sun et al. | 525/333.7 |
| 5,435,723 A | 7/1995 | O'Brien | |
| 5,439,949 A * | 8/1995 | Lucas et al. | 522/157 |
| 5,449,145 A | 9/1995 | Wortrich | |
| 5,449,745 A | 9/1995 | Sun et al. | 528/483 |
| 5,466,530 A | 11/1995 | England et al. | |
| 5,468,842 A | 11/1995 | Howard, Jr. | |
| 5,478,906 A | 12/1995 | Howard, Jr. | |
| 5,480,683 A | 1/1996 | Chabrol et al. | |
| 5,505,984 A | 4/1996 | England | |
| 5,508,079 A | 4/1996 | Grant | |
| 5,508,319 A | 4/1996 | DeNicola | 526/352 |
| 5,515,590 A | 5/1996 | Pienkowski | |
| 5,543,471 A | 8/1996 | Sun et al. | |
| 5,545,453 A | 8/1996 | Grant | |
| 5,549,698 A | 8/1996 | Averill et al. | |
| 5,549,700 A | 8/1996 | Graham et al. | |
| 5,552,104 A | 9/1996 | DeNicola, Jr. | |
| 5,577,368 A | 11/1996 | Hamilton et al. | |
| 5,593,719 A | 1/1997 | Dearnaley et al. | 427/2.26 |
| 5,609,638 A | 3/1997 | Price et al. | 623/18 |
| 5,609,643 A | 3/1997 | Colleran | |
| 5,645,882 A | 7/1997 | Llanos | 427/2.24 |
| 5,650,485 A | 7/1997 | Sun et al. | |
| 5,674,293 A | 10/1997 | Armini et al. | 623/16 |
| 5,702,448 A | 12/1997 | Buechel et al. | 623/16 |
| 5,702,456 A | 12/1997 | Pienkowski | 623/18 |
| 5,728,748 A | 3/1998 | Sun et al. | |
| 5,876,453 A | 3/1999 | Beaty | 623/16 |
| 5,879,388 A | 3/1999 | Pienkowski et al. | 623/18 |
| 5,879,400 A | 3/1999 | Merrill et al. | 623/22 |
| 5,879,407 A | 3/1999 | Waggener | 623/22 |
| 6,017,975 A * | 1/2000 | Saum et al. | 522/161 |
| 6,168,626 B1 * | 1/2001 | Hyon et al. | 623/18.11 |
| 6,228,900 B1 | 5/2001 | Shen et al. | 522/153 |
| 6,281,264 B1 | 8/2001 | Salovey et al. | 523/115 |
| 6,316,158 B1 * | 11/2001 | Saum et al. | 430/130 |
| 6,786,933 B2 * | 9/2004 | Merrill et al. | 623/23.58 |
| 6,800,670 B2 | 10/2004 | Shen et al. | 522/153 |
| 6,818,020 B2 | 11/2004 | Sun et al. | |
| 2001/0049401 A1 | 12/2001 | Salovey et al. | 523/113 |
| 2003/0045603 A1 | 3/2003 | Salovey et al. | 523/115 |
| 2003/0158287 A1 | 8/2003 | Salovey et al. | 523/115 |
| 2003/0212161 A1 | 11/2003 | McKellop et al. | 522/3 |
| 2004/0208841 A1 | 10/2004 | Salovey et al. | 424/70.11 |
| 2004/0266902 A1 | 12/2004 | Shen et al. | 522/150 |
| 2005/0048096 A1 | 3/2005 | Shen et al. | 424/423 |
| 2005/0125074 A1 * | 6/2005 | Salovey et al. | 623/23.58 |
| 2005/0267594 A1 * | 12/2005 | Merrill et al. | 623/23.58 |

FOREIGN PATENT DOCUMENTS

| | | |
|---|---|---|
| EP | 0 701 453 | 12/1994 |
| EP | 0722973 A1 | 7/1996 |
| EP | 729981 | 9/1996 |
| EP | 0729981 A1 | 9/1996 |
| EP | 0 737481 A1 | 10/1996 |
| EP | 0 881 919 | 8/1997 |
| EP | 0847765 | 6/1998 |
| EP | 1005872 | 6/2000 |
| GB | 2060469 | 5/1981 |
| GB | 2156733 | 10/1985 |
| GB | 2157298 | 10/1985 |
| GB | 2180815 | 4/1987 |
| GB | 2207436 | 2/1989 |
| GB | 2225551 | 6/1990 |
| JP | 56-133134 | 10/1981 |
| JP | 58-157830 A | 9/1983 |
| JP | A-59 168 050 | 9/1984 |
| JP | A-62 243 634 | 1/1987 |
| JP | 04-502028 | 4/1992 |
| JP | 04-198242 | 7/1992 |
| JP | A-04 185651 | 7/1992 |
| JP | 04-218504 | 8/1992 |
| JP | 09 12 22 22 | 5/1997 |
| JP | 9-12 22 22 A | 5/1997 |
| WO | 090/11060 | 10/1990 |
| WO | WO 93/10953 | 6/1993 |
| WO | WO 9427651 | 12/1994 |
| WO | WO 95/21212 | 8/1995 |
| WO | 095/34597 | 12/1995 |
| WO | WO 96/09330 | 3/1996 |
| WO | WO97/29793 | 8/1997 |
| WO | WO 98/14223 | 4/1998 |

OTHER PUBLICATIONS

Atkinson, J.R., et al., "Materials for internal prostheses: the present position and possible future developments", *Biomaterials* 1: 89-96 (1980).

Atkinson, J. R. et al., "Silane cross-linked polyethyelene for prosthetic applications. Part I. Certain physical and mechanical properties related to the nature of the material", *Biomaterials*, 4:267 (1983).

Atkinson, J. R. et al., "Silane cross-linked polyethyelene for prosthetic applications. Part II. Creep and wear behaviour and a preliminary moulding test", *Biomaterials*, 5:326 (1984).

Bartel, D. L., et al., "The Effect of Conformity, Thickness, and Material on Stresses in Ultra-High Molecular Weight Components for Total Hip Replacement", *J. Bone & Joint Surgery*, 68-A(7): 1041 (1986).

Bhateja, S.K., "Radiation-Induced Crystallinity in Pressure-Crystallized Ultrahigh Molecular Weight Polyethylene", *J. Macromol. Sci. Phys.*, B22(1): 159 (1983).

Bhateja, S.K., et a.l., "Radiation-Induced Crystallinity Changes in Linear Polyethylene", *J. Polym. Sci. Polym. Phys. Ed*, 21: 523 (1983).

Bhateja, S.K., et al., "Radiation-Induced Crystallinity Changes in Polyethylene Blends", *J. Mater. Sci.*, 20:2839 (1985).

Birkinshaw, C., et al., "The Melting Behaviour of Irradiated Polymers", *Thermochimica Acta*, 117: 365 (1987).

Bloebaum. R.D.. et al.. "Investigation of Early Surface Delamination Observed in Retrieved Heat-Pressed Tibial Inserts", *Clin. Orthop.*, 269: 120 (1991).

Bremmer, T., et al., "Peroxide Modification of Linear Low-Density Polyethylene: A Comparison of Dialkyl Peroxides", *J. Appl. Polym. Sci.*, 49: 785 (1993).

Brown, K.J., et al., "The Wear of Ultra-High Molecular Weight Polyethylene with Reference to Its Use in Prostheses", *Plastics in Medicine & Surgery Plastics & Rubber Institute*, London, 2.1 (1975).

Chen, C.J., et al., "Radiation-induced crosslinking: II. Effect on the crystalline and amorphous densities of polyethylene", *Coil, & Polym. Sci.*, 269: 469 (1991).

Chen, Y.L., et al., "Photocrosslinking of Polyethylene. I. Photoinitiators, Crosslinking Agent, and Reaction Kinetics", *J. Polym. Sci., Part A: Polym. Chem.*, 27: 4051 (1989).

Chen; Y.L., et al., "Photocrosslinking of Polyethylene. II. Properties of Photocrosslinked Polyethylene", *J. Polym. Sci., Part A: Polym. Chem.*, 27: 4077 (1989).

Connelly, G. M., et al., "Fatigue Crack Propagation Behavior of Ultrahigh Molecular Weight Polyethylene", *J. Orthop. Res.*, 2: 119 (1984).

de Boer, A. P., et al., "Polyethylene Networks Crosslinked in Solution: Preparation, Elastic Behavior, and Oriented Crystallization. I. Crosslinking in Solution", *J. Polym. Sci., Polym. Phys. Ed.*, 14: 187 (1976).

de Boer, J., et al., "Crosslinking of Ultra-High Molecular Weight Polyethylene in the Melt by Means of 2,5-dimethyl-2,5-bis(tert-butyldioxy)-3-hexyne", *Makromol. Chem., Rapid Commun.*, 2: 749 (1981).

de Boer, J., et al., "Crosslinking of Ultra-High Molecular Weight Polyethylene in the Melt by Means of 2,5-dimethyl-2,5-bis(tert-butyldioxy)-3-hexyne: 2. Crystallization Behaviour and Mechanical Properties", *Polymer*, 23: 1944 (1982).

de Boer, J., et al., "Crosslinking of Ultra-High Molecular Weight Polyethylene in the Oriented State with Dicumylperoxide", *Polymer*, 25: 513 (1984).

Dijkstra, D.J., et al., "Cross-linking of ultra-high molecular weight polyethylene in the melt by means of electron beam irradiation", *Polymer*, 30: 866 (1989).

Ding, Z. Y., et al., "Model Filled Polymers. VI. Determination of the Crosslink Density of Polymeric Beads by Swelling", *J. Polym. Sci., : Part B: Polym. Phys.*, 29: 1035 (1991).

Eyerer, P. et al., "Property changes of UHMW polyethylene hip cup endoprostheses during implantation", *J. Biomed. Materials Res.*, 18: 1137 (1984).

Eyerer, P., "Polyethylene", *Concise Encyclopedia of Medical & Dental Implant Materials*, Pergamon Press, Oxford, 271 (1990).

Ferris, B. D., "A quantitative study of the tissue reaction and its relationship to debris production from a joint implant", *J. Exp. Path.*, 71: 367 (1990).

Gielenz, G. et al., "Crystalline and supermolecular structures in linear polyethylene irradiated with fast electrons", *Colloid & Polymer Sci.*, 260: 742 (1982).

Grobbelaar, C.J. et al., "The Radiation Improvement of Polyethylene Prosthesis", *J. Bone & Joint Surgery*, 60-B(3): 370-374 (1978).

Goodman, S., et al., "Polyethylene wear in knee anthroplasty", *Acta Orthop. Scand.*, 63(3): 358 (1992).

Grood, E.S., et al., "Analysis of retrieved implants: Crystallinity changes in ultrahigh molecular weight polyethylene", *J. Biomedical Materials Res.*, 16: 399 (1982).

Huang, D.D., et al., "Cyclic Fatigue Behaviors of UHMWPE and Enhanced UHMWPE", Trans. 38th Ann. Mtg., *Orthop. Res. Soc.*, p. 403 (1992).

Kamel, I., et al., "A Model for Radiation-Induced Changes in Ultrahigh-Molecular-Weight-Polyethylene", *J. Polym. Sci. Polym. Phys. Ed.*, 23:2407 (1985).

Kampouris, E.M., et al., "Benzyl Peroxide-as a Crosslinking Agent for Polyethylene", *J. Appl. Polym. Sci.*, 34:1209 (1987).

Kao, Y.H., "Crystallinity in chemically crosslinked low density polyethylenes: 1. Structural and fusion studies", *Polymer*, 27: 1669 (1986).

Katq, K., et al., "Structural Changes and Melting Behavior of γ-Irradiated Polyethylene", *Japanese J. Appl. Phys.*, 20: 691 (1981).

Kunert, K.A., et al., "Structural Investigation of chemically crosslinked low density polyethylene", *Polymer*, 22: 1355 (1981).

Kurth, M., et al., "Effects of Radiation Sterilization on UHMW-Polyethylene", Trans. Third World Biomaterials Congress, 589 (1988).

Landy, M.M. et al., "Wear of Ultra-high-molecular-weight Polyethylene Components of 90 Retrieved Knee Prostheses", *J. Anthroplasty*, Supplement, 3: S73 (1988).

Lem, K., et al., "Rheological Properties of Polyethylenes Modified with Dicumyl Peroxide", *J. Appl. Polym. Sci.*, 27: 1367 (1982).

Li, S., et al., "Characterization and Description of an Enhanced Ultra High Molecular Weight Polyethylene for Orthopaedic Bearing Surfaces", Trans. 16th Ann. Soc. Biomaterials Meeting, Charleston, SC, 190 (1990).

Manley, T.R., et al., "The effects of varying peroxide concentration in crosslinked linear polyethylene", *Polymer*, 12:176 (1971).

McKellop, H., et al., "Friction, Lubrication and Wear of Polyethylene/Metal and Polyethylene/Ceramic Hip Prostheses on a Joint Stimulator", Fourth World Biomaterials Congress, Berlin, Apr. 118 (1992).

Minkova, L., "DSC of γ-irradiated ultra-high molecular weight polyethylene and high density polyethylene of normal molecular weight", *Colloid & Polymer Sci.*, 266:6 (1988).

Minkova, L., et al., "Blends of normal high density and ultra-high molecular weight polyethylene, γ-irradiated at a low dose", *Colloid & Polymer Sci.*, 268: 1018 (1990).

Nagy, E.V., et al., "A Fourier transform infrared technique for the evaluation of polyethylene orthopaedic bearing materials"; Trans. 16th Ann. Soc. For Biomaterials Meeting, Charleston, SC 109 (1990).

Narkis, M., et al., "Structure and Tensile Behavior of Irradiation—and Peroxide—Crosslinked Polyethylene", *J. Macromol. Sci.—Phys.*, B26 (1): 37 (1987).

Nusbaum, H. J. Et al., "The Effects of Radiation Sterilization on the Properties of Ultrahigh Molecular Weight Polyethylene", *J. Biomed. Materials Res.*, 13:557 (1979).

Oonishi, H., et al., "Improvement of Polyethylene by Irradiation in Artificial Joints", *Radiat. Phys. Chem.*, 39: 495 (1992).

Oonish, H. et al., "In Vivo and In Vitro Wear Behaviour on Weightbearing Surfaces of Polyethylene Sockets Improved by Irradiation in Total Hip Prostheses", pp. 101-115, in *Surface Modification Technologies V*, Sudarshan T.S. et al., ed. (The Institute of Materials, 1992).

Painter, P.C., et al., "The Theory of Vibrational Spectroscopy and Its Application to Polymeric Materials", John Wiley & Sons, New York, U.S.A. (1982).

Paul, J. P., "Forces Transmitted by Joints in the Human Body", *Proc. Instn. Mech. Engrs.*, 181, Part 3J, Paper 8 (1966).

Qu, B. J., et al., "Photocross-linking of Low Density Polyethylene. I. Kinetics and Reaction Parameters", *J. Appl. Polym. Sci.*, 48: 701 (1993).

Qu, B. J., et al., "Photocross-linking of Low-Density Polyethylene. II. Structure and Morphology", *J. Appl. Polym. Sci.*, 48:711 (1993).

Rimnac, C.M., et al., "Chemical and Mechanical Degradation of UHMWPE: Report of the Development of an in vitro Test", *J. Appl. Biomaterials*, 5:17 (1994).

Rimnac, C.M., et al., "Observations of Surface Damage and Degradation on Retrieved PCA Knee Implants", Trans. 38Th Ann. Orthopaedic Res. Society, Washington D.C., 330 (1992).

Rimnac, C.M., et al., "Post-Irradiation Aging of Ultra-High Molecular Weight Polyethylene", J. Bone & Joint Surgery, 76-A(7):1052 (1994).

Roe, R., et al., "Effect of radiation sterillization and aging on ultrahigh molecular weight polyethylene", J. Biomed. Mat. Res., 15:209 (1981).

Rose, R.M., et al., "On the True Wear Rate of Ultra-High-Molecular-Weight Polyethylene in the Total Hip Prosthesis", J. Bone & Joint Surgety, 62A(4): 537 (1980).

Rose, R.M., et al., "Exploratory Investigations in the Structure Dependence of the Wear Resistance of Polyethylene", Wear, 77:89 (1982).

Rostoker, W., et al., "The Appearances of Wear on Polyethylene—A Comparison of in vivo and in vitro Wear Surfaces", J. Biomed. Materials Res., 12:317 (1978).

Seedhom, B.B., et al., "Wear of Solid Phase Formed High Density Polyethylene in Relation to the Life of Artificial Hips and Knees", Wear, 24:35 (1973).

Shen, C., et al., "The Friction and Wear Behavior of Irradiated Very High Molecular Weight Polyethylene", Wear, 30:349 (1974).

Shinde, A., et al., "Irradiation of Ultrahigh-Molecular-Weight Polyethylene", J. Polym. Sci. Polym. Phys, Ed., 23:1681 (1985).

Spruiell, J. E., et al., "Methods of Experimental Physics", L. Marton & C. Marton, Eds., vol. 16, Part B, Academic Press, New York (1980).

Streicher, R.M., "Ionizing irradiation for sterillzation and modification of high molecular weight polyethylenes", Plastics & Rubber Processing & Applications, 10:221 (1988).

Streicher, R. M., "Investigation on Sterilization and Modification of High Molecular Weight Polyethylenes by Ionizing Irradiation" Beta-gamma 1/89: 34-43.

Swanson, S.A.V., et al., Chapter 3, "Friction, Lubrication and Wear", The Scientific Basis of Joint Replacement, Pittman Medical Publishing Co., Ltd. (1977).

Wang, X., et al., "Melting of Ultrahigh Molecular Weight Polyethylene", J. App. Polymer Sci., 34:593 (1987).

Wright, T.M., et al., "The effect of carbon fiber reinforcement on contact area, contact pressure, and time-dependent deformation in polyethylene tibial components", J. Biomed. Materials Res., 15:719 (1981).

Zachariades, A.E., "A New Class of UHMWPE Orthopaedic Prosthetic Devices with Enhanced Mechanical Properties", Trans. Fourth World Biomaterials Congress, Berlin 623 (1992).

Zhao, Y., et al., "Effect of Irradiation on Crystallinity and Mechanical Properties of Ultrahigh Molecular Weight Polyethylene", J. Appl. Polym. Sci., 50:1797 (1993).

News You Can Use, vol. II, No. 2 (May 1996).

"For the Tough Jobs: 1900 UHMW Polymer", Himont Inc.(1988).

"Abrasion-Resistant 1900 UHMW Polymer", Hercules Inc. (1979).

"Technical Information: 1900 Ultrahigh Molecular Weight Polymer, General Information and Applications", Bulletin HPE-101A, Hercules U.S.A., Inc. (1989).

"Technical Information: 1900 Ultrahigh Molecular Weight Polymer, Nuclear Radiation Effects", Bulletin HPE-111, Himont U.S.A. Inc. (1985).

"Technical Information: 1900 Ultrahigh Molecular Weight Polymer, Effect of Polymer Modification", Bulletin HPE-116, Himont U.S.A.. Inc. (1987).

Appleby, R.W., et al., "Post-gamma irradiation cross-linking of polyethylene tape by acetylene treatment", J. Material Sci. 29: 227-231 (1994).

Higgins, J.C., et al., "Evaluation of Free Radical Reduction Treatments for UHMWPE", Prodeedings of the 42nd Annual Mtg, Orthopaedic Res. Soc., Feb. 19-22, at p. 485 (1996).

Jasty, M., et al, "Marked Improvement in the Wear Resistance of a New Form of UHMWPE in Physiologic Hip Simulator", Trans. 43rd Ann. Mtg, Orthopaedic Research Soc., Feb. 9-13, 1997, San Francisco, CA, p. 785.

Jasty, M. et al., "Marked Improvement in the Wear Resistance of a New Form of UHMWPE in a Physiologic Hip Simulator", Trans. Soc. Biomaterials, vol. XX, p. 71, 23rd Ann. Meeting Soc. for Biomaterials, Apr. 30-May 4, 1997, New Orleans, Lousiana, U.S.A., p. 157.

Streicher, "Influence of Ionizing Irradiation in Air and Nitrogen for Sterilization of Surgical Grade Polyethylene for Implants", Radiat. Phys. Chem., vol. 31, Nos. 4-6, pp. 693-698 (1988).

Roe et al., "Effect of Radiation Sterilization and Aging on Ultrahigh Molecular Weight Polyethylene", J. Biomed. Materials Res., 15: 209-230 (1981).

Pleiss et al., "The Improvement of Polyethylene Prostheses Through Radiation Crosslinking", Radiat. Phys. Chem., 9:647-652 (1977).

Streicher, "The Behavior of UHMW-PE when Subjected to Sterilization by Ionizing Radiation", Ultra-High Molecular Weight Polyethylene as Biomaterial in Orthopedic Surgery, pp. 66-73 (1990).

Saunders, C. et al., "Radiation Effects on Microorganisms and Polymers for Medical Products," Medical Device & Diagnostic Industry, pp. 89-92, 222 (1993).

Kang et al., "The Radiation Chemistry of Polyethylene. IX. Temperature Coefficient of Cross-Linking and Other Effects", J. Amer Chem Society 89 (9): 1980-1986 (1967).

Rose et al., "Radiation Sterilization and the Wear Rate of Polyethylene", J. Orthopaedic Res. Society, 2(4): 393-400 (1984).

Oonishi, H. et al., Super Low Wear Cross-Linked UHMWPE by Heavy High-Dose Gamma Radiation, WPOA 2nd Congress of Hip Section, p. 61, 1996.

Jahan et al., "Combined chemical and mechanical effects on free radicals in UHMWPE joints during implantation", J. Biomed Material Res., 25: 1005-1016 (1991).

Standard Practice for Dosimetry in an Electron Beam Facility for Radiation Processing at Energies Between 300 keV and 25 keV, Am Soc for Testing & Materials, Designation: E1649-94, 870-888 (1995).

Oonishi, H. et al., "Improvement Of Polyethylene by Irradiation in Artificial Joints", Radia Phys Chem, 39(6): 495-504 (1992).

Oonishi, H. et al., "The Low Wear of Cross-Linked Polyethylene Socket in Total Hip Prosthees", Encyclopedic Handbook of Biomaterials & Bioengineering, vol. 2, Marcel Dekker, Inc., 1853-1868 (1995).

Atkinson, J., et al., "The nature of silane cross-linked HDPE is discussed. Creep and wear tests indicate its potential as a possible replacement for high molecular weight polyethylene in prostheses", Polymers in Medicine and Surgery, Conf. held by Plastics and Rubber Institute and Biologidal Engineering Soc., UK, Sep. 1986, P4/1-P4/9.

Jones, W., et al., "Effect of γ Irradiation on the Friction and Wear of Ultrahigh Molecular Weight Polyethylene", Wear 70: 77-92 (1981).

Gent, A., et al., "Elastic Behavior, Birefringence, and Swelling of Amorphous Polyethylene Networks", J. Polymer Sci 5: 47-60 (1967).

Zoepfl, F., et al., "Differential Scanning Calorimetry Studies of Irradiated Polyethylene: I. Melting Temperatures and Fusion Endotherms", J. Polymer Sci Polym. Chem. Ed. 22: 2017-2032 (1984).

Zoepfl, F., et al., Differential Scanning Calorimetry Studies of Irradiated Polyethylene: II. The Effect of Oxygen, J. Polymer Sci Polym. Chem. Ed. 22: 2032-2045 (1984).

Mandelkern, L., et al., Fusion of Polymer Networks Formed from Linear Polyethylene: Effect of Intermolecular Order: contribution from the General Electric Research Laboratory and from the Polymer Structure Section, National Bureau of Standards 82: 46-53 (1960).

Matsubara, K., et al., "The Wear Properties of High-Density Polyethylene Irradiated by Gamma Rays", Wear, 10: 214 (1967).

McKellop, H., et al., "Increased Wear of UHMW Polyethylene After Gamma Radiation Sterilization", Trans. 26th Ann. ORS, Atlanta, Georgia, Feb. 5-7 (1980).

McKellop, H., "The Effect of Radiation and Ethylene Oxide Sterilization on the Wear of UHMW Polyethylene," 7th European Conference on Biomaterials, Sep. 8-11, 1987.

Shen, F-S., et al., "Irraidation of Chemically Crosslinked Ultrahigh Molecular Weight Polyethylene", J. Polymer Sci.: Part B: Polymer Phys., 34: 1063-1077 (1996).

Oka M., et al., "Wear-Resistant Properties of Newly Improved UHMWPE", Trans. Fifth World Biomaerials Congress, May 29-Jun. 2, 1996, Toronto, Canada, p. 520.
Bellare, A., et al., "Deformation, Morphology and Wear Behavior of Polyethylene", Trans. 23rd Ann. Mtg., Soc. Biomaterials, Apr. 30-May 4, 1997, New Orleans, Lousiana, p. 75.
Clarke, I.C., et al., "Simulator Wear Study of High-Dose Gamma-Irradiated UHMWPE Cups", Trans. 23Rd Ann. Mtg., Soc. Biomaterials, Apr. 30-May 4, 1997, New Orleans, LA, p. 71.
Taylor, G., et al., "Stability of $N_2$ Packaged Gamma Irradiated UHMWPE", Trans. 23rd Ann. Mtg., Soc. Biomaterials, Apr. 30-May 4, 1997, New Orleans, LA, p. 421.
Taylor, G., et al., "Stability of $N_2$ Packaged Gamma Irradiated UHMWPE", Trans. 43rd Ann. Mtg., Orthopaedic Res. Soc., Feb. 9-13, 1997, San Francisco, California, p. 776.
Muratoglu, O.K., et al., "Electron Beam Cross-Linking of UHMWPE at Room Temperature, A Candidate Bearing Material for Total Joint Arthoplasty," Trans. 23rd Ann. Mtg., Soc. Biomaterials, Apr. 30-May 4, 1997, New Orleans, LA, p. 74.
McKellop, H. et al., "The Effect of Sterilization Method, Calcium Stearate and Molecular Weight on Wear of UHMWPE Acetabular Cups", Trans. 23rd Ann. Mtg., Soc. Biomaterials, Apr. 30-May 4, 1997, New Orleans, LA, p. 43.
McKellop, H. et al., "Effect of Sterilization Method on the Wear Rate of UHMW Polyethylene Acetabular Cups in a Hip Simulator", Trans. 43rd Ann.Mtg., Orthopaedic Res. Soc., Feb. 9-13, 1997, San Francisco, California, p. 94-16.
McKellop, H. et al., "Effect of Sterilization Method and Other Modifications on the Wear Resistance of UHMWPE Acetabular Cups", Hand-Out for Polyethylene Wear in Orthopaedic Implants Workshop, Trans. 23rd Ann. Mtg., Soc. Biomaterials, Apr. 30-May 4, 1997, New Orleans, LA.
McKellop, H. et al., "Wear of UHMWPE Acetabular Cups After Gamma Sterilization in Nitrogen, Thermal Stabilization and Artificial Aging", Trans. 23rd Ann. Mtg., Soc. Biomaterials, Apr. 30-May 4, 1997, New Orleans, LA, p. 45.
Wang, A., et al., "Effect of Raidation Dosage on the Wear of Stabilized UHMWPE Evaluated by Hip and Knee Joint Simulators", Trans. 23rd Ann. Mtg., Soc. Biomaterials, Apr. 30-May 4, 1997, New Orleans, LA, p. 394.
Wang, A., et al., "Wear Mechanisms and Wear Testing of Ultra-High Molecular Weight Polyethylene in Total Joint Replacements", Hand-Out for Polyethylene Wear in Orthopaedic Implants Workshop, Trans. 23rd Ann. Mtg., Soc. Biomaterials, Apr. 30-May 4, 1997, New Orleans, LA.
Yu, YJ., et al., "Oxidation of UHMWPE Acetabular Cups After Sterilization and Wear Testing in a Hip Joint Simulator", Trans. 43rd Ann. Mtg., Orthopaedic Res. Soc., Feb. 9-13, 1997, San Francisco, California, LA, p. 778.
Nov. 16, 2007 "Communication of a Notice of Opposition" from the European Patent Office regarding European Patent No. 0935446.
D5a: Table concerning Table 1 of D5 comprising further additional figures.
D6a: J. de Boer, "Crosslinking of high molecular weight polyethylene," Rijksuniversiteit Te Groningen, Proefschrift et al., Vrijdag, Mar. 23, 1984.
D6b: Table concering Table 1 of D6 comprising further additional figures.
D12: D.J. Dijkstra, "Entanglements and Cross-links in Utlra-High Molecular Weight Polyethylene", Rijksuniversiteit Groningen-Proefschrift et al., Vrijdag Sep. 9, 1988.
D15: ASTM D 2765-01, "Standard Test Methods for Determination of Gel Content and Swell Ratio of Crosslinked Ethylene Plastics", ASTM International, PA, USA.
D16: Y. Dirix, H. Schmotzer, Technical Report, "Crosslinking of UHMWPE after Grobbelaar or Sun: Characterization of the physical properties", Project No: 08182, Nov. 5, 2007.
D17: Test Report PU 339 vom 15.10.2007, "Determination of gel content, swelling degree and network chain density of crosslinked UHMWPE samples", University of Stuttgart, Department of Plastic Technology.
Mar. 7, 2006 Canadian Intellectual Property Office's "Requisition" of Canadian Patent Application No. 2,260,241.

Dec. 18, 2006 Canadian Intellectual Property Office's "Requisition" of Canadian Patent Application No. 2,260,241.
Jul. 23, 2009 Canadian Intellectual Property Office's "Requisition" of Canadian Patent Application No. 2,260,241.
Jul. 3, 2009 Communication from the European Patent Office's. Opposition Division, regarding European Patent No. 0935446, enclosing Submission of the Opponent dated Jun. 25, 2009.
Oonishi, H., et al., New Medical Technology Development Research Project-Government-Private Sector Joint Research Project-Research Report 1994, pp. 204-213 (Publication date: Sep. 20, 1995)—Japanese language reference and its English translation.
Oonishi, H., et al., New Medical Technology Development Research Project-Government-Private Sector Joint Research Project-Research Report 1995, pp. 161-170 (Publication date: Sep. 5, 1996)—Japanese language reference and its English translation.
Oonishi, H., et al., "Prosthetic hip joint with improved wear resistance", Orthopaedic Surgery: Separate Volume, vol. 18, pp. 216-221 (Publication Date: Oct. 1, 1990)—Japanese language reference and its. English translation.
Akana, Y. and Stein, R.S., "Optical Studies Of The Crystallization Of Trans 1,4-Polybutadiene In Stretched Networks," Journal of Polymer Science: Polymer Physics Edition 13:2195-2219 (1975).
Alexander, Leroy E. X-ray Diffraction Methods in Polymer Science. New York: Wiley-Interscience, xi-xv (1969).
Allen, G., and J. C. Bevington. "Etching and Microstructure of Crystalline Polymers." Comprehensive Polymer Science: the Synthesis, Characterization, Reactions & Applications of Polymers. Oxford, England: Pergamon, 841-66 (1989).
Allen, G., and J. C. Bevington. Comprehensive Polymer Science: the Synthesis, Characterization, Reactions & Applications of Polymers. First ed. vol. 1. Oxford, England: Pergamon, v-vii (1989).
Amstutz, et al, "Mechanism And Clinical Significance Of Wear Debris-Induced Osteolysis," Clinical Orthopaedics and Related Research, 276: 7-18 (Mar. 1992).
Andreopoulos, A.G., and Kampouris, E.M., "Mechanical Properties of Crosslinked Polyethylene", Journal of Applied Polymer Science 31:1061-1068 (1986).
Andrews, E. H. Fracture in Polymers. New York: American Elsevier, xi-xiii (1968).
Andrews, E.H., "The Influence of Morphology on the Mechanical Properties of Crystalline Polymers", Pure Appl. Chem. 31:91-111 (1972).
Arnell, R. D. Tribology Principles and Design Applications. Reprinted ed. Houndmills, AU: Macmillan Education, v (1993).
Atkinson, J.R. et al., "The Wear of High Molecular Weight Polyethylene: Part I: The Wear of Isotropic Polyethylene Against Dry Stainless Steel in Unidirectional Motion," Journal of Lubrication Technology 100: 208-218 (Apr. 1978).
Author Unknown, "A Comparative Analysis of the Properties of Standard and 'Enhanced' Ultra-High Molecular Weight Polyethylene, Facts on UHMWPE. Part Three of a Series on Ultra-High Molecular Weight Polyethylene," Howmedica Inc., Rutherford, NJ, p. 1-12 (1994).
Author Unknown, "Overview and Fundamentals of UHMWPE: Facts on UHMWPE. Part One of a Series on Ultra-High Molecular Weight Polyethylene," Howmedica Inc., Rutherford, NJ, p. 1-8 (1994).
Author Unknown, "Particulate Debris in Total Hip Arthroplasty," American Academy of Orthopaedic Surgeons 1993 Annual Meeting—Scientific Program (1993).
Author Unknown, "Standard Test Methods For Determination Of Gel Content And Swell Ratio Of Crosslinked Ethylene Plastics," American Society for Testing and Materials, Designation D2765-01(1984).
Author Unknown, "What Are the Most Productive Directions For Future Research?" NIH Consensus Statement, Total Hip Replacement, National Institutes of Health, 12(5):22 (Sep. 12-14, 1994).
Author Unknown, Material Properties, Product Quality Control, and Their Relation to UHMWPE Performance. Facts on UHMWPE. Part Two of a Series on ultra-High Molecular Weight Polyethylene (Howmedica Inc., Rutherford, NJ (1994).
Bair, H.E., and Salovey, R., "The Melting Behavior of the Form III of Polybutene-1 Single Crystals," Journal of Polymer Science Part B: Polymer Letters, 5(5): 429-432 (May 1967).

Bakker, M., and David Eckroth. The Wiley Encyclopedia of Packaging Technology. New York: J. Wiley, 530, 562, 564(1986).
Baltá-Calleja, F. J., and C. G. Vonk. X-ray Scattering of Synthetic Polymers, Table of Contents, Amsterdam: Elsevier (1989).
Barton J., "Peroxide Crosslinking of Poly (*n-alkyl* Methacrylates)," Journal of Polymer Science: Part A-1, 6: 1315-1323 (1968).
Bassett, "On the Morphology of Melt-Crystallized Polyethylene. III. Spherulitic Organization," Proceedings of the Royal Society of London. Series A, Mathematical and Sciences, 377(1768):61-71 (Jun. 5, 1981).
Bassett, D. C. Principles of Polymer Morphology. Cambridge Eng.: Cambridge University Press, Table of Contents, (1981).
Bassett, D.C. and Hodge, A.M., "On Lamellar Org In Certain Polyethylene Spherulites," Proceedings of the Royal Society of London. Series A, Mathematical and Physical Sciences, 359(1696):121-132 (Jan. 31, 1978).
Bassett, D.C. and Hodge, A.M., "On the Morphology of Melt-Crystallized Polyethylene I. Lamellar Profile," Proceedings of the Royal Society of London. Series A, Mathematical and Physical Sciences, 377(1768):25-37 (Jun. 5, 1981).
Bassett, D.C. et al., "On the Morphology of Melt-Crystallized Polyethylene II. Lamellae and their Crystallization Conditions," Proceedings of the Royal Society of London. Series A, Mathematical and Physical Sciences, 377(1768):39-60 (Jun. 5, 1981).
Bhateja, S. et al., "Impact-Fatigue Response of Ultrahigh Molecular Weight Linear Polyethylene. 3. Morphological Effects," Ind. Eng. Chem. Prod. Res. Dev. 19(4):607-612 (1980).
Bhateja, S.K. and Andrews, E.H., "Effect of high-energy radiation on the uniaxial tensile creep behaviour of ultra-high molecular weight linear polyethylene," Polymer 24:160-166 (1983).
Bhateja, S.K. and Andrews, E.H.,"Effect of High Energy Radiation on the Stress-Relaxation of Ultra-High Molecular Weight Linear Polyethylene," Journal of Applied Polymer Science 34:2809-2817 (1987).
Bhateja, S.K. et al., "Impact fatigue response of ultrahigh molecular weight linear polyethylene," Journal Material Science 14:2103-2109 (1979).
Bhateja, S.K. et al., "Radiation Induced Crystallinity Polyethylenes: Long Term Aging Effects," Polymer Journal 21(9): 739-750 (1989).
Bhateja, S.K. et al., "Radiation-Induced Crystallinity Polyethylene: Long-Term Aging Effects in Pressure-Crystallized Ultra-High Molecular Weight Polymer," Journal of Macromolecular Science-Physics, B29(1):1-10 (1990).
Bhateja, S.K., "Changes in the crystalline content of irradiated linear polyethylenes upon ageing," Polymer 23:654-655 (1982).
Bhateja, S.K., "Radiation-Induced Crystallinity Changes in Linear Polyethylene: Influence of Aging," Journal of Applied Polymer Science 28:861-872 (1983).
Bhateja, S.K., "Uniaxial tensile creep behaviour of ultra high molecular eight linear polyethylene," Polymer 22: 23-28 (1981).
Billmeyer, F.W. , "Rheology and the Mechanical Properties of Polymers," Textbook of Polymer Science. New York: Wiley, 312-15 (1984).
Birkinshaw, C. et al., "Mechanism of Ageing in Irradiated Polymers," Polymer Degradation and Stability 22:285-294 (1988).
Birkinshaw, C. et al., "The Effect of Sterilising Radiation on the Properties of Ultra-High Molecular Weight Polyethylene," Materials Chemistry and Physics 14:549-558 (1986).
Birkinshaw, C. et al., "The Effect of γ Radiation on the Physical Structure and Mechanical Properties of Ultrahigh Molecular Weight Polyethylene," Jciumal of Applied Polymer Science 38:1967-1973 (1989).
Black, J. et al., "Metallosis Associated With A Stable Titanium-Alloy Femoral Component In Total Hip Replacement. A Case Report", The Journal of Bone and Joint Surgery, Incorporated 72-A(1):126-130 (1990).
Black, J., "Other Mechanical Properties," Orthopaedic Biomaterials in Research and Practice. New York: Churchill Livingstone, 144-50 (1988).
Blackadder, D. A. And Lewell, P.A., "Properties Of Polymer Crystal Aggregates. (2) Annealing Of Polyethylene Crystal Aggregates," Polymer 11(2):147-164 (1970).

Blackadder, D.A. et al., "Annealing of high density polyethylene for very long times at low supercooling under vacuum," Polymer 13:584-586 (Dec. 1972).
Blunn, G.W. And Bell, C.J., "The Effect of Oxidation on the Wear of Untreated and Stabilised UHMWPE," 42nd Annual Meeting, Orthopaedic Research Society, Atlanta, Georgia, p. 482 (Feb. 19-22, 1996).
Blunn, G.W. et al., "A Retrieval and In Vitro Study of Degradation of Ultra-High Molecular Weight Polyethylene In Total Knee Replacements," Fourth World Biomaterials Congress, Berlin, Germany, p. 276 (Apr. 24-28,1992).
Boggan, R.S. et al., "The Effect of Radiation Sterilization on the Physical and Mechanical Properties of UHMWPE," 19th Annual Meeting of the Society for Biomaterials, Birmingham, AL, p. 329 (Apr. 28 - May 2, 1993).
Booth, A.F., "Industrial Sterilization Technologies: New and Old Trends Shape Manufacturer Choices," Medical Device & Diagnostic Industry, pp. 64-72 (Feb. 1995).
Brandrup, J., and E. H. Immergut. "Physical Constants of Poly(ethylene)," Polymer Handbook. New York: Wiley, V-17 (1989).
Bremner, T. and Rudin, A. ,"Effects of Polyethylene Molecular Structure on Peroxide Crosslinking of Low Density Polyethylene," Polymer Engineering and Science 32(14):939-943 (Jul. 1992).
Broza, et al., "Epitaxial Crystallization of Polyethylene and Paraffin on Oriented Polypropylene," Journal of Polymer Science: Polymer Physics Edition 23:2623-2627 (1985).
Calcagno, L. and Foti, G., "Density Enhancement In Ion Implanted Polymers," Nuclear instruments & Methods in Phys. Res. B19/20:895-898 (1987).
Campbell, P. et al., "Automated particle sizing following digestion of periprosthetic tissues: What are we measuring?" 19th Annual Meeting Society for Biomaterials, Birmingham, AL, p. 241 (Apr. 28 - May 2, 1993).
Campbell, P. et al., "Submicrometre Particulates in Human Periprosthetic Tissues." Surface Modification Technologies V. By T. S. Sudarshan. The Institute of Materials, 117-23 (1992).
Capaccio, et al., "The Plastic Deformation of γ-Irradiated Linear Polyethylene," Journal of Polymer Science: Polymer Physics Edition 16:2083-2086 (1978).
Carlsson, D. J. et al., "Polypropylene Degradation by γ-Irradiation in Air." Polymer Stabilization and Degradation. By Peter Klemchuk. St. Louis: American. Chemical Society, 359-71 (1985).
Carlsson, D. J. et al., "Stabilization of Polyolefins to Gamma Irradiation." Radiation Effects on Polymers: Developed from a Symposium Sponsored by the Division of Polymer Chemistry, Inc. at the 200th National Meeting of the American Chemical Society, Washington, D.C., Aug. 26-31, 1990. By Roger L. Clough and Shalaby W. Shalaby. Washington, D.C.: American Chemical Society, 432-41 (1991).
Carlsson, et al., "Direct Observations of Macroperoxyl Radical Propagation and Termination by Electron Spin Resonance and Infrared Spectroseopies", Macromolecules 18: 2092-2094 (1985).
Carlsson, et al., "Oxidation Behavior of High Strength Chain-Extruded Polyethylene Fibers", Textile Res. 1. 58: 520 - 526 (1988).
Carrington, A. and Symons, M.C., "Structure and Reactivity of the Oxyanions of Transition Metals," Chem. Rev. 63: 443 - 460 (1963).
Cartasegna, S., "Silane-Grafted/Moisture-Curable Ethylene-Propylene Elastomers for the Cable Industry," Rubber Chem. Technol. 59:722-739 (1986).
Chanzy, H.D. and Marchessault, R.H., "Spontaneous Catalyst Fracture and Its Influence on Nascent Polyethylene Morphology," Macromolecules 2:108-110 (1969).
Chanzy, H.D. et al., "Nascent Structures During the Polymerization of Ethylene. 1. Morphology and Model of Growth," Kolloid-Z. u. Z. *Polym.* 251:563-576 (1973).
Chanzy, H.D., "Nascent Structures During the Polymerization of Ethylene. II. Claorimetric Study," *Colloid & Polym. Sci.* 252:8-14 (1974).
Chapiro, A., Radiation Chemistry of Polymeric Systems, vol. XV. New York: Interscience Publishers, pp. v, ix-xvi (1962).
Charlesby, A. "The Effects Of Ionising Radiation On Polymers," Irradiation Effects on Polymers. By D.W. Clegg and A.A. Collyer. London: Elsevier Applied Science, pp. 39-78 (1991).

Charlesby, A. and Pinner, S.H., "Analysis Of The Solubility Behaviour Of Irradiated Polyethylene And Other Polymers," Proceedings of the Royal Society of London. Series A, Mathematical and Physical Sciences, 249(1258):367-386 (Jan. 13, 1959).
Charlesby, A., Atomic Radiation and Polymers, p. v-ix (Pergamon Press, London, 1960).
Charnley, J. and Halley, D.K., "Rate Of Wear In Total Hip Replacement," Clin. Orthop. 112:170-179 (1975).
Charnley, J. and Kamangar, A., "The Optimum Size Of Prosthetic Heads In Relation To The Wear Of Plastic Sockets In Total Replacement Of The Hip," Med. & Biol. Engng. 7:31-39 (1969).
Clarke, I.C. et al., "Influence of THR Ball Diameter on Polyethylene Wear Rates," 19th Annual Meeting of the Society for Biomaterials, Birmingham, AL, p. 57 (Apr. 28-May 2, 1993).
Clegg, D.W. and A.A. Collyer, Irradiation Effects on Polymers. London: Elsevier Applied Science (1991).
Clough, R.L. and Shalaby, S.W., Radiation Effects on Polymers, ACS Symposium Series 475, p. 432-441 (Am. Chem. Soc., Washington, D.C. 1991).
Clough, R.L., "Accelerated-Aging Tests for Predicting Radiation Degradation of Organic Materials," Nuclear Safety 25(2):238-254 (1984).
Cohen, S.C. and Tabor, D., "Friction and Lubrication Of Polymers," Proceedings of the Royal Society of London. Series A, Mathematical and Physical Sciences, 291(1425):186-207 (Apr. 5, 1966).
Collier, J.P. et al., "The Biomechanical Problems of Polyethylene as a Bearing Surface," Clinical Orthopaedics and Related Research 261:107-113 (1990).
Cooper, et al., "Wear mechanisms of UHMWPE under unidirectional sliding", Trans. Fourth World Biomaterials Congress, Berlin, p. 619 (Apr. 24-28, 1992).
Cooper, J.R. et al., "Mechanisms of the Generation of Wear Particles of Ultra-High Molecular Weight Polyethylene," Wear Particles: From the Cradle to the Grave, Proceedings of the 18th Leeds-Lyon Symposium on Tribology, Sep. 1991, p. 29-39 (Elsevier, Netherlands, 1992).
Cooper, J.R. et al., "Observations of Residual Sub-Surface Shear Strains in the UFIMWPE Acetabular Cups of Chamley Hip Prostheses", Trans. Fourth World Biomaterials Congress, Berlin, Germany, p. 629 (Apr. 24-28, 1992).
Cooper, J.R. et al., "Birefringent studies of polyethylene wear specimens and acetabular cups", Wear 151:391-402 (1991).
Cowie, J.M.G., Polymers: Chemistry and Physics of Modem Materials, 2nd ed., (Chapman & Hall, New York, 1991).
Cracco, F. et al., "ESR Studies of Free Radical Decay in Irradiated Polyethylene," J. Chem. Phys. 37(10): 2449 2457 (Nov. 15, 1962).
Crugnola, A.M. et al., "Ultrahigh Molecular Weight Polyethylene as Used in Articular Prostheses (A Molecular Weight Distribution Study)," Journal of Applied Polymer Science 20:809-812 (1976).
Cullity, B.D., Elements of X-Ray Diffraction, 2nd ed. (Addison-Wesley Publishing Co., Inc., Reading, MA, 1978).
De Boer, J. and Pennings, A.J., "Crosslinking of Ultra-high Strength Polyethylene Fibers by Means of γ-Radiation," *Polym. Bull.* 5:317-324 (1981).
Desjardins, J.D. et al., "The use of a force-controlled dynamic knee simulator to quantify the mechanical performance of total knee replacement designs during functional activity," Journal of Biomechanics 33:1231-1242 (2000).
Dijkstra, D.J. and Pennings, A.J., "Cross-linking of porous gel-spun ultra-high molecular weight polyethylene by means of electron beam irradiation," Polymer Bulletin 20:557-562 (1988).
Dijkstra, D.J. and Pennings, A.J., "Cross-linking of ultra-high strength polyethylene fibres by . means of electron beam irradiation," Polymer Bulletin 17:507-513 (1987).
Dole, M, "Cross-linking and Crystallinity in Irradiated Polyethylene," *Polym.-Plast. Technol. Eng.* 13(1):41-64 (1979).
Dole, The Radiation Chemistry of Macromolecules, vol. I (Academic Press, New York, 1972).
Dole, The Radiation Chemistry of Macromolecules, vol. II (Academic Press, New York, 1973).
Dowling, et al., "The characteristics of acetabular cups worn in the human body", J. Bone & Joint Surgery 60-B(3): 375 - 382 (1978).

Dowson, D. et al. "The Wear Of High Molecular Weight Polyethylene With Particular Reference To Its Use In Artificial Human Joints," in Advances in Polymeric Function and Wear, L.H. Lee, ed. vol. 5B, Plenum Press, New York, pp. 533-551 (1976).
Dumbleton, J.H. and Shen, C., "The wear behavior of ultrahigh molecular weight polyethylene," Wear 37:279-289 (1976).
Dumbleton, J.H. et al., "A study of the wear of some materials in connection with total hip replacement," Wear 29:163-171 (1974).
Ebramzadeh, E.E. et al., "Comparison of porous ingrowth versus cemented acetabular components implanted with cemented femoral stems", AAOS, 1993 Ann. Mtg. Paper No. 245 (1993).
Elbert, K.E. et al., "In vivo changes in material properties of polyethylene and their effects on stresses associated with surface damage of polyethylene components", Trans. 34th Ann. Mtg. Orthop. Res. Soc., Atlanta, GA, p. 53 (Feb. 1-4, 1988).
Elf Atochem North America Inc., Philadelphia, PA, Halflife: Peroxide Selection Based on Half-Life (1992).
Eyerer, P. et al., "Characterization of UHMWPE hip cups run on joint simulators," J. Biomedical Materials Res. 21:275-291 (1987).
Findley, W.N. and Tracy, J.F. et al:, "16-Year creep of polyethylene and PVC," Polym Eng. Sci. 14(8):577-580 (1974).
Fisher, J. and Dowson, D., "Tribology of total artificial joints," Proc. Insin. Mech. Engrs. 205:7379 (1991).
Flory, P.J., "Theory of crystallization in copolymers," Trans. Faraday Soc. 51:848-857 (1955).
Flory, P.J., "Theory of Elastic Mechanisms in Fibrous Proteins," J Am. Chem. Soc. 78:5222-5235 (1956).
Flory, P.J., Principles of Polymer Chemistry (Cornell University Press, Ithaca, New York, 1953).
Frank, W., "Far-infrared spectrum of irradiated polyethylene," J. Polym Sci., Polym. Lett. Ed 15 679-682 (1977).
Franke, B., "Beitrage zur chemie des mangans," J. Pratt Chem. 35:31-43 (1887) [no translation].
Freedman, A.M. et al., "An investigation of permanganic etching of linear low-density polyethylene," J. Macromol. Sci.-Phys. B27(4):319-335 (1988).
Freedman, A.M. et al., "On quantitative pennanganic etching," Polymer 27:1163-1169 (1986).
Galante, J.O. et al., "The biologic effects of implant materials," Journal of Orthopaedic Research 9:760-775 (1991).
Gao, P. et al., "Development of anisotropy in ultra-high molecular weight polyethylene," Polymer 31:237-242 (Feb. 1990).
Gaylord, N.G. and Ballantine, D.S., Atomic Radiation and polymers. A. Charlesby, Pergamon Press, New York (1960).
Ghandi, K. and Salovey, R., "Dynamic mechanical behavior of copolymers containing carbon black," Polymer Engineering and Science 28(24):1628-1636 (Dec. 1988).
Gillen, K.T. and Clough, R.L., "Quantitative Confirmation of Simple Theoretical Models for Diffusion-Limited Oxidation", Ch. 28, pp. 457-472 in Radiation Effects on Polymers, R.L. Clough & S. W. Shalaby, eds., ACS Symposium Series 475, (Am. Chem. Soc., Washington, D.C., 1991).
Graff, R.J.L. et al., "On the site of the primary particles in Ziegler catalysts," J. Polym. Sci., Polymer Letters 8:735-739 (1970).
Grulke, E.A., Polymer Process Engineering, P.T.R. Prentice Hall, New Jersey, p. 419(1994).
Gvozdic, N. et al., "Kinetics of Free Radical Decay Reactions in Irradiated Isotactic Polypropylene," J. Phys. Chem. 85(11):1563-1569 (1981).
Habig, K.H. "Short communication: on the determination of wear rates," Wear 28:135-139 (1974).
Halldin, G.W. and Kamel, I.L., "Powder Processing of Ultra-High Molecular Weight Polyethylene. I. Powder Characterization and Compaction," Polym. Eng. Sci. 17(1):21-26 (1977).
Hayashi, K., "Clinical Applications Of Vanguard Basic Research," Seikei Geka [Orthopedic Surgery], 18:216-221 (Oct. 1, 1990).
Hendra, P.J. et al., "The morphology of linear polyethylenes crosslinked in their melts. The structure of melt crystallized polymers in general," Polymer 28:705-709 (1987).
Hermans, P.H. and Weidinger, A., "On the Determination of the Crystalline Fraction of Polyethylenes from X-Ray Diffraction," Makromol. Chem. 44-46:24-36 (1961).

Hikmet, R. and Keller, A., "Crystallinity Dependent Free Radical Formation and Decay in Irradiated Polyethylene in the Presence of Oxygen," Radial. Phys. Chem. 29(1):15-19 (1987).

Hinsch, B., "Sterilisation Methods for Implants Made of UHMWPE,", pp. 63-65 of Ultra-High Molecular Weight Polyethylene as Biomaterial in Orthopedic Surgery, H. G. Willert et al., ed. (Hogrefe & Huber Publishers, New York, 1991).

Hofmann, D. et al., "Crystallinity and Lateral Crystallite Size of Different LTHMW PE Materials," Journal of Applied Polymer Science 42:863-866 (1991).

Hood, R.W. et al., "Retrieval analysis of total knee prostheses: a method and its application to 48 total condylar prostheses," J. Biomed Mat. Res. 17:829-842 (1983).

Hosemann, R. et al., "Letters: Affine deformation of linear polyethylene during stretching and affine transformation to the original shape in the liquid state," Journal of Materials Science 7:963-964 (1972).

Hudis, M., "Surface Crosslinking of Polyethylene Using a Hydrogen Glow Discharge," Journal of Applied Polymer Science 16:2397-2415 (1972).

Hulse, G.E. et al., "Chemistry of Dicumyl Peroxide-Induced Crosslinking of Linear Polyethylene," Journal of Polymer Science, Polymer Chemistry Edition 19:655-667 (1981).

Iring, M. et al., "The Thermo-Oxidative Degradation of Polyolefines—Part 10, Correlation Between the Formation of Carboxyl Groups and Scission in the Oxidation of Polyethylene in the Melt Phase," Polymer Degradation and Stability 2:143-153 (1980).

Jahan, M.S. and Wang, C., "Combined Chemical and Mechanical Effects On Free Radicals In UHMWPE Joints During Implantation," Journal of Biomedical Materials Research 25:1005-1017 (1991).

Jahan, M.S. et al., "Effect of Post-Irradiation Storage Condition on Thermoluminescence From Ultra-High Molecular Weight Polyethylene," Journal of Luminescence 40 & 41:242-243 (1988).

Jenkins, H. and Keller, A., "Radiation-Induced Changes in Physical Properties of Bulk Polyethylene. I. Effect of Crystallization Conditions," J. Macromol Sci.-Phys. B11(3):301-323 (1975).

Jones, R.A. et al., "Radiation-Induced Crosslinking of Polyethylene in the Presence of Acetylene: A Gel Fraction, UV-Visible, and ESR Spectroscopy Study," Journal of Polymer Science: Part B: Polymer Physics. 31:807-819 (1993).

Kashiwabara, H., "ESR Application to Radiation Chemistry of Polymers," Radiat. Phys. Chem. 32(2): 203-208 (1988).

Kavesh, S. and Schultz, J.M., "Meaning and Measurement of Crystallinity in Polymers: A Review," Polymer Engineering and Science 9(6):452-460 (1969).

Kawai, T. et al., "The Effect of Crystallization Conditions on Radiation-Induced Cross-Link Formation in Polyethylene," Phil. Mag. 10:779-784 (1964).

Kawai, T. et al., "The Effect of Crystallization Conditions on Radiation-Induced Crosslink Formation in Polyethylene," Phil. Mag. 12:673-679 (1965).

Kawai, T. et al., "The Effect of Crystallization Conditions on Radiation-Induced Crosslink Formation in Polyethylene. Part I. The Basic Radiation-Solubility Relationship," Phil. Mag. 12:657-671 (1965).

Kawai, T. et al., "The Effect of Crystallization Conditions on Radiation-Induced Crosslink Formation in Polyethylene. Part VI. Some Effects in the Bulk Material," Phil. Mag. 14:1123-1130 (1966).

Keller, A. and Udagawa, Y., "Fold Surface of Polyethylene Single Crystals as Assessed by Selective Degradation Studies. II. Refinements of the Nitric Acid Degradation Method," J. Polym. Sci. Part A-2 9: 1793-1805 (1971).

Keller, A. and Ungar, G., "Radiation Effects And Crystallinity In Polyethylene," Radiation Physics Chemistry 22( 1/2) 155-181 (1983).

Keller, A. and Willmouth, F.M., "On the Morphology and Origin of the Fibres Observed in Nascent Ziegler Polyethylene," Die Makromol. Chem. 121:42-50 (1969).

Keller, A., "Radiation Effects and Crystallinity in Polyethylene and Paraffins", Ch. 2, pp. 37-113, of Development in Crystalline Polymers—1, D.C. Bassett, ed. (Appl. Sci. Publi., London, 1982).

Kitamaru, R. and Mandelkern, L., "Irradiation Cross Lining of Polyethylene. The Temperature Dependence of Cross Linking in the Crystalline and Amorphous States," Journal of American Chemical Society 86:3529-3534 (1964).

Klein, P.G. et al., "The Effect of Electron Irradiation on the Structure and Mechanical Properties of Highly Drawn Polyethylene Fibers," Journal of Polymer Science: Prt B: Polymer Physics 25:1359-1379 (1987).

Klemchuk, Peter P., Polymer Stabilization And Degradation, Based on a Symposium Sponsored by the Division of Polymer Chemistry at the 187th Meeting of the American Chemical Society, St. Louis, Missouri, Apr. 9-12, 1984.

Kresteva, M. et al., "Polymer Science: Melting of Nascent and Thermally Treated Super-High Molecular Weight Polyethylene," Colloid & Polymer Science 263:273-279 (1985).

Kunert, K.A. et al., Structural investigation of chemically crosslinked low density Polyethylene, Polymer, 22:1355-1360 (1981).

Kunert, K.A., "Comparison of Static Mechanical Properties of Crosslinked Polypropylene and Polyethylene," J. Polym. Sci., Polym. Lett. Ed. 19:479-482 (1981).

Kurth, M. et al., "Effects of Radiation Sterilization on UHMW— Polyethylene," p. 589, The Third World Biomaterials Congress (Apr. 21-25, 1988).

Kurtz, S.M. et al., "Advances in the processing, sterilization, and crosslinking of ultra-high molecular weight polyethylene for total joint arthroplasty," Biomaterials 20:1659-1688 (1999).

Kurtz, S.M. et al., "Post-Irradiation Aging and the Stresses in UHWMPE Components for Total Joint Replacement," 40th Ann. Mtg. Orthopaedic Res. Soc., New Orleans, LA, p. 584 (Feb. 21-24, 1994).

Lancaster, "Basic mechanisms of friction and wear of polymers," Plastics & Polymers 1(156): 297-306 (1973).

Lancaster, J.K., "Abrasive wear of polymers," Wear 14:223-239 (1969).

Lancaster, J.K., "Friction and Wear," in Jenkins ed., Polymer Science Ch. 14, pp. 959-1046 (North-Holland Publishing Company (1972).

Lee, E.H. et al., "Ion beam application for improved polymer surface properties," invited paper presented at the IX International Conference on Ion Implantation Technology, Gainesville, Florida, Nucl. Instrum. Meth. Phys. Res. B74: 326-330 (1993).

Li, S. et al., "Chemical degradation of polyethylene in hip and knee replacements," Trans. 38th Ann. Mtg. Orthopaedic Res. Soc., Washington, D.C., p. 41 (Feb. 17-20, 1992).

Loboda-Cackovic, J. et al., "Structural changes in paracrystallites of drawn polyethylene by irradiation," Colloid & Polym. Sci. 252:738-742 (1974).

Loboda-Cackovic, V.J. and Cackovic, H., "Die affine Deformation und die Vernetzungen in verstrecktem und danach bestrahltem Polyathylen," Kolloid— Z. Z. Polym. 250: 511-517 (1972).

Lombardi, A.V. et al., "Aseptic Loosening in Total Hip Arthroplasty Secondary to Osteolysis Induced by Wear Debris From Titanium-Alloy Modular Femoral Heads," J. Bone Joint Surg. 71-A(9): 1337-1342 (1989).

Lue, C.T. et al., "Approaching the Properties of UHMW-PE by Crosslinking Low Molecular Weight HDPE," AnTEC '84, pp. 538-541 (1984).

Marchessault, R.H. and Chanzy, H.D., "Polmerisation de polyethylene sur trichlorure de vanadium depose sur support. Morphologic du polymere naissant," J. Polym. Sci., Part C. 30:311-327 (1970).

Marchessault, R.H. et al., "Nascent Morphology of Polyolefins," CRC Crit. Rev. In Macromol. Sci. 1:315-349 (1972).

Matsuo, M. and Sawatari, C., "Cross-Linking of Ultrahigh Molecular Weight Polyethylene Films Produced by Gelation/Crystalization from Solution under Elongation Process," Macromolecules 19(7):2028-2035 (1986).

McGinnis, V.D., "Crosslinking with Radiation," in Encyclopedia of Polymer Science and Engineering, H.F. Mark et al., ed., 4: 418-449 (Wiley-Interscience Publ., John Wiley & Sons, New York, 1985).

McKellop, et al., "Polyethylene wear in non-conforming contact," 25th Ann. Mtg. Orthop. Res. Soc., San Francisco, CA, p. 72 (Feb. 20-22, 1979).

McKellop, H. "Metallic Wear in Total Knee Replacements," in Controversies of Total Knee Arthroplasty, V. M. Goldberg, ed., Ch. 5, pp. 51-60 (Raven Press, New York, 1991).

McKellop, H. and Clarke, I.C., "Degradation and Wear of Ultra-High-Molecular-Weight Polyethylene", in Corrosion & Degradation of Implant Materials: Second Symposium, A.C. Fraker, et al., ed., pp. 351-368 ASTM Special Technical Publication 859, ASTM, Philadelphia, PA, 1985).

McKellop, H. and Lu, B., "Friction, Lubrication and Wear of Cobalt-Chromium, Alumina and Zirconia Hip Prostheses Compared on a Joint Simulator", 38th Ann. Mtg. Orthop. Res. Soc., Washington, D.C., p. 402 (Feb. 17-20, 1992).

McKellop, H. et al, "Wear of acetabular cups of conventional and modified UHMWw polyethylenes compared on a hip joint simulator", 38th Ann. Mtg. Orthop. Res. Soc., Washington, D.C., p. 356 (Feb. 17-20, 1992).

McKellop, H. et al., "Accelerated Ageing of Irradiated UHMW Polyethylene for Wear Evaluations," 42nd Ann. Mtg. Orthopaedic Res. Soc., Atlanta, GA, p. 483 (Feb. 19-22, 1996).

McKellop, H. et al., "Comparison of surface roughness on new and retrieved metal and ceramic total hip prostheses," 19th Ann. Mtg. Soc. Biomaterials, Birmingham, AL, p. 85 (Apr. 28-May 2, 1993).

Mckellop, H. et al., "Development of an Extremely Wear-Resistant Ultra High Molecular Weight Polyethylene for Total Hip Replacements," J. Ortho. Res. 17(2):157-167 (1999).

McKellop, H. et al., "Effect of increased density and crystallinity on the wear of UHMW polyethylene acetabular cups", Trans. Fourth World Biomaterials Congress, Berlin, Germany, p. 117 (Apr. 24-28, 1992).

McKellop, H. et al., "Evidence for the generation of sub-micron polyethylene wear particles by microadhesive wear in acetabular cups", 19th Ann. Mtg. Soc. Biomaterials, Birmingham, AL, p. 184 (Apr. 28-May 2, 1993).

McKellop, H. et al., "Friction and wear properties of polymer, metal and ceramic prosthetic joint materials evaluated on a multichannel screening device," J. Biomed Materials Rex 15:619-653 (1981).

McKellop, H. et al., "Wear characteristics of UHMW polyethylene: A method for accurately measuring extremely low wear rates," J. Biomed Mater. Res 12:895-927 (1978).

McKellop, H., "Bearing Surfaces in Total Hip Replacements: State of the Art and Future Developments," AAOS Instructional Course Lectures, 50:165-179 (2001).

McKellop, H., "What are the Contributions of Polyethylene and the Bearing Surfaces to the Lysis Problem?", presented in the Symposium on "Particulate Debris in Total Hip Arthroplasty," American Academy of Orthopaedic Surgeons, 1993 Ann. Mtg. (Feb. 1993).

McKellop, H.A. and Rostlund, T.V., "The wear behavior of ion-implanted Ti-6Al-4V against UHMW polyethylene," J. Biomed Mater. Res. 24:1413-1425 (1990).

McRae, M.A. and Maddams, W.F., "Infrared Spectroscopic Studies on Polyethylene, 4," DieMakromot Chem 177:473-484 (1976).

Meinel, G. and Peterlin, A., "Changes in Noncrystalline Regions of Polyethylene During Annealing," J. Polym. Sci. Part. B, Polym. Letters 5:613-618 (1967).

Mirra, J.M. et al., "The Pathology of Failed Total Joint Arthroplasty," Clin. Orthop. Rel. Res. 170: 175-183 (1982).

Mitsui, H and Hosoi, Fu., "γ-Radiation-Induced Cross-Linking of Polyethylene," Polym J. 4(1): 79-86 (1973).

Mitsui, H. and Hosoi, F., "Acceleration of Fluorine-Containing Monomer-Acetylene System for the γ-Radiation-lnduced Cross-Linking of Polyethylene," Polym. J. 3(1):108-110 (1972).

Mitsui, H. et al., "Accelerating Effect of Acetylene on the γ-Radiation-lnduced Cross-Linking of Polyethylene," Polym. J. 6(1): 20 - 26 (1974).

Miyaji, H. and Gail, P.H., "Annealing of nodular linear polyethylene crystallized from the glass," Polymer 22:701-703 (1981).

Mukherjee, A.K. et al., "Conventional Crosslinking StudiesOn Low Density Polyethylene Monofilaments," Die Angewandte Makromolekulare Chemie 173:205-212 (Nr. 9390) (1989).

Munoz-Escalona, A.and Parada, A., "Factors Affecting the Nascent Structure and Morphology of Polyethylene Obtained by Heterogeneous Ziegler-NATTA Catalyst. III. Crystal morphology and growth mechanism," J. Cryst. Growth 48:250-258 (1980).

Munteanu, D., "Moisture-Crosslinkable Silane-Grafted Polyolefins," in Metal Containing Polymeric Systems, J.E. Sheats, et al., eds., pp. 479-509 (Plenum Press, New York, 1985).

Nagasawa, T. and Kobayashi, K., "Paracrystalline Structure of Polymer-Crystal Lattice Distortion Induced by Electron Irradiation," J. Appl. Phy. 41(11):4276-4284 (1970).

Nakayama, K. et al., "Structure and Mechanical Properties of Ultra-High Molecular Weight IPolyethylene Deformed Near Melting Temperature," Pure & Appl. Chem. 63(12):1793-1804 (1991).

Narkis, M. and Miltz, J., "Chemically Crosslinked High-Density Polyethylene," Journal of Applied Polymer Science13:713-720 (1969).

Narkis, M. et al., "Some Properties of Silane-Grafted Moisture-Crosslinked Polyethylene," Polym. Eng. Sci. 25(13):857-862 (1985).

Naylor, K.L. and Phillips, P.J., "Optimization of Permanganic Etching of Polyethylenes for Scanning Electron Microscopy," J. Polym. Sci., Polym. Phys. Ed 21:2011-2026 (1983).

Nikolova, M. and Nedkov, E., "WAXS and SAXS Investigation of the Supermolecular Structure of LOPE Films Irradiated with Fast Electrons," J. Macromol. Sci.- Phys. B27(1):1-17 (1988).

O'Donnell, et al., Principles of Radiation Chemistry (American Elsevier Publishing Co., Inc., New York, 1970).

O'Donnell, J.H., "Radiation Chemistry of Polymers," The Effects of Radiation on High Technology Polymers, E. Reichmanis & J.H. O'Donnell, eds., ACS Symposium Series 381, Ch. I, pp. 1-13 (American Chemical Society, Washington, D.C., 1989).

Olley, R.H. and Bassett, D.C., "An Improved Permanganic Etchant for Polyolefines", *Polymer* 23: 1707-1710 (1982).

Olley, R.H. et al. "A Permanganic Etchant for Polyolefines," J. Polym. Sci., Polym. Phys. Ed. 17: 627-643 (1979).

Oonishi, H. et al., "Wear resistance of gamma-ray irradiated U.H.M.W. polyethylene socket in total hip prostheses—wear test and long term clinical results," Third World Biomaterials Congress, Kyoto, Japan, p. 588 (Apr. 21-25, 1988).

Palmer, R.A. et al., "The Texture of Melt Crystallised Polyethylene as Revealed by Selective Oxidation", Makromol Chem. 74: 174-189 (1964).

Patel, G.N. and Keller, A., "Crystallinity And The Effect Of Ionizing Radiation In Polyethylene. II. Crosslinking In Chain-Folded Single Crystals," Journal of Polymer Science, Polymer Physics Edition, vol. 13, 323-331 (1975).

Patel, G.N. and Keller, A., "Crystallinity And The Effect of Ionizing Radiation In Polyethylene. III. Experiment On The Irradiation-Induced Crosslinking in n-Hexatriacontane," Journal of Polymer Science, Polymer Physics Edition, vol. 13, 333-338 (1975).

Patel, G.N. and Keller, A., "Crystallinity and the Effects of Ionizing Radiation in Polyethylene. 1. Crosslinking and Crystal Core," J. Polym. Sci., Polym. Phys. Ed. 13: 303-321 (1975).

Patel, G.N., "Chemical Methods in Polymer Physics," in Methods of Experimental Physics L. Marton and C. Marton, eds., vol. 16, Part B, Ch. 8, pp. 237-286 (Academic Press, New York, 1980).

Patel', G.N., "Polymers—Part B: Crystal Structure and Morphology," (1980).

Peacock, A.J., "The efficiency of crosslinking linear polyethylene by using dicumyl peroxide," Polym. Commun. 28:259-260 (1987).

Perkins, W.G. et al., "Effect of Gamma Radiation and Annealing on Ultra-Oriented Polyethylene," Polym. Eng. & Sci. 18(6):527-532 (1978).

Pethrick, R.A., "Microlithography," in Irradiation Effects on Polymers, D.W. Clegg & A.A Collyer, eds., Ch. 10, pp. 383-430 (Elsevier Applied Science, New York, 1991).

Pichat, et al., "Ion implantation on metal and polymer components for joint prostheses", in Clinic Implant Materials. G. Heimke, et al., ed., vol. 9: Advances in Biomaterials, pp. 385-390 (Elsevier Science Publishers, B. V., Amsterdam, 1990).

Pinchbeck, P.H., "A review of plastic bearings," Wear %:85-113 (1962).

Proest, D.J. "Fold Surface of Polyethylene Single Crystal as Assessed by Selective Degradation. I. Ozone Degradation Method,"J. Polym. Sci. Part A2, 9:1777-1791 (1971).

Ratner, S.B. et al., "Connection Between Wear-Resistance of Plastics and Other Mechanical Properties," in: Abrasion of Rubber, pp. 145-154 (McLarten & Sons, London, 1967).

Reichmanis, E. et al., Irradiation of Ploymeric Materials ACS Symposium Seried 527 (Americam Chemical Society, Washington, D.C., 1993).
Reichmanis, E., "Radiation Chemistry of Polymer for Electronic Applications" in The Effects of Radiation on High-Technology Polymers, E. Reichmanis & J.H. O'Donnell, eds., ACS Symposium Series 381, ch. 9, pp. 132-154 (American Chemical Society, Washington, D.C., 1989).
Revol, J.F. et al., "Electron Microscope Investigation on Nascent Polyethylene," J. Crys. Growth 48:240-249 (1980).
Rhee, S.H. and Dumbleton, J.H., "The application of the zero wear model to joint prostheses," Wear 36:207-224 (1976).
Rieu, J. et al., "Ion implantation effects on friction and wear prosthesis materials," Biomaterials 12:139-143 (1991).
Rimnac, C.M. et al., "In vitro chemical and mechanical degradation of UHMWPE: Three month Results," 19th Ann. Mtg. Soc. Biomaterials, Birmingham, AL, p. 331 (Apr. 28-May 2, 1993).
Rimnac, C.M. et al., "Characterization of material properties of ultra high molecular weight polyethylene before and after implantation", Soc. for Biomaterials, Implant Retrieval Symposium, St. Charles, IL, p. 16 (Sep. 17-20, 1992).
Rimnac, C.M. et al., "Chemical and mechanical degradation of UHMW polyethylene: an in vitro Investigation," ASTM Symposium on Biomaterials' Mechanical Properties, Pittsburgh, PA (May 5-6, 1992).
Rimnac, C.M. et al., "Degradation Of UHMW Polyethylene", J Applied Biomaterials, pp. 25-26, Submitted Jun. 1993.
Rimnac, C.M. et al., "Post-Irradation Aging of UHMWPE," 19th Ann. Mtg. Soc. Biomaterials, Birmingham, AL, p. 328 (Apr. 28-May 2, 1993).
Rimnac, C.M. et al., "Retrieval of orthopaedic implants at the hospital for special surgery, " Symposium on Retrieval & Analysis of Surgical Implants & Biomaterials, p. 2 (1988).
Rimnac, C.M., "Acetabular cup wear in total hip arthroplasty," Orthopaedic Clinics of North America 19(3):631-636 (1988).
Rimnac, C.M., "Observations of surface damage and degradation on retrieved PCA knee implants," 38th Ann. Mtg. Orthopaedic Res. Soc., Washington, D.C., p. 330 (Feb. 17-20, 1992).
Rodriguez, "Principles of Polymer Systems," 2nd ed., pp. 216-218 (Hemisphere Publishing Corp., Washington, 1982).
Rose, R.M. et al., "A prognosis for ultra high molecular weight polyethylene," Biomaterials 11:63-67 (1990).
Rosen, S.L., ed., Fundamental Principles of Polymeric Materials 2nd ed., p. 40 (John Wiley & Sons, Inc., New York, 1993).
Rostlund, T. et al., "Wear of ion-implanted pure titanium against UHMWPE," Biomateriais 10:176-181 (1989).
Sakai, Y. et al., "Effect of electron beam irradiation on simultaneously biaxially drawn ultra, high molecular weight polyethylene dried gel films," Polymer 34(16):3362-3367 (1993).
Salovey, et al., "The Influence of Crystallization Conditions on Radiation Effects in Polyethylene—I. Crystallization from Dilute Solution and from the Melt; II. Crystallization from Concentrated Solutions," J. Bell System Tech. 40: 1397-1408, and 1409-1419, for Parts I and II, respectively (1961).
Salovey, R. and Bassett, D.C., "Irradiation of Annealed Polyethylene Crystals," J. Appl. Phys. 35(11):3216-3221 (1964).
Salovey, R., "Irradiation of Crystalline Polyethylene," J. Polym. Sci. 61:463-473 (1962).
Salovey, R., "On the Morphology of Cross linking Polymers," J. Polym. Sci. Part. B, Polym. Letters 2:833-834 (1964).
Salovey, R., "Polymer Letters On The Morphology of Crosslinking Polymers", Polymer Letters vol. 2, pp. 835-838 (1964).
Salovey, R., "Single Crystals," in The Radiation Chemistry of Macromolecules, vol. 2, M. Dole, ed., Ch. 15, pp. 307-312 (Academic Press, New York, 1973).
Salvati, E.A. et al., "Cemented total hip replacement: Long Tenn results and future outlook," Instructional Course Lectures, XL:121-134, American Academy of Orthopaedic Surgeons (1991).
Salyer, I.O, "Thermal-Energy Storage in Cross linked Pellets of High-Density Polyethylene for Home Heating and Cooling via Off-Peak Electric Power Utilization", Appl. Polym. Sci. 28:2903-2924 (1983).

Sanford, W.M. et al., "Accelerated oxidative aging testing of UHMWPE," 41st Ann. Mtg. Oprthopaedic Res. Soc., p. 119-20 (1995).
Sarmiento, A. et al., "Failure due to aggressive osteolysis in hips with Morscher acetabular cups," AAOS, 1993 Ann. Mtg. , Paper No. 229 (Feb. 20, 1993).
Sauer, J.A. et al., "Influence of Molecular Weight on Fatigue Behavior of Polyethylene and Polystyrene," Polym. Eng Sci. 17(4):246-250 (1977).
Sawatari, C. et al., "Temperature-dependence of mechanical and morphological properties of ultra-high molecular weight polyethylene cross-linked by electron beam irradiation," Colloid & Polym. Sci. 266:316-323 (1988).
Scheier, H. and Sandel, J., "Wear affecting the plastic cup in metal-plastic endoprostbeses," in Total Hip Prostheses, N. Gschwend & H. U. Debrunner ed., translated by P. Konstam, 186-190 (Hans Huber Publishers Bern Stuttgart Vienna, 1976).
Schmalzried, T.P. et al., "Periprosthetic bone loss in total hip arthroplasty," J. Bone Joint Surg. 74-A(6): 849-863 (1992).
Schonhorn, H. and Ryan, W., "Surface Cross linking of Polyethylene and Adhesive Joint Strength," J. Appl. Polym. Sci. 18:235-243 (1974).
Scott, H.G. and Humphries, J.F., "Novel Cross linking Method for Polyethylene," Modem Plastics 50:82-87 (Mar. 1973).
Shadrake, W.G. and Guiu, F., "Interactions between cross-links and dislocations in polyethylene crystals: a model of irradiation hardening," J. Mater. Sci. 17:145-156 (1982).
Shen, F.W., PhD. Dissertation, Effect of Irradiation on Chemically Crosslinked Ultrahigh Molecular Weight Polyethylene (Dec. 1994).
Shen, F.W., PhD. Dissertation: "Effect of Irradiation on Chemically Crosslinked Ultrahigh Molecular Weight Polyethylene," p. 61 (UMI Company, Ann Arbor, Michigan, 1995).
Shimada, S. et al., "Free radicals trapped in polyethylene matrix: 2. Decay in single crystals and diffusion," Polymer 18:25-31 (1977 ).
Shimada, S. et al., "Relation between diffusion controlled decay of radicals and γ-relaxation in polyethylene and polyoxymethylene," Polymer 22:1377-1384 (1981).
Slichter, W.P. and Mandell, E.R., "Molecular Structure and Motion in Irradiated Polyethylene," J Phys. Chem. 62: 334-340 (1958).
Smith, P. et al., "Drawing of virgin ultrahigh molecular weight polyethylene: an alternative route to high strength/high modulus materials," J. Mater. Sci. 22:523-531 (1987).
Sohma, J., "Radical Migration as an Elementary Process in Degradation," Pure & Appl. Chem. 55(10):1595-1601 (1983).
Stockmayer, W.H., "Theory of Molecular Size Distribution and Gel Formation in Branched Polymers", J. Chem. Phys. 12(4):125-131 (1944).
Streicher, et al., "Examination of Explanted Hip Joint Cups Made of UHMW-PE", in H-G Willert, et al., ed., Ultra-High Molecular Weight Polyethylene as Biomaterial in Orthopedic Surgery, pp. 196-201 (Hogrefe & Huber Publishers, New York, 1991).
Streicher, R.M., "Change in Properties of High Molecular Weight Polyethylenes After Ionizing Irradiation for Sterilization and Modification," Radiation processing for plastics and rubber III, Department of Medical Engineering, Sulzer Brothers Ltd., Winterthur, Switzerland (1988).
Streicher, R.M., "Improving UHMWPE by Ionizing Irradiation Cross linking During Sterilization," 17th Ann. Mtg, Soc. Biomaterials, Scottsdale, AZ, p. 181 (May 1-5, 1991).
Sun, D.C. et al., "Development of an Accelerated Aging Method for Evaluation of Long-Term Irradiation Effects on UHMWPE Implants", Polymer Pre prints 35(2):969-970 (1994).
Sun, D.C. et al., "On the Origins of a Subsurface Oxidation Maximum and its Relationship to the Performance of UHMWPE Implants", 21st Ann. Mtg. Soc. Biomaterials, San Francisco, CA, p. 362 (Mar. 18-22, 1995).
Sun, D.C. et al., "The Origin of the White Band Observed in Direct Compression Molded UHMWPE Insert", 20th Ann. Mtg. Soc. Biomaterials, Boston, MA, p. 121 (Apr. 5-9, 1994).
Sun, L. et al., "Model Filled Polymers. VII: Flow Behavior of Polymers Containing Monodisperse Cross linked Polymeric Beads," Polym. Eng. & Sci. 32(12):777-785 (1992).

Tang, F. and Huyser, E.S., "Thermal Decomposition Of Bifunctional Peroxides," J. Org. Chem. 42(12):2160-2163 (1977).

Tervoort-Engelen, Y.M.T. and Lemstra, P.J., "Morphology of nascent ultra-high molecular weight polyethylene reactor powder: chain-extended versus chain-folded crystals," Polymer Communications 32(11):343-345 (1991).

Truss, R.W. et al., "Cold Compaction Molding and Sintering of Ultra High Molecular Weight Polyethylene," Polym. Eng. & Sci. 20(11):747-755 (1980).

Tsuruta, A. et al., "Annealing of Ultra-Oriented High Density Polyethylene Extrudates," Polym. Eng. & Sci.23(9):521-529 (1983).

Turner, D.T., "The Influence of the Temperature of Irradiation on the Formation of Polymer Networks", J. Polym. Sci. Part. B, Polym. Letters 1:101-103 ( 1963).

Ungar, G. et al., "Effect of radiation on the crystals of polyethylene and paraffins: I. Formation of the hexagonal lattice and the destruction of crystallinity in polyethylene," Polymer 21:1273-1277 (1980).

Ungar, G., "Review: Radiation effects in polyethylene and n-alkanes," J. Mater. Sci. 16:2635-2656 (1981).

Wang, A. et al., "Role of Cyclic Plastic Deformation in the Wear of UHMWPE Acetabular Cups," J. Biomedical Materials Res. 29:619-626 (1995).

Wang, A. et al., "Wear Mechanisms of UHMWPE in Total Joint Replacements", Wear 187-183: 241-249 (1995).

Wang, X-Y, et al., "Processing of Ultrahigh Molecular Weight Polyethylene," J. App. Polym. Sci. 35:2165-2171 (1988).

Ward, I.M. and Hadley, D.W., eds., An Introduction to the Mechanical Properties of Solid Polymers (John Wiley Sons, New York, 1993).

Waterman, D.C. and Dole, M., "The Radiation Chemistry of Polyethylene. X Kinetics of the Conversion of Alkyl to Allyl Free Radicals," J Phys. Chem. 74(9):1913-1922 (1970).

Weast, Robert C., Melvin J. Astle, and William H. Beyer. "Physical Constants of Organic Compounds." CRC Handbook of Chemistry and Physics: a Ready-reference Book of Chemical and Physical Data. 67th ed. Boca Raton, FL: CRC, C51, C-550 (1986).

Weidinger, A. and Hermans, P.H., "On the Determination of the Crystalline Fraction of Isotactic Polypropylene from X-Ray Diffraction," Mackromol. Chem. 50:98-115 (1961).

Willert, H.-G. and Semlitsch, M., "Reactions of the articular capsule to wear products of artificial joint prostheses," J. Biomed Mater. Res. 11:157-164 (1977).

Williams, T.F. and Dole, M., "Physical and Inorganic Chemistry: Irradiation Of Polyethylene. III. Influence Of Temperature And Phase", Journal of the American Chemical Society, 81(12):29192926 (Jul. 2, 1959).

Woods, D.W. et al., "Improved Mechanical Behaviour in Ultra-High Modulus Polyethylenes by Controlled Cross-Linking," Plastics and Rubber Processing & Applications 5:157-164 (1985).

Wright, T.M. et al., "Design considerations for an acetabular component made from an Enhanced form of ultra high molecular weight polyethylene," 37th Ann. Mtg. Orthop. Res. Soc. , Anaheim, CA, p. 248 (Mar. 4-7, 1991).

Wright, T.M. et al., "Failure of carbon fiber-reinforced polyethylene total knee-replacement components," J. Bone Joint Surg.70-A(6):926- 932 (1988).

Wright, T.M. et al., "Wear of polyethylene in total joint replacements. Observations from retrieved PCA knee implants," Clin. Orthop. & Related Res. 276:126-134 (1992).

Wunderlich, B and Melillo, L., "Morphology and Growth of Extended Chain Crystals of Polyethylene," Die Makromol. Chemie 118:250-264 (1968).

Wunderlich, B. and Czornyj, G., "A Study of Equilibrium Melting of Polyethylene," Macromolecules 10(5):906-913 (1977).

Wunderlich, B. et al., "Crystallization of Linear High Polymers from the Monomer," Kolloid-Z Z. Polym. 204:125 (1965).

Wunderlich, B. et al., "Note: Heat of Fusion of Polyethylene," J. Polym. Sci. 5(A•2):987-988 (1967).

Wunderlich, B., Macromolecular Physics, vol. 1 (Academic Press, New York, 1973).

Wunderlich, B., Macromolecular Physics, vol. 2 (Academic Press, New York, 1976).

Yang, M. and Salovey, R., "Directional crystallization of polyethylene oxide by laser irradiation," J. Polymer Sci.: Part B: Polym. Phys. 28:245-256 (1990).

Yang, M. et al., "Laser irradiation of polyethylene oxide," J. Vac. Sci Technol. A7(4):2802-2804 (1989).

Yasuniwa, M. and Nakafuku, C., "High Pressure Crystallization of Ultra-High Molecular Weight Polyethylene," Polymer J. 19(7):805-813 (1987).

Yeh, G.S. et al., "Radiation-induced crosslinking: Effect on structure of polyethylene," Colloid & Polym. Sci. 263:109-115 (1985).

Yoda, O. and Kuriyama, I., "Crystallite size distribution and the lattice distortions in highly $\gamma$-irradiated linear polyethylene," J. Mater. Sci. 14:1733-1743 (1979).

Yoda, O. and Kuriyama, I., "Measurement of the Unit Cell Dimension of Highly $\gamma$-Irradiated Polyethylene Crystal," Jpn. J. Appl Phys. 16(8):1447-1448 (1977).

Yoda, O. and Odajima, A., "Analysis of the Asymmetric 002 X-Ray Line Profiles of $\gamma$-Irradiated Polyethylene," Jpn. J. Appl. Phys. 19:1241-1245 (1980).

Young, R.J. and Lovell, P.A., ed., Introduction to Polymers, 2nd ed. (Chapman & Hall, New York, 1991).

Zachariades, A.E. and Kanamoto, T., "The Effect of Initial Morphology on the Mechanical Properties of Ultra-High Molecular Weight Polyethylene," Polym. Eng. & Sci. 26(10):658-661 (1986).

Zachariades, A.E. and Logan, J.A., "The Melt Anisotropyof Ultrahigh-Molecular-Weight Polyethylene," J. Polym. Sci.: Polym. Phys. Ed 21:821-830 (1983).

Zachariades, A.E., "The Effect of Powder Particle Fusion on the Mechanical Properties of Ultra- High MolecIllar Weight Polyethylene," Polym. Eng. & Sci. 25(12): 747-750 (1985).

\* cited by examiner

CROSSLINKING OF POLYETHYLENE FOR LOW WEAR USING RADIATION AND THERMAL TREATMENTS

This is a continuation of co-pending U.S. patent application Ser. No. 10/936,149, filed on Sep. 7, 2004, which is a continuation of Ser. No. 09/795,229, filed on Feb. 26, 2001, entitled "CROSSLINKING OF POLYETHYLENE FOR LOW WEAR USING RADIATION AND THERMAL TREATMENTS", and issued as U.S. Pat. No. 6,800,670 on Oct. 5, 2004, which is a continuation of application Ser. No. 09/214,586, filed on Jan. 6, 1999, and issued as U.S. Pat. No. 6,228,900, on May 8, 2001, which is the national phase filing of Patent Cooperation Treaty application number PCT/US97/11947, filed on Jul. 8, 1997, which is based on U.S. provisional applications: Ser. No. 60/017,852 filed on Jul. 9, 1996; Ser. No. 60/025,712 filed on Sep. 10, 1996; and Ser. No. 60/044,390, filed on Apr. 29, 1997. The entire contents of the predecessor applications are herein expressly incorporated by reference.

TECHNICAL FIELD OF THE INVENTION

The present invention relates to polymers. It discloses methods for enhancing the wear-resistance of polymers by crosslinking and thermally treating them. The polymers disclosed herein are useful for making implants, for example, as components of artificial joints such as acetabular cups.

BACKGROUND OF THE INVENTION

Ultrahigh molecular weight polyethylene (hereinafter referred to as "UHMWPE") is commonly used to make prosthetic joints such as artificial hip joints. In recent years, it has become increasingly apparent that tissue necrosis and interface osteolysis, in response to UHMWPE wear debris, are primary contributors to the long-term loosening failure of prosthetic joints. For example, wear of acetabular cups of UHMWPE in artificial hip joints introduces many microscopic wear particles into the surrounding tissues. The reaction to these particles includes inflammation and deterioration of the tissues, particularly the bone to which the prosthesis is anchored. Eventually, the prosthesis becomes painfully loose and must be replaced.

Improving the wear resistance of the UHMWPE socket and, thereby, reducing the rate of production of wear debris would extend the useful life of artificial joints and permit them to be used successfully in younger patients. Consequently, numerous modifications in physical properties of UHMWPE have been proposed to improve its wear resistance.

UHMWPE components are known to undergo a spontaneous, post-fabrication increase in crystallinity and changes in other physical properties. {See e.g., Rimnac, C. M., et al., *J. Bone & Joint Surgery*, 76-A(7):1052-1056 (1994)}. These changes occur even in stored (non-implanted) cups after sterilization with gamma radiation, which initiates an ongoing process of chain scission, crosslinking, and oxidation or peroxidation involving the free radicals formed by the irradiation. These degradative changes may be accelerated by oxidative attack from the joint fluid and cyclic stresses applied during use.

In an attempt to improve wear resistance, DePuy-DuPont Orthopaedics fabricated acetabular cups from conventionally extruded bar stock that previously had been subjected to heating and hydrostatic pressure that reduced fusion defects and increased the crystallinity, density, stiffness, hardness, yield strength, and increased the resistance to creep, oxidation and fatigue. Alternatively, silane cross-linked UHMWPE (XLP) has also been used to make acetabular cups for total hip replacements in goats. In this case, the number of in vivo debris particles appeared to be greater for XLP than conventional UHMWPE cup implants {Ferris, B. D., *J. Exp. Path.*, 71:367-373 (1990)}.

Other modifications of UHMWPE have included: (a) reinforcement with carbon fibers; and (b) post-processing treatments such as solid phase compression molding. Indeed, carbon fiber reinforced polyethylene and a heat-pressed polyethylene have shown relatively poor wear resistance when used as the tibial components of total knee prosthesis. {See e.g., Rimnac, C. M., et al., *Trans. Orthopaedic Research Society*, 17:330 (1992)}.

Recently, several companies have modified the method of radiation sterilization to improve the wear resistance of UHMWP components. This has typically involved packaging the polyethylene cups either in an inert gas (e.g., Howmedica, Inc.), in a partial vacuum (e.g., Johnson & Johnson, Inc.) or with an oxygen scavenger (e.g., Sulzer Orthopaedics, Inc.).

SUMMARY OF THE INVENTION

The present invention comprises two aspects:

The first aspect of the invention presents a method for increasing the wear resistance of a polymer by crosslinking the polymer, followed by thermally treating the crosslinked polymer. Non-limiting examples of the thermal treatments are remelting or annealing. Preferably, the polymer is crosslinked by gamma irradiation in the solid state prior to being modified to a desired final form or shape of the final product. In the preferred embodiment, the surface layer of the crosslinked and thermally treated polymer, which is the most oxidized and least crosslinked part of the polymer, is removed, e.g., in the process of machining the final product out of the irradiated bar and thermally treated bar or block. The radiation dose is also preferably adjusted so that the optimal dose occurs within the solid polymer bar or block at the level of the bearing surface of the final product. Also presented are the polymers made from this method; methods for making products (e.g., in vivo implants) from these polymers; and the products (e.g., in vivo implants) made from these polymers.

The second aspect of the invention provides a systematic method for determining an optimal balance among wear resistance and other physical and/or chemical properties that are deemed important to the long-term performance of an implant in vivo, and applying this optimal balance to determine the appropriate crosslinking and thermal treatment conditions for processing a polymer. A flowchart is provided as a non-limiting illustration of the method for determining the optimal balance. Also provided are methods for treating polymers which apply the above appropriate crosslinking and thermal treatment conditions; the polymers produced by these methods; methods for making products (e.g., in vivo implants) from these polymers; and the products (e.g., in vivo implants) made from these polymers.

DETAILED DESCRIPTION OF THE INVENTION

Figure 1:
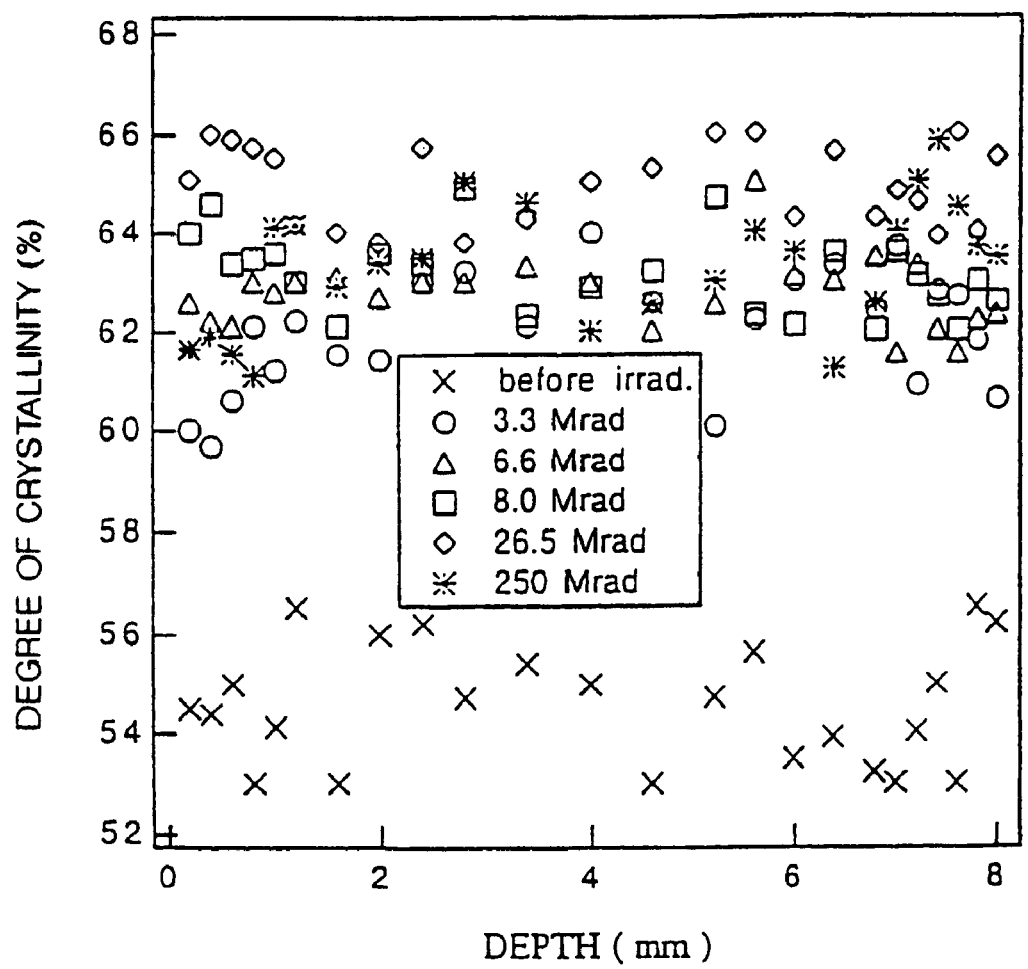
FIG. 1 presents the degree of crystallinity vs. depth at indicated doses for UHMWPE that was irradiated in a vacuum (i.e., a low-oxygen atmosphere).

Abbreviations used in this application are as follows:
UHMW—ultra-high molecular weight
UHMWPE—ultra-high molecular weight polyethylene
HMW—high molecular weight
HMWPE—high molecular weight polyethylene The present invention contains two aspects. The first aspect of the invention provides methods for improving the wear resistance of a polymer by crosslinking (preferably the bearing surface of the polymer) and then thermally treating the polymer, and the resulting novel polymer. Preferably, the most oxidized surface of the polymer is also removed. Also presented are the methods for using the polymeric compositions for making products and the resulting products, e.g., in vivo implants. Specific examples of this method are presented in the section: "I. First Aspect of the Invention: Polymeric Compositions with Increased Wear Resistance" and "I (A) Further Examples of the First Aspect of the Invention", below.

The method of the invention utilizes irradiation for crosslinking a polymer followed by thermal treatment to decrease the free radicals to produce a preformed polymeric composition. The term "preformed polymeric composition" means that the polymeric composition is not in a final desired shape or form (i.e., not a final product). For example, where the final product of the preformed polymeric composition is an acetabular cup, irradiation and thermal treatment of the polymer could be performed at pre-acetabular cup shape, such as when the preformed polymeric composition is in the form of a solid bar or block.

A second aspect of the invention provides a systematic method (an example of which is illustrated in the flowchart, below) for determining the optimal parameters for the above mentioned crosslinking and thermal treatment. This second aspect provides a method for determining the maximum possible improvement in wear resistance, consistent with keeping the other physical and/or chemical propert(ies) within the user's desired limits, with the least amount of trial and error testing. Once the optimal parameters (i.e., crosslinking conditions such as radiation dose when radiation is used to crosslink the polymer, and thermal treatment parameters) are determined by this method, the polymer will then be processed according to the optimal parameters. Thus, this protocol renders the development of a preformed polymeric composition with particular chemical/mechanical characteristics routine without resort to undue experimentation. Also presented are the methods for using the preformed polymeric composition for making products, and the products, e.g., in vivo implants.

In the present invention, the wear resistance of the polymer is improved by crosslinking. The crosslinking can be achieved by various methods known in the art, for example, by irradiation from a gamma radiation source or from an electron beam, or by photocrosslinking. The preferred method for crosslinking the polymer is by gamma irradiation. The polymer is preferably crosslinked in the form of an extruded bar or molded block.

In the preferred method, the crosslinked polymer is subjected to thermal treatment such as by remelting (i.e., heated above the melting temperature of the crosslinked polymer) or annealing (i.e., heated at below the melting temperature of the crosslinked polymer) to produce the preformed polymeric composition.

In the preferred embodiment of both the first and second aspects of the invention, the outer layer of the resulting preformed polymeric composition, which is generally the most oxidized and least crosslinked and, thus, least wear resistant, is removed. For example, the bearing surface of the preformed polymeric composition may be fashioned from inside, e.g., by machining away the surface of the irradiated and thermally treated composition before or during fashioning into the final product, e.g., into an implant. Bearing surfaces are surfaces which are in moving contact with another, e.g., in a sliding, pivoting, or rotating relationship to one another.

Choices of Polymers

The polymers are generally polyester, poly(methylmethacrylate), nylon, polycarbonates, and polyhydrocarbons such as polyethylene, and polypropylene. High molecular weight (HMW) and ultra-high molecular weight (UHMW) polymers are preferred, such as HMW polyethylene (HMWPE), UHMW polyethylene (UHMWPE), and UHMW polypropylene. HMW polymers have molecular weights ranging from about $10^5$ grams per mole to just below $10^6$. UHMW polymers have molecular weights equal to or higher than $10^6$ grams per mole, preferably from $10^6$ to about $10^7$. The polymers are generally between about 400,000 grams per mole to about 10,000,000 and are preferably polyolefinic materials.

For implants, the preferred polymers are those that are wear resistant and have exceptional chemical resistance. UHMWPE is the most preferred polymer as it is known for these properties and is currently widely used to make acetabular cups for total hip prostheses and components of other joint replacements. Examples of UHMWPE are those having molecular weight ranging from about 1 to $8 \times 10^6$ grams per mole, examples of which are: GUR 4150 or 4050 (Hoechst-Celanese Corporation, League City, Tex.) with a weight average molecular weight of 5 to $6 \times 10^6$ grams per mole; GUR 4130 with a weight average molecular weight of 3 to $4 \times 10^6$; GUR 4120 or 4020 with a weight average molecular weight of 3 to $4 \times 10^6$; RCH 1000 (Hoechst-Celanese Corp.) with a weight average of molecular weight of $4 \times 10^6$ and HiFax 1900 of 2 to $4 \times 10^6$ (HiMont, Elkton, Md.). Historically, companies which make implants have used polyethylenes such as HIFAX 1900, GUR 4020, GUR 4120 and GUR 4150 for making acetabular cups.

Sterilization Methods

All polymeric products must be sterilized by a suitable method prior to implanting in the human body. For the formed crosslinked and thermally treated polymeric compositions (i.e., the final products) of the present invention, it is preferable that the products be sterilized by a non-radiation based method, such as ethylene oxide or gas plasma, in order not to induce additional crosslinking and/or oxidation of the previously treated preformed polymeric composition. Compared to radiation sterilization, a non-radiation sterilization method has a minor effect on the other important physical characteristics of the product.

Nevertheless, the method can be used in conjunction with radiation sterilization. If the final products are to be sterilized by an additional dose of radiation, it is preferable to take into account the effect of this additional radiation dose on the wear resistance and other properties of the polymer, in determining the optimum radiation dose used in the initial crosslinking. Furthermore, it is preferable that the radiation sterilization be done while the final product (e.g., in vivo implant) is packed in a suitable low-oxygen atmosphere (e.g., in partial vacuum, in an inert gas such as nitrogen, or with an oxygen scavenger included) in order to minimize oxidation of the surface layer of the final product during and after sterilization by irradiation.

The dose ranges in this application do not take into account radiation sterilization. If radiation sterilization is used, then the dose ranges may have to be adjusted. Such adjustment can be easily performed using the teachings herein. For example, if after comparing the dose-response curves for wear with those for other important physical or chemical properties, it is determined that the optimal total radiation dose is 8 Mrad, and it is intended to sterilize the polymer with 2.5 Mrad gamma radiation (the minimum industrial standard sterilization dose), then the initial radiation dose (before sterilization) should be 5.5 Mrad, such that the total dose (initial plus sterilization doses) will be 8 Mrad. These calculations are approximate, since the total crosslinking achieved will not be exactly equivalent to a single 8 Mrad dose.

Figure 3:
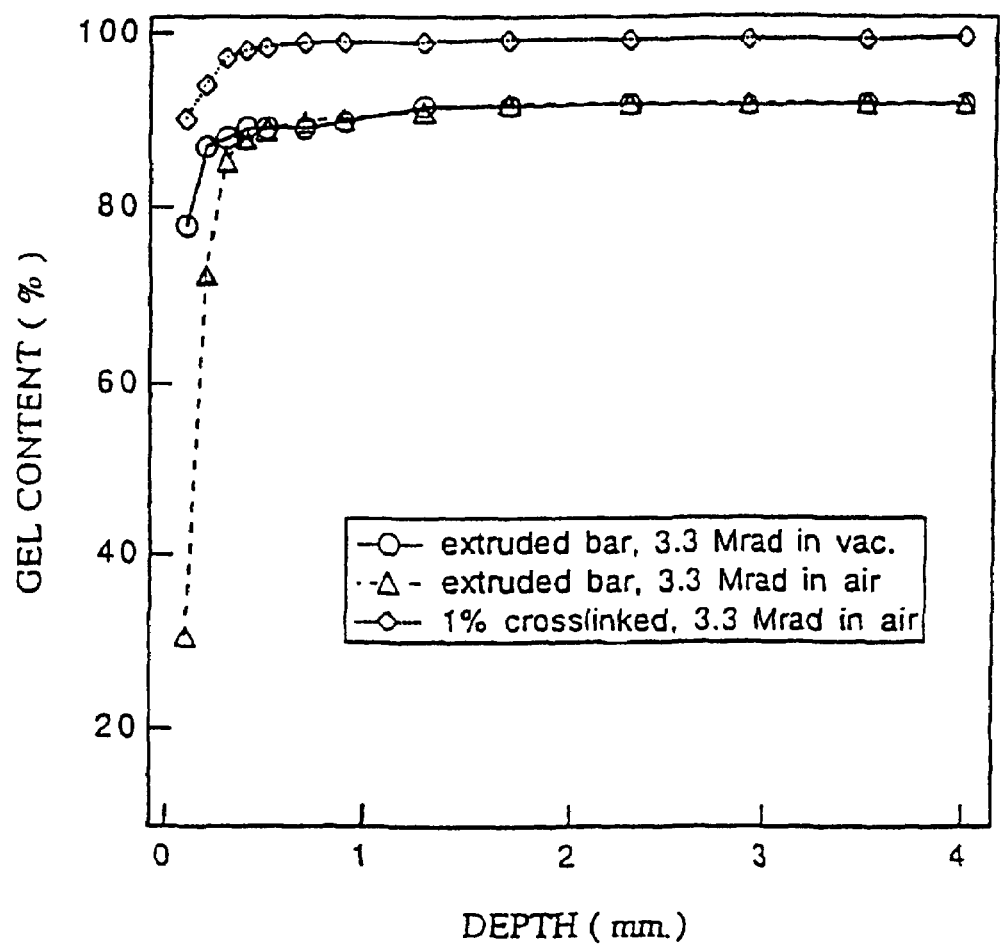
FIG. 3 presents the gel content vs. depth at indicated conditions for UHMWPE.

Nevertheless, the applicants have discovered that a high level of crosslinking in the surface layer of a polymer markedly reduces the degradative effects of surface oxidation, i.e., that would otherwise occur if a non-precrosslinked polymer were irradiated in the presence of oxygen (for example, see FIG. 3).

Methods for Characterizing the Polymers

The degree of crystallinity can be determined using methods known in the art, e.g. by differential scanning calorimetry (DSC), which is generally used to assess the crystallinity and melting behavior of a polymer. Wang, X. & Salovey, R., *J. App. Polymer Sci.*, 34:593-599 (1987).

Wide-angle X-ray scattering from the resulting polymer can also be used to further confirm the degree of crystallinity of the polymer, e.g. as described in Spruiell, J. E., & Clark, E. S., in "*Methods of Experimental-Physics*", L. Marton & C. Marton, Eds., Vol. 16, Part B, Academic Press, New York (1980). Other methods for determining the degree of crystallinity of the resulting polymer may include Fourier Transform Infared Spectroscopy {Painter, P. C. et al., "The Theory Of Vibrational Spectroscopy And Its Application To Polymeric Materials", John Wiley and Sons, New York, U.S.A. (1982)} and density measurement (ASTM D1505-68). Measurements of the gel content and swelling are generally used to characterize crosslink distributions in polymers, the procedure is described in Ding, Z. Y., et al., *J. Polymer Sci. Polymer Chem.*, 29:1035-38 (1990). FTIR can also be used to assess the depth profiles of oxidation as well as other chemical changes such as unsaturation {Nagy, E. V., & Li, S., "A Fourier transform infrared technique for the evaluation of polyethylene orthopaedic bearing materials", *Trans. Soc. for Biomaterials*, 13:109 (1990); Shinde, A. & Salovey, R., J. Polymer Sci., *Polym. Phys. Ed.*, 23:1681-1689 (1985)}.

Use of Crosslinked Polymers for Implants

Another aspect of the invention presents a process for making implants using the preformed polymeric composition of the present invention. The preformed polymeric composition may be shaped, e.g., machined, into the appropriate implants using methods known in the art. Preferably, the shaping process, such as machining, removes the oxidized surface of the composition.

Preformed Polymeric Compositions

The preformed polymeric compositions of the present invention can be used in any situation where a polymer, especially UHMWPE, is called for, but especially in situations where high wear resistance is desired. More particularly, these preformed polymeric compositions are useful for making implants.

Implants Made of Crosslinked Polymers

An important aspect of this invention presents implants that are made with the above preformed polymeric compositions or according to the methods presented herein. In particular, the implants are produced from preformed polymeric composition are UHMW polymers crosslinked by gamma radiation followed by remelting or annealing, removing the oxidized surface layer and then fabricating into a final shape. The preformed polymeric composition of the present invention can be used to make implants for various parts of the body, such as components of a joint in the body. For example, in the hip joints, the preformed polymeric composition can be used to make the acetabular cup, or the insert or liner of the cup, or trunnion bearings (e.g. between the modular head and the stem). In the knee joint, the preformed polymeric composition can be used to make the tibial plateau (femoro-tibial articulation), the patellar button (patello-femoral articulation), and trunnion or other bearing components, depending on the design of the artificial knee joint. In the ankle joint, the preformed polymeric composition can be used to make the talar surface (tibio-talar articulation) and other bearing components. In the elbow joint, the preformed polymeric composition can be used to make the radio-numeral joint, ulno-humeral joint, and other bearing components. In the shoulder joint, the pre-formed polymeric composition can be used to make the glenoro-humeral articulation, and other bearing components. In the spine, the preformed polymeric composition can be used to make intervertebral disk replacement and facet joint replacement. The preformed polymeric composition can also be made into temporo-mandibular joint (jaw) and finger joints. The above are by way of example, and are not meant to be limiting.

The following discusses the first and second aspects of the invention in more detail.

I. First Aspect of the Invention: Polymeric Compositions with Increased Wear Resistance The first aspect of the invention provides preformed polymeric compositions which are wear resistant and useful for making in viva implants. In this aspect, for polymers in general, and more preferably UHMW and HMW polymers, and most preferably UHMWPE and HMWPE, the irradiation dose is preferably from about 1 to about 100 Mrad, and more preferably, from about 5 to about 25 Mrad, and most preferably from about 5 to about 10 Mrad. This most preferable range is based on achieving what the inventors have determined to be a reasonable balance between improved wear resistance and minimal degradation of other important physical properties.

In vivo implants of the present invention, i.e., irradiated within the above dose ranges are expected to function in vivo without mechanical failure. The UHMWPE acetabular cups used by Oonishi et al. [in *Radiat. Phys. Chem.*, 39: 495-504 (1992)] were irradiated to 100 Mrad and functioned in vivo without reported mechanical failure after as long as 26 years of clinical use. Furthermore, it is surprising that, as shown in the EXAMPLES, acetabular cups from the preformed polymeric composition prepared according to the present invention, but irradiated to much less than 100 Mrad, exhibited much higher wear resistance than reported by Oonishi et al.

On the other hand, if a user is primarily concerned with reducing wear, and other physical properties are of secondary concern, then a higher dose than the above stipulated most preferable range (e.g., 5 to 10 Mrad) may be appropriate, or vice versa (as illustrated in the detailed examples in the following section). The optimum radiation dose is preferably based on the dose received at the level of the bearing surface in the final product. Gamma radiation is preferred.

The irradiated polymer is then preferably remelted at or above melting temperature of the irradiated polymer, e.g., in air. As used herein, the melting temperature of the crosslinked or irradiated polymer is identified from the peak of the melting endotherm as measured by DSC. Preferably, the remelting temperature is from about the melting temperature of the irradiated polymer to about 100° C. to about 160° C. above the melting temperature of the irradiated polymer; more preferably from about 40° C. to about 80° C. above the melting temperature of the irradiated polymer; and most preferably from about 1° C. to about 60° C. above the melting temperature of the irradiated polymer. For example, in the case of UHMWPE, the remelting temperature is preferably from about 136° C. to about 300° C., more preferably from about 136° C. to about 250° C., and most preferably from about 136° C. to about 200° C. Specific conditions for remelting are described in EXAMPLES 1 and 2, below.

Generally, in practice, the remelting temperature is inversely proportional to the remelting period. The polymer is preferably remelted over a period from about 1 hour to about 2 days, more preferably from about 1 hour to about 1 day, and most preferably from about 2 hours to about 12 hours.

Since, depending on the time and temperature applied, annealing can produce less of an effect than remelting on physical properties such as crystallinity, yield strength and ultimate strength, annealing may be used in place of remelting as a means for reducing the free radicals remaining in the polymer after irradiation crosslinking, in order to maintain these physical properties within limits required by the user. Thermal treatment, such as remelting or annealing, removes free radicals and thereby improves long term wear resistance of the polymer. On the other hand, annealing is slower and thus takes longer than remelting, making it likely to be more expensive in industrial applications.

The annealing temperature is preferably from about room temperature to below the melting temperature of the irradiated polymer; more preferably from about 90° C. to about 1° C. below the melting temperature of the irradiated polymer; and most preferably from about 60° C. to about 1° C. below the melting temperature of the irradiated polymer. For example, UHMWPE may be annealed at a temperature from about 25° C. to about 135° C., preferably from about 50° C. to about 135° C., and more preferably from about 80° C. to about 135° C. The annealing period is preferably from about 2 hours to about 7 days, and more preferably from about 7 hours to about 5 days, and most preferably from about 10 hours to about 2 days.

Instead of using the above range of radiation dose as a criterion, the appropriate amount of crosslinking may be determined based on the degree of swelling, gel content, or molecular weight between crosslinks after thermal treatment. This alternative is based on the applicant's findings (detailed below) that acetabular cups made from UHMWPE falling within a preferred range of these physical parameters have reduced or non-detectable wear. The ranges of these physical parameters include one or more of the following: a degree of swelling of between about 1.7 to about 5.3; molecular weight between crosslinks of between about 400 to about 8400 g/mol; and a gel content of between about 95% to about 99%. A preferred polymer or final product has one or more, and preferably all, of the above characteristics. These parameters can also be used as starting points in the second aspect of the invention (as illustrated by the flowchart, discussed below) for determining the desired radiation dose to balance the improvement in wear resistance with other desired physical or chemical properties, such as polymer strength or stiffness.

After crosslinking and thermal treatment, preferably, the most oxidized surface of the preformed polymeric composition is removed. The depth profiles of oxidation of the preformed polymeric composition can be determined by methods known in the art, such as FTIR, described above and in EXAMPLES 3 and 6. In general, to remove the most oxidized surface, preferably a minimum of about 0.5 mm to 1.0 mm of the surface of preformed polymeric composition which is exposed to air is removed, e.g. by machining, before or while fashioning the preformed polymeric composition into the final product.

I.(A) Further Examples of the First Aspect of the Invention

As noted above, the most preferable range of dose for crosslinking radiation (i.e., from 5 to 10 Mad) was based on achieving what the inventors have determined to be a reasonable balance between improved wear resistance and minimal degradation of other important physical properties. The following examples illustrate applications of the present invention with alternative criteria for the optimal dose. These examples use in vivo implants as non-limiting examples of the products, and UHMWPE or HMWPE bar or block as a non-limiting example of a starting material.

In the first example, the user desires to achieve a minimum wear rate of the in vivo implant made from the UHMWPE and HMWPE, and the other physical or chemical properties are important but of lesser concern. In such a case, the user may choose to irradiate the UHMWPE and HMWPE bar or block between about 15 Mrad to about 20 Mrad (as shown by so FIG. 22). As discussed in the section "II (b) Application of the Flowchart", below,. GUR 4150 is representative of UHM-WPE and HMWPE. The irradiated UHMWPE or HMWPE bar or block is further remelted or annealed at a temperature and time described in "I. First Aspect of the Invention: Polymeric Compositions with Increased Wear Resistance", above.

In a second example, the user may wish to produce an UHMWPE which is as wear resistant as possible while meeting the tensile strength at break (ultimate), tensile strength at yield, and elongation at break criteria of the standard specified by the American Society for Testing and Materials F-648 standard (hereinafter referred to as "ASTM F648") for UHM-WPE for in vivo use. The information about this standard can be found in a current issue of the *Annual Book of ASTM Standards, Medical Devices and Services*, "Standard Specification for Ultra-High-Molecular-Weight Polyethylene Powder and Fabricated Form for Surgical Implants", American Society for Testing and Materials. The method of the second aspect of the present invention (as illustrated by the flowchart) may be used to adjust the crosslinking and thermal treatment parameters to meet any current ASTM F648 criteria.

For example, to meet the 1996 ASTM F648 (F648-96) criteria for Type 1 or 2 UHMWPE, the UHMWPE must have: a tensile strength at break (ultimate) of at least 35 MPa (for Type 1) and 27 MPa (for Type 2) at 23° C. and 5.08 cm/min; a tensile strength at yield of at least 21 MPa (Type 1) and 19 MPa (for Type 2) at 23° C., and 5.08 cm/min; and elongation at break of at least 300% at 5.08 cm/min. The test conditions are described in ASTM D638, Type IV (*Annual Book of ASTM Standards*, American Society for Testing and Materials). Alternatively, to meet the 1996 ASTM F648 criteria for Type 3 UHMWPE, the UHMWPE must have: a tensile strength at break (ultimate) of at least 27 MPa at 23° C. and 5.08 cm/min; a tensile strength at yield of at least 19 MPa at 23° C., and 5.08 cm/min; and elongation at break of at least 250% at 5.08 cm/min.

The plots of mechanical properties vs irradiation dose for GUR 4150 (which is representative of Type 2 UHMWPE) (FIGS. 25-27) show that, for all of the radiation doses between 5 to 25 Mrad, the above ASTM F648 criteria for Types 2 UHMWPE are fulfilled except for the elongation at break, which crosses the 300 limit at about 6 Mrad. Thus, if the ASTM F648 criteria are to be met for Types 2 UHMWPE, the maximum (i.e., the most preferred) gamma radiation dose is about 6 Mrad. As illustrated in the second aspect of the invention (following section), the corresponding curves of wear and other physical properties vs. crosslinking dose could be used to determine the preferred dose range for other Types of UHMWPE or for other polymers in general.

II. Second Aspect of the Invention: Method for Optimizing Wear Resistance and Desirable Physical and/or Chemical Characteristics of a Polymeric Composition The second aspect of the invention uses the findings in this patent application (including those presented in the "EXAMPLES" section, below) to construct a method which allows one skilled in the art, to systematically identify the conditions necessary to routinely produce a polymer with an optimal balance of wear resistance and physical and/or chemical properties, with minimal additional testing and minimal trial and error. In one embodiment of this aspect of the invention, the optimizing method can be schematically illustrated in a flowchart. Once the optimal conditions have been determined by this method, the polymer can then be subjected to these conditions for processing.

The present invention is based in part, on the discovery that wear rate decreases with increasing radiation dose, and there is a maximum dose above which there is little or no additional improvement in wear, but higher doses might degrade other important physical and/or chemical properties of the polymer, such as yield or ultimate strength, elongation to failure, impact strength or fatigue resistance, as well as increasing the susceptibility to oxidation. Oxidation, in turn, is known to adversely affect one or more of these physical properties, and was shown to occur in the examples below for UHMWPE crosslinked at a dose averaging about 28 Mrad if there had been no thermal treatment. Consequently, a polymer irradiated at a high radiation dose may exhibit improved wear resistance, but its other physical or chemical properties may fall outside of desirable or allowable limits, such as those specified by ASTM F648 for UHMWPE for in vivo use.

The method is also based in part on the discovery that, while other important physical properties (such as crystallinity or elongation to break) may be markedly affected by the amount of thermal treatment (e.g., remelting or annealing) applied to the polymer after irradiation crosslinking, the wear resistance is not markedly affected. This latter discovery permits reducing the amount of additional testing required by the user in order to identify the crosslinking dose which will provide the user's desired balance among wear resistance and other physical properties. This method is useful, e.g., in the case where performed polymeric composition made of UHMWPE is used for making in vivo implants, such as acetabular cups.

II (a) Summary of the Steps of the Optimization Method

Figure 23A:
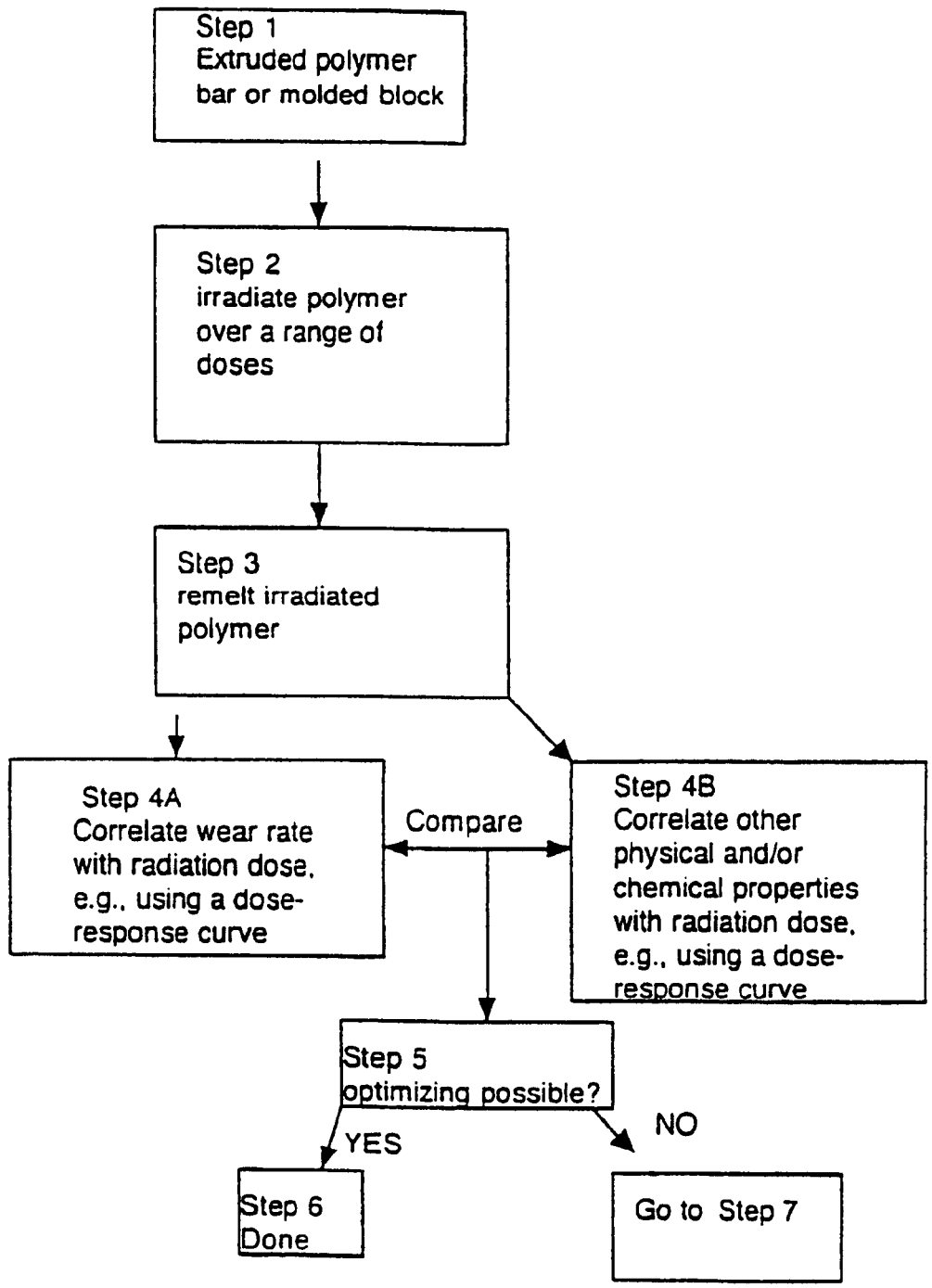
FIGS. 23A and 23B present the flowchart illustrating the optimization method of the present invention.
Figure 23B:
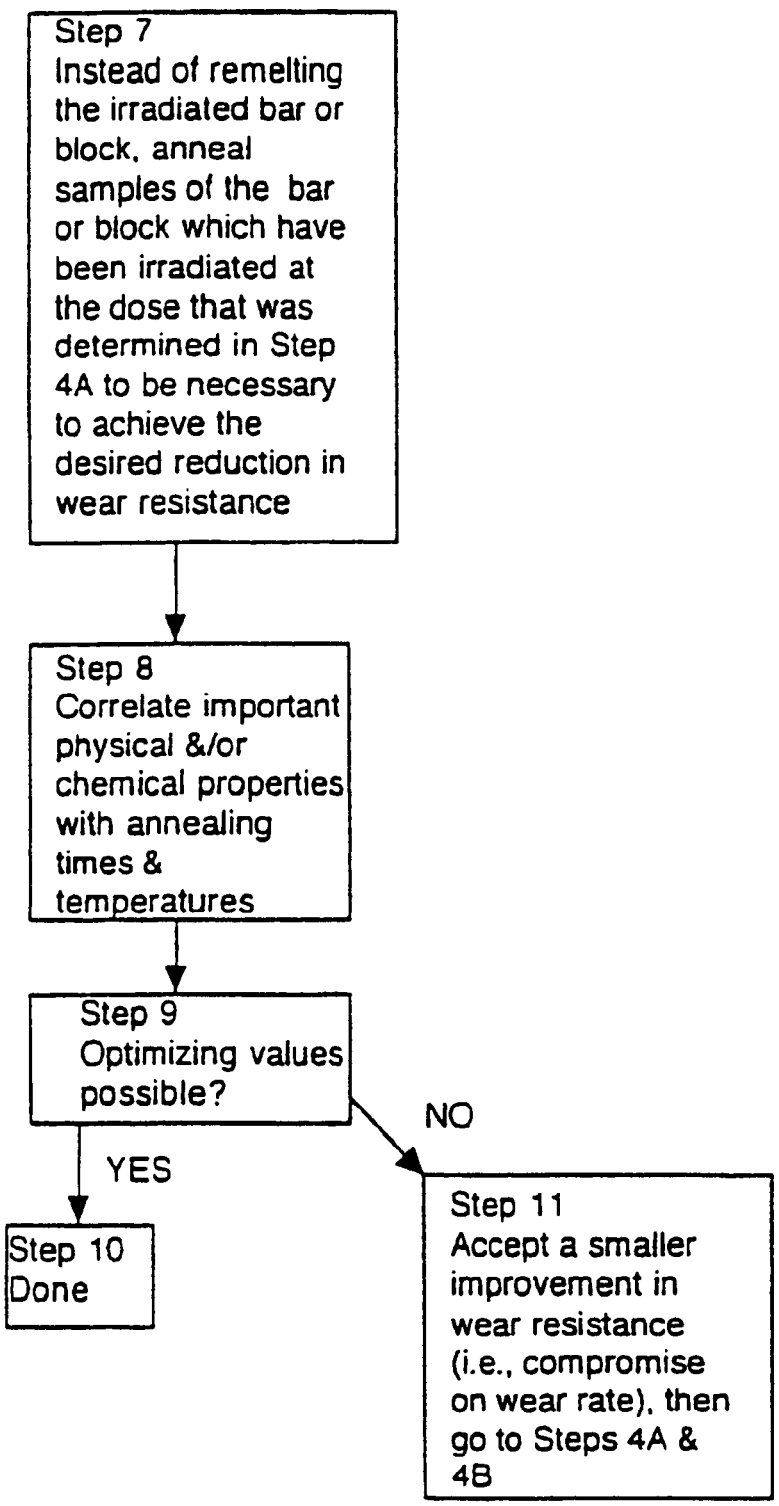

Thus, the second aspect of the present invention provides a systematic method for optimizing the balance among wear resistance and other desired physical and/or chemical characteristics of a polymer. The steps in this method are summarized in the non-limiting example of the flowchart of FIGS. 23A and 23B. In the flowchart and the following discussion, for ease of discussion, irradiation is used as an example of a crosslinking method, and implant is used as an example of the product that is made from the polymer. However, as discussed elsewhere in this application, other crosslinking methods and products may be used.

Step 1: The process typically begins with the polymer in solid form, such as an extruded bar or block.

Step 2: The bar is irradiated over a range of doses up to the maximum that is likely to produce a material with the desired wear resistance and physical and/or chemical properties. This irradiation may be done, for example, in the case of gamma radiation by means of a cobalt 60 gamma radiation facility as is presently used for industrial-scale sterilization of implants.

Figure 2:
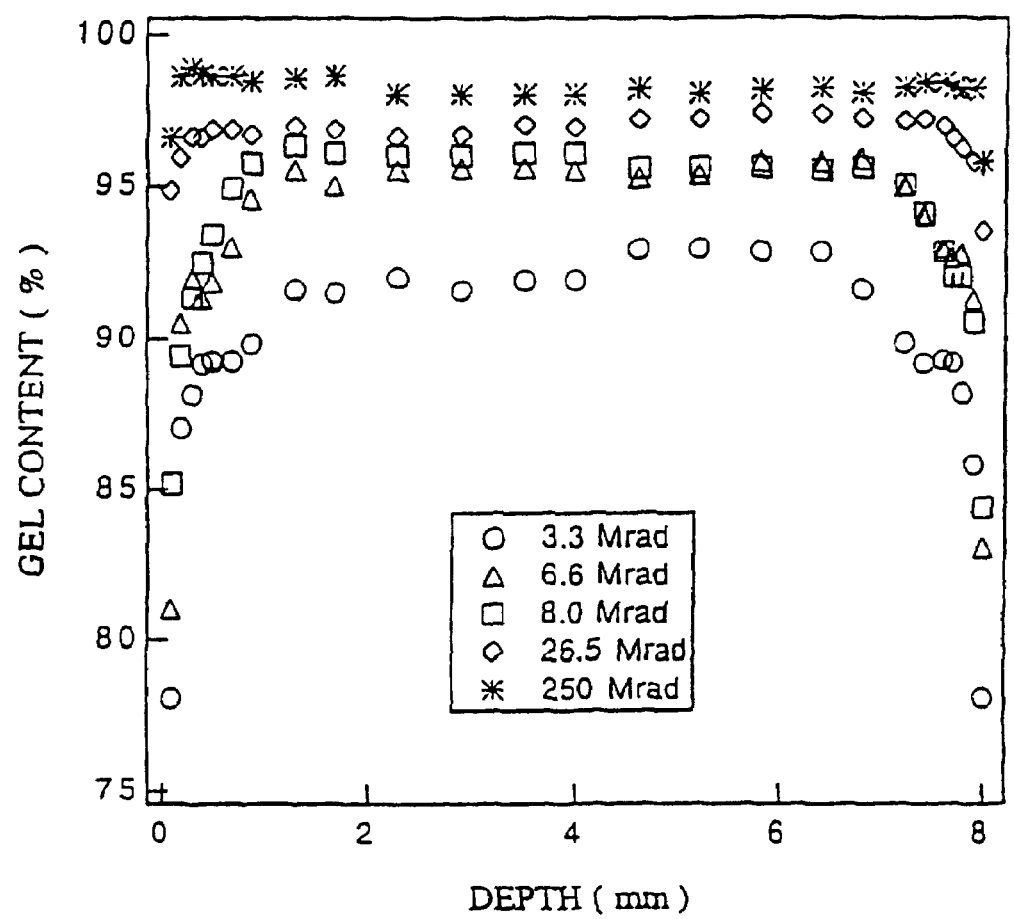
FIG. 2 presents the gel content vs. depth at indicated doses for UHMWPE that was irradiated in a vacuum (i.e., a low-oxygen atmosphere).
Figure 5:
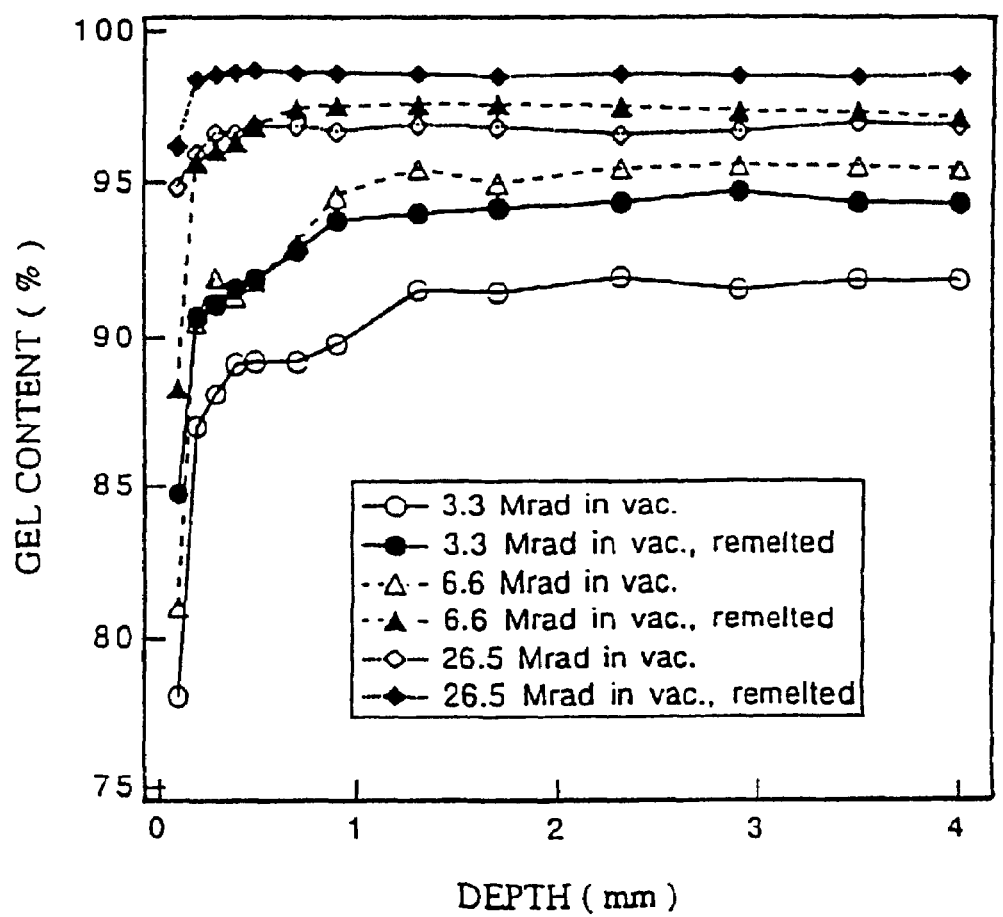
FIG. 5 presents the gel content vs. depth at indicated conditions for UHMWPE.
Figure 24:
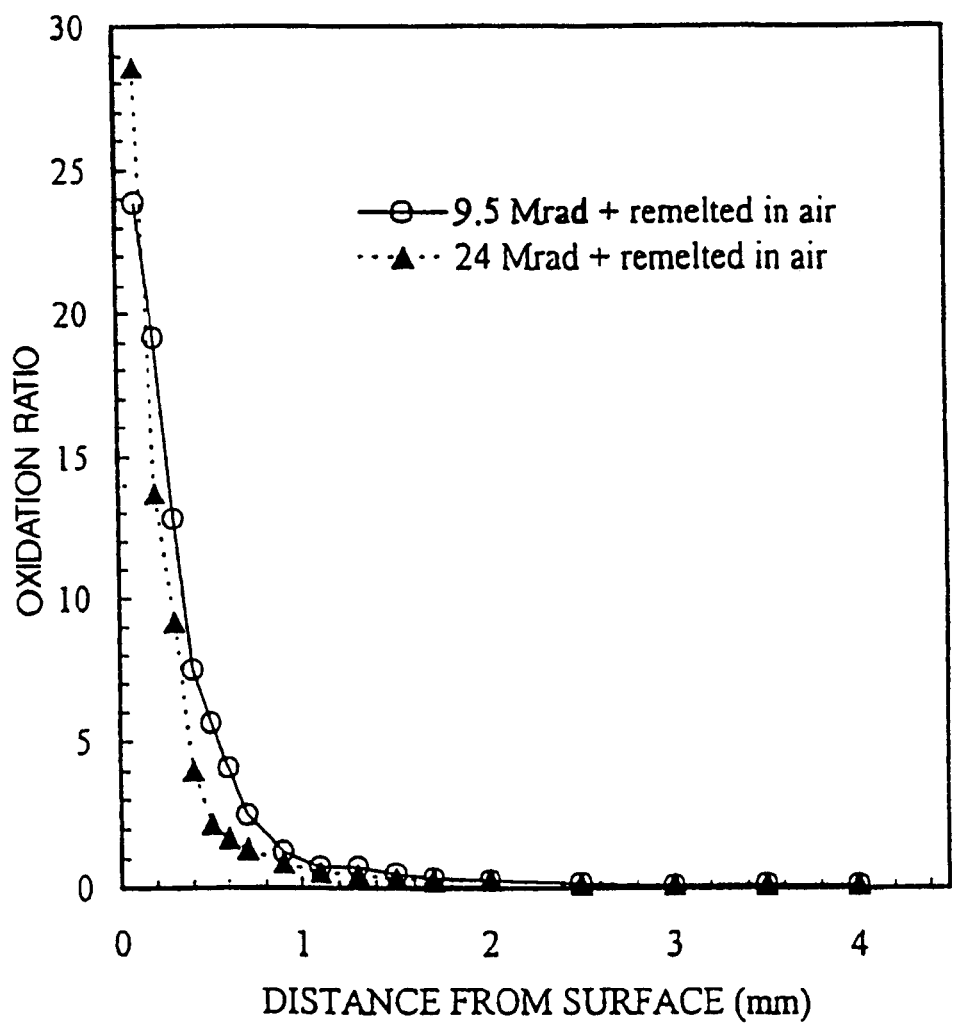
FIG. 24 graphically shows the oxidation profiles for irradiated and remelted UHMWPE as a function of depth from the UHMWPE bar surface.

Step 3: The irradiated bars are then remelted. Applicants found that remelting of an irradiated polymer would substantially reduce the free radicals produced during irradiation, thus minimizing long-term oxidation and chain scission. By improving the polymeric composition's resistance to long-term oxidation, remelting also improves the polymeric composition's long-term resistance to wear. For further discussion of the subject, see EXAMPLES 2, 3, and 4, below Although the bar may be contained in a low-oxygen atmosphere during the remelting, this may not be essential since, even if the bar is remelted in ambient air, the resultant oxidation may affect only the surface layer of the polymer (e.g. in the following EXAMPLE section, FIGS. 2, 5, and 24, show oxidation extending to about 1 mm deep). In the preferred embodiment of the invention, the oxidized surface layer of the preformed polymeric composition will be removed, e.g., during subsequent machining of the products out of the treated bar.

Step 4A The radiation dose is correlated with the wear resistance of the products made from the irradiated remelted polymeric composition, as determined in a wear test that adequately simulates the wear conditions of the products. For example, if the polymeric composition will be made into an implant, then the wear test should preferably adequately simulate the wear conditions of such implants in vivo. The correlation may be arrived at by plotting a dose-response curve for irradiation dose vs. wear.

Step 4B: Similarly, the radiation dose is correlated with each of the physical and/or chemical properties that may be markedly affected by the radiation dose and that might, in turn, substantially affect the performance of the implant in vivo, both for non-remelted and remelted polymer. Again, the correlation may be arrived at by plotting a dose-response curve for irradiation dose vs. each of these physical and/or chemical properties.

The user does not have to do dose vs. properties for each property that might be affected, but only those properties that are considered important for the proper functioning of the implant in vivo. Which of these properties are important for the intended application, and the limiting values of these properties, may vary for different polymeric compositions and for different types of applications (e.g., hip prostheses compared to knee prostheses) and must, therefore, be established by the user before applying the flowchart.

Step 5 is the first attempt at optimization. The user may first decide on the desired amount of improvement in the wear resistance, i.e., the maximum wear rate that is permissible for the user's application. The dose-response curve for wear (Step 4A) then shows the minimum radiation dose necessary to provide this amount of improvement in wear resistance.

Similarly, the dose response curves for the other physical or chemical properties deemed critical or important (Step 4B) provide the values of these properties corresponding to the specific radiation dose identified in Step 4A as being necessary to provide the desired improvement in wear resistance. If each of these other physical or chemical properties are within allowable limits for the crosslinked and remelted polymer, then an optimal method has been identified (Step 6). In other words, the implant can be made by irradiating the solid polymer bar, remelting the bar and machining out the implant; the entire process being conducted such that the resulting implant has received the optimal dose at its bearing surface.

Alternatively, the user may first decide on critical values for one or more properties, such as ultimate tensile strength, fatigue strength, etc., and then check the corresponding dose response curves for the remelted polymer for the maximum allowable dose, and then check the wear vs. dose curve to determine whether this dose gives sufficient improvement in wear (i.e., the user does not necessarily have to begin by choosing the desired amount of improvement in wear).

However, if not enough improvement in wear will be obtained while keeping these other chemical and physical properties within allowable limits, or conversely, if the dose required for the desired wear improvement causes one or more of these properties to be out of allowable limits, then the user can use a lower radiation dose (i.e., accept a higher wear rate) if he wishes to remelt the materials or, alternatively, annealing may be substituted for remelting (Step 7). For a crosslinked material, annealing is less efficient than remelting in removing free radicals, but may cause less of a reduction in other important physical properties.

Whether annealing is a practical option will be apparent from the dose-response curves for the non-remelted and remelted polymers. That is, if the desired value of the property in question falls between the two curves (see for example, FIGS. 25 and 26), then a polymer with the desired limiting value may be produced by an annealing process with an appropriate time/temperature combination.

It is not necessary to generate additional wear dose-response curves for each of the many possible combinations of annealing time and temperature. It is expected that the radiation dose necessary to produce the desired reduction in wear that is determined from the wear dose-response curve for remelted polymer in Step 4A, will also apply to an annealed polymer produced in Step 7.

Step 7: Anneal samples of a bar or block which have been irradiated to that dose that was identified in Step 4A as being necessary to provide the required improvement in wear resistance, at various time/temperature combinations, to produce a polymer with the critical properties between those for non-remelted and remelted materials.

Step 8: The physical or chemical propert(ies) of interest of the irradiated and annealed samples of the polymer are correlated with annealing times and temperatures.

Step 9: Using ultimate tensile strength as an example of the physical characteristic of interest, depending on the resultant curve for annealing time and/or temperature vs. ultimate strength, the radiation dose required to achieve the desired wear resistance identified in Step 4A (above) should produce a polymer with an ultimate strength within allowable limits.

Similar consideration should be given to each of the other important physical and/or chemical properties by generation of individual curves of these properties versus annealing time and/or temperature. If each of these properties is within allowable limits at a particular annealing time and temperature combination, then a suitable method has been identified (Step 10).

If an annealing process cannot be identified that maintains the properties within allowable limits, then the user may choose to accept a lower radiation dose (Step 11), i.e., to accept less of an improvement in wear resistance. However, if a lower radiation dose (and, therefore, a greater wear rate) is acceptable, then the corresponding physical and chemical properties should again be checked for the remelted polymer (using the correlation arrived earlier in Step 4B), since these may be within limits at the lower radiation dose.

If the properties are within limits for the remelted polymer at the lower radiation dose, then remelting may be used instead of annealing to produce a polymer with the desired improvement in wear resistance (Step 6). If not, then the user should proceed with annealing as before (Steps 7 through 10 or 11) but at this lower radiation dose.

The user may wish to progressively reduce the required amount of radiation crosslinking (i.e., to accept still higher wear rate) until a dose is identified for which all of the other properties deemed essential are within the user's required limits. The resultant dose represents the maximum improvement in wear resistance obtainable within the user's criteria.

II(b) Example Applications of the Flowchart

As starting points for the flowchart, the ranges for radiation doses, remelting and annealing temperatures and times described in section "I. First Aspect of the Invention: Polymeric Compositions with Increased Wear Resistance" and "I (A) Further Examples of the First Aspect of the Invention", above, can be used, with regard to polymers in general, UHMW and HMW polymers in particular, and HMWPE and UHMWPE especially.

For ease of discussion, the following examples illustrate the application of the flowchart using UHMWPE (which also behaves similar to HMWPE) as an example of a polymer and an acetabular cup as an example of an implant. GUR 4150 is representative of such a class of UHMWPE. Similarly, the description uses gamma radiation as an example for crosslinking the polymer. These examples are meant to illustrate and not meant to limit the invention.

The method described by the flowchart is applicable to other polymers, implants or other products made from such polymers, and crosslinking methods (examples of which are described elsewhere in this application), and methods for making an implant or product out of the preformed polymeric composition.

From the data provided by the EXAMPLES (following sections) a number of generalities were discovered that allowed simplification of the use of the flowchart, i.e., to minimize the amount of additional testing that would be required of a user wishing to apply the method to other polymers, or to the GUR4150 of the EXAMPLES but with various optimization criteria.

To establish the critical curve for the reduced in vivo wear (Step 4A), the UHMWPE bar or block is preferably irradiated in Step 2 and remelted in Step 3, in a manner and to a dose and temperature and time as described for UHMWPE in the section, "I. First Aspect of the Invention: Polymeric Compositions with Increased wear Resistance" and "I (A) Further Examples of the First Aspect of the Invention ", above.

In step 4A, acetabular cups are machined out of the irradiated bar and wear tested under conditions suitably representative of the intended in vivo application (e.g., by the method described in the EXAMPLES section below) to establish a wear vs. radiation dose response curve for the specific polymer. EXAMPLE 5 and FIG. 22 show a wear dose-response curve for gamma irradiated GUR 4150 UHMWPE.

Applicants discovered that it is not necessary to generate additional wear dose-response curves for each of the many possible combinations of annealing time and temperature. This follows from the results of EXAMPLE 2. Since annealing is done at a lower temperature than remelting and, therefore, has a less marked effect on physical properties in general, it can be expected that annealing will have even less of an effect on the wear resistance than remelting.

Another important aspect of the invention is the discovery that wear resistance of GUR 4150 was not markedly affected by remelting and, therefore, it is also not likely to be markedly affected by annealing time and temperature. Therefore, it is expected that the radiation dose necessary to produce the desired reduction in wear that is determined from the wear dose-response curve for remelted polymer in Step 4A, will also apply to an annealed polymer produced in Step 7. Therefore, while the user needs to do his own tests to establish tensile strength vs dose etc., he can rely on the wear vs dose curve developed for the remelted material, rather than running an additional set of wear curves for each annealing condition. This represents a considerable saving in experimental costs, since the tensile strength tests typically may be completed in a few days (using common tensile test apparatus), but the tests of wear vs dose require months to complete (and require highly specialized equipment and techniques available on only a handful of laboratories in the world).

Figure 22:
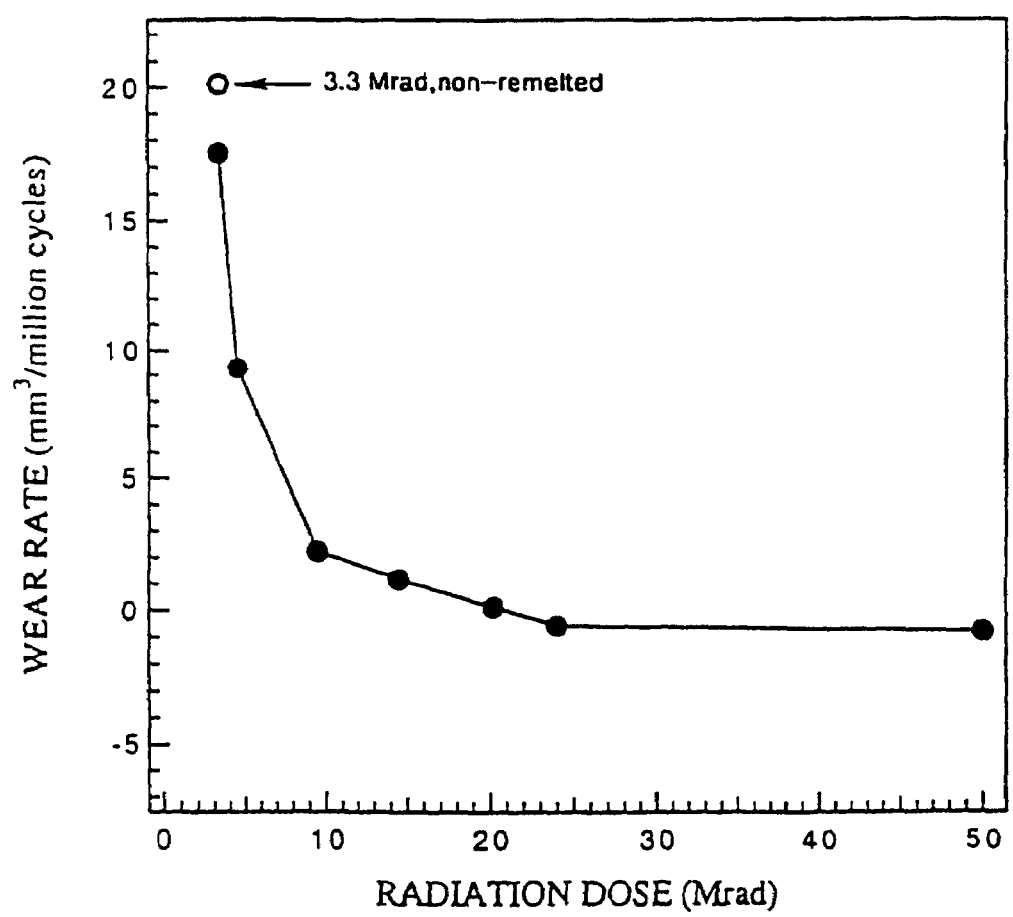
FIG. 22 shows the average wear rate versus radiation dose of non-remelted and remelted cups.

Furthermore, if the user is working with GUR 4150, he can use the dose vs wear curve of FIG. 22 (as well as the plots of other mechanical properties, FIGS. 25-27) without needing to run any wear or tensile tests. Finally, if he is working with another grade of UHMW polyethylene, he can probably use FIG. 22, since other tests have shown that the wear resistances of these materials are very similar to GUR 4150 for a given sterilization treatment. At the least, FIG. 22 establishes the range on which the user may focus his wear vs. dose experiments for other grades of UHMW polyethylene, to minimize the testing necessary to identify the optimum dose.

For other polymers, comparable wear tests at each end of the range of interest for radiation dose could be applied to verify whether remelting or annealing also does not markedly affect their wear resistance. Nevertheless, GUR 4150 is representative of UHMWPEs, especially those useful for implants, in its physical and chemical properties, and applicants have observed that other UHMWPEs, of different molecular weights and with or without calcium stearate, such as GUR 1020 (calcium stearate free, lower molecular weight grade) behaved similarly to GUR 4150 in their wear resistance after irradiation sterilization in air. McKellop, H. et al., *Trans. Society for Biomaterials, Vol.* 20, pg. 43 (1997).

Further, it has been observed that, although the starting physical properties of HMWPE are different from those of UHMWPE, these differences will be substantially reduced after sufficient crosslinking. For example, they are almost equal after electron beam irradiation treatment to 300 kGy (30 Mrad), for properties like gel content, swelling and strength. Streicher, R. M., *Beta-Gamma* 1/89: 34-43, at p. 42, right col., fourth full paragraph. Even the wear properties were the same, after the differences in the molecular arrangement between HMWPE and UHMWPE were offset by the irradiation procedure. Thus, it is predicted that the findings based on GUR 4150 and the above discussion would be applicable to polymers in general, and to UHMW and HMV polymers, in particular, and especially HMWPE and UHMPE. Thus, the radiation, remelting and annealing ranges found for GUR 4150 can be applied to polymers in general, and more preferably to HMW and UHMW polymers, and most preferably to HMWPE and UHMWPE; and these ranges can be used at the very least, as starting points in the flowchart for determining the specific ranges for other polymers, and the data in the "EXAMPLES" section below will facilitate the user in arriving at the proper conditions for GUR 4150, ASTM F648 Type 2 UHMWPE, and UHMWPE and HMWPE in general.

The following examples illustrate the use of these generalities in conjunction with the flowchart. In the first example, if the user is working with GUR 4150, or an UHMWPE that satisfies ASTM F648 Type 2 criteria in general, then, based on FIGS. 25-27, only the elongation will fall below the ASTM limit (i.e., 300%) over the dose range of interest, i.e., 0 to 25 Mrad, and this occurs at about 6 Mrad. Thus, the maximum allowable dose is 6 Mrad and, from the wear vs dose plot (FIG. 22), it can be seen that a 6 Mrad dose will provide a wear rate of about 7 to 8 mm$^3$ per million cycles. This is about a 78% or more reduction over the 33.1 mm$^3$ per million cycles shown for non-remelted polyethene gamma irradiated to 3.1 Mrad in air. If this reduction in wear rate is sufficient for the user's purpose, then his goal is achieved. Note however, that the elongation vs dose plot (FIG. 27) shows virtually the same behavior whether the polyethylene is remelted or not, so if the above 78% reduction is not sufficient for the user's purpose, then the user would have no choice but to increase the radiation dose, as annealing is also not likely to affect the elongation to break, for the reasons discussed above.

Figure 25:
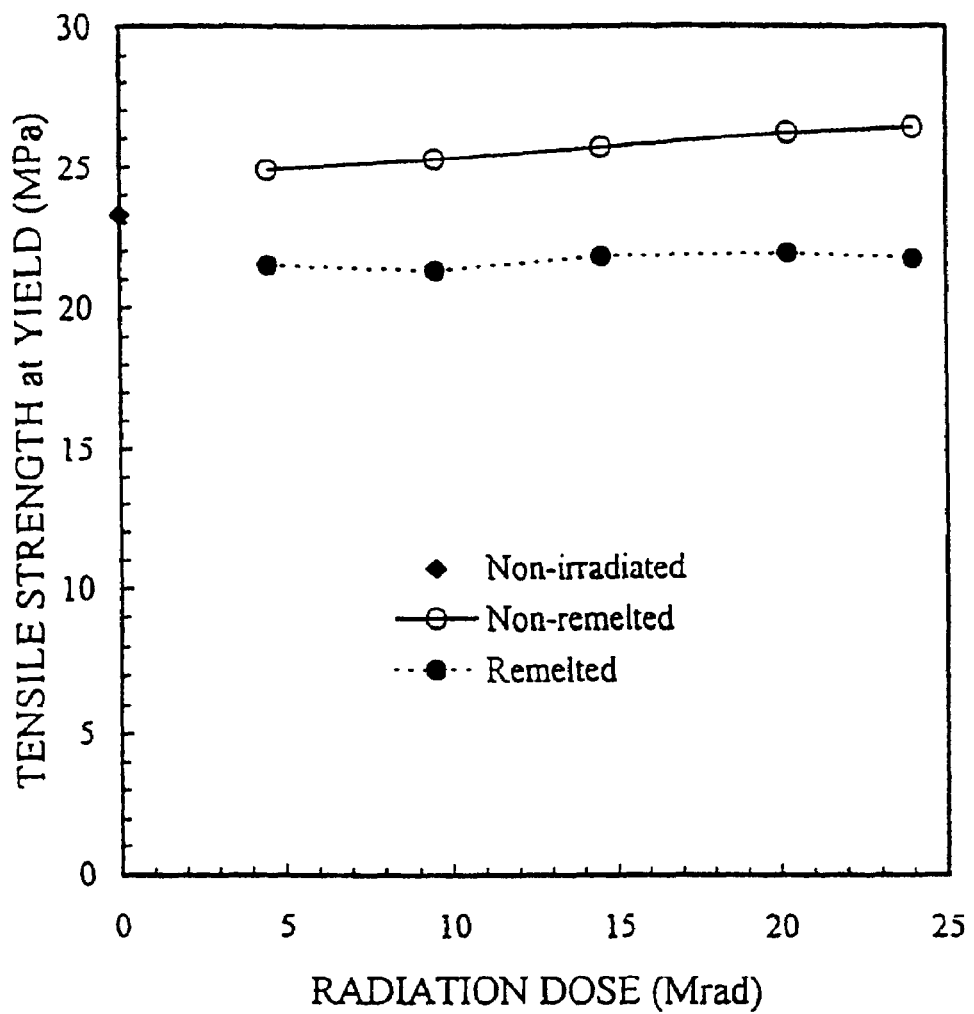
FIG. 25 graphically shows the tensile strength at yield versus radiation dose of irradiated UHMWPE with or without remelting, and non-irradiated and not remelted UHMWPE.
Figure 26:
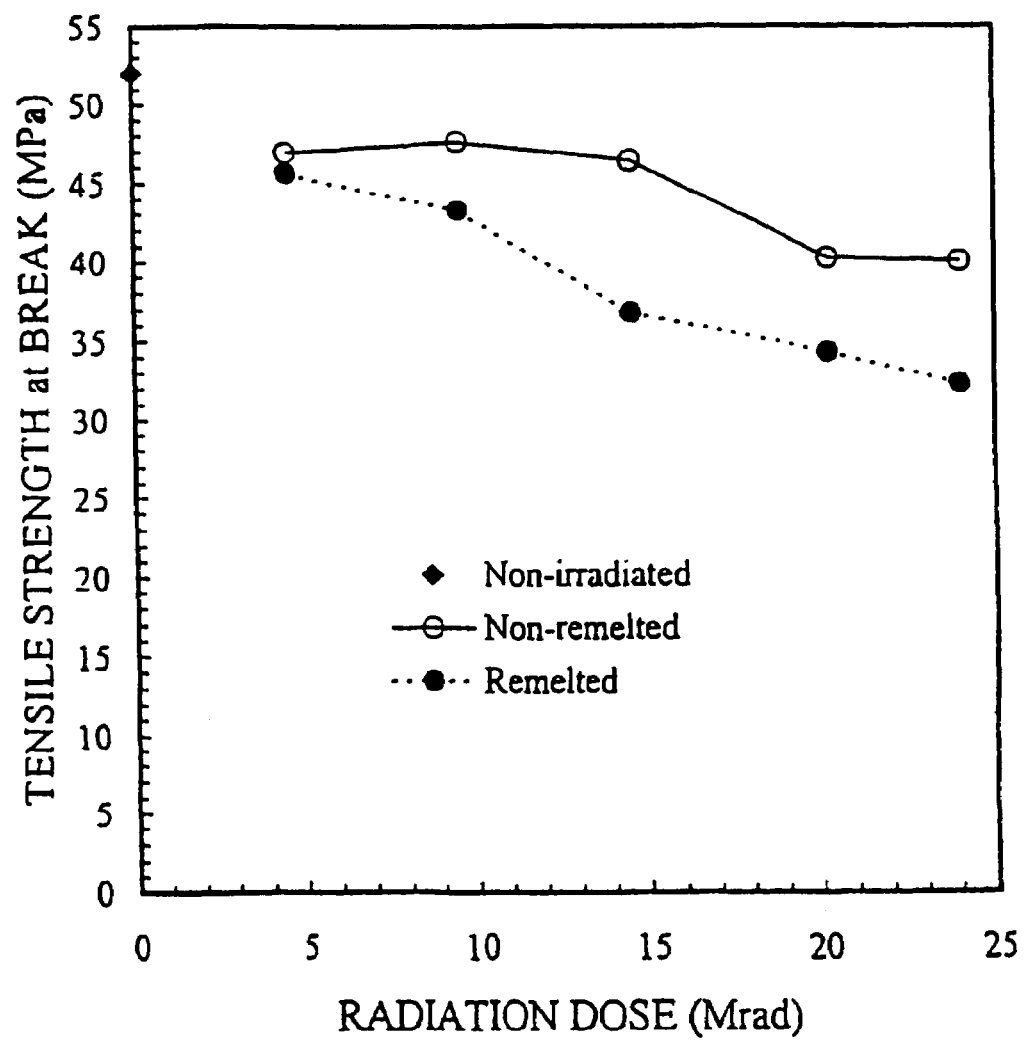
FIG. 26 graphically shows the tensile strength at break versus radiation dose of irradiated UHMWPE with or without remelting, and non-irradiated and not remelted UMMWPE.

In a second example, a user requires a lower limit on tensile strength at break at 40 MPa, and wishes to produce a material with wear no more than 1 mm$^3$ per million cycles. The wear vs dose curve (FIG. 22) shows that a dose of about 15 Mrad is required to produce a polyethylene with the desired amount of wear resistance. However, the tensile strength at fracture vs dose curve shows that the tensile strength at 15 Mrad for a remelted material is about 36 Mpa. Since this is below the user's acceptable limit of 40 Mpa, he can either use a smaller radiation dose and, therefore, accept a smaller improvement in wear rate (i.e., if he wishes to remelt his material) or he can try annealing instead of remelting since, depending on the time/temperature combination used, annealing can be expected to produce a polymer with a value of tensile strength between the limits indicated by the curves for non-remelted and remelted polymer (FIGS. 25 and 26). As shown on these figures, the tensile strength at 15 Mrad for a non-remelted material is about 46 Mpa, well above the user's limit of 40. So, with minimal trial and error, the user can identify an annealing time and temperature that, when applied to a polyethylene that has been exposed to 15 Mrad radiation, has a tensile strength of the required 40 Mpa. Again, based on the wear test results, the user knows that he does not have to re-do the wear vs dose curve for all of the various annealing treatments he tries, in order to identify the dose necessary to produce the desired improvement in wear resistance.

Having described the invention, the following examples are presented to illustrate and support the invention, and are not to be construed as limiting the scope of the invention.

EXAMPLES

The nominal dose of radiation applied to implants at a commercial radiation facility typically varies within a range. Therefore, in the following examples, the average gamma radiation doses are given, such as average gamma radiation doses of 3.3, 26.5, and 28 Mrad. The average of 3.3 Mrad was arrived at by averaging the minimum and maximum doses, e.g., a minimum of 3.28 and a maximum of 3.45 Mrad. Similarly, for example, the average of 26.5 was based on averaging a minimum of 25.14 and a maximum of 27.70 Mrad; and the average of 28 was based on averaging a minimum of 26.01 and a maximum of 30.30 Mrad.

Example 1

Effect of Radiation Atmosphere and Dose on the Physical Properties of UHMWPE Experimental Details Commercial-grade UHMWPE extruded bars (GUR 4150, Poly Hi Solidur), with a weight average molecular weight of 5-6×10$^6$, were used as received. The 8 mm thick specimens were cut from the bars and irradiated with gamma-rays at room temperature either in ambient air or in a vacuum chamber at SteriGenics International (Tustin, Calif.) to average doses ranging from 3.3 to 250 Mrad. Radiation was delivered at a dose rate of 0.2 Mrad/hr. For 250 Mrad, the dose rate was 4 Mrad/hr. Cobalt-60 was used as a source of gamma radiation. A subset of the 8 mm thick specimens that had been irradiated in vacuum was remelted in a vacuum oven by heating from room temperature to 145° C. slowly (at about 0.3° C./min.) and maintaining at. 145° C. for one hour. After remelting, the specimens were slowly cooled to room temperature.

The physical properties of the disk specimens before and after irradiation and remelting were characterized by DSC, gel content analysis and FTIR.

Gel Content Analysis

The gel content of each material was analyzed as a function of depth from the surface. 100 µm thick sections (about 50 mg) were microtomed across the specimen. Extraction of the sol-fraction was performed by boiling in p-xylene for 24 hours, with 0.5 wt % of antioxidant (2,6-di-t-butyl-4-methyl phenol) added to prevent oxidation. For highly oxidized sections from the surface layer, which tended to break up during boiling, the specimens were wrapped in PTFE membrane filter (0.5 µm pore size) to avoid loss of gel. After extraction, the specimens were de-swollen in acetone and dried at 60° C. in a vacuum oven to constant weight. The gel fraction was determined from the ratio of the weight of the dried-extracted material to that of the dry non-extracted material.

Differential Scanning Calorimetry (DSC)

For DSC measurements, samples were cored and microtomed into 200 µm thick sections across the depth. Specimens (~4 mg) were heated from 50° C. at 10° C./min in a differential scanning calorimeter (Perkin-Elmer DSC-4) to 170° C. The melting temperature was identified from the peak of the melting endotherm. Indium was used for calibration of the temperature and heat of fusion. The heat of fusion was determined by comparing the area under the melting endotherm to the area of fusion of an indium sample having a known heat of fusion of 28.4 J/g, and divided by 292 J/g, the heat of fusion of an ideal polyethylene crystal, to get the degree of crystallinity.

Results and Discussion

As shown in FIG. 1, irradiation increased the crystallinity of the 8 mm thick specimens of UHMWPE from about 55% to 60-66%, with considerable overlapping for the different doses. Similar changes were observed with the samples that were irradiated in air. The gel content (i.e., the extent of crosslinking) (FIG. 2) also increased with increasing radiation dosage. Importantly, crosslinking increased markedly moving from the surface into the middle of each specimen, reaching about 92% for the 3.3 Mrad dose. Apparently, the oxygen present in the vacuum chamber was sufficient to cause the increased oxidation and decreased crosslinking of the surface layer. Thus, our method, i.e., of irradiating a bar and machining away the surface is more effective and efficient than use of a vacuum or other low oxygen atmosphere in producing a final product with minimal oxidation of the bearing surface. For reference (FIG. 3), chemically crosslinked polyethylene (PE) (1% peroxide, irradiated in air) (Shen, F. W. et al. *J. of Poly. Sci.* Part B: *Poly. Phys* 34:1063-1077 (1996)), which exhibits very low wear, has a gel content of about 90% at about 100 microns from the surface, rising to a maximum of nearly 100% in the center.

In a second phase of this example, the 8 mm thick disks that had been irradiated in vacuum were remelted by heating to 145° C. for one hour, and slowly cooled. This reduced the peak melting temperature, the degree of crystallinity and the crystal size. For example (FIG. 4), the crystallinity of the 3.3 Mrad specimens was reduced from the range of 60-65% to the range of 50-53% by remelting.

In addition, during remelting, residual free radicals that were formed by the irradiation apparently recombined and increased the total crosslinking (as evident from the increased gel content, FIG. 5). Extinguishing free radicals in this manner, in turn, further reduces the oxidation that would otherwise occur when the cups are stored on the shelf or exposed to body fluids after implantation.

The lower gel content (crosslinking) near the surface (FIG. 3) was due to oxidation of the surface layer at the time of irradiation. Thus, it can be expected that the polymer of the surface layer would have less wear resistance than that in the center of the specimen. In the method presented in this application, this gradient would not be present, since the surface layer would be removed during machining of the final implant from the irradiated bar or block.

Figure 4:
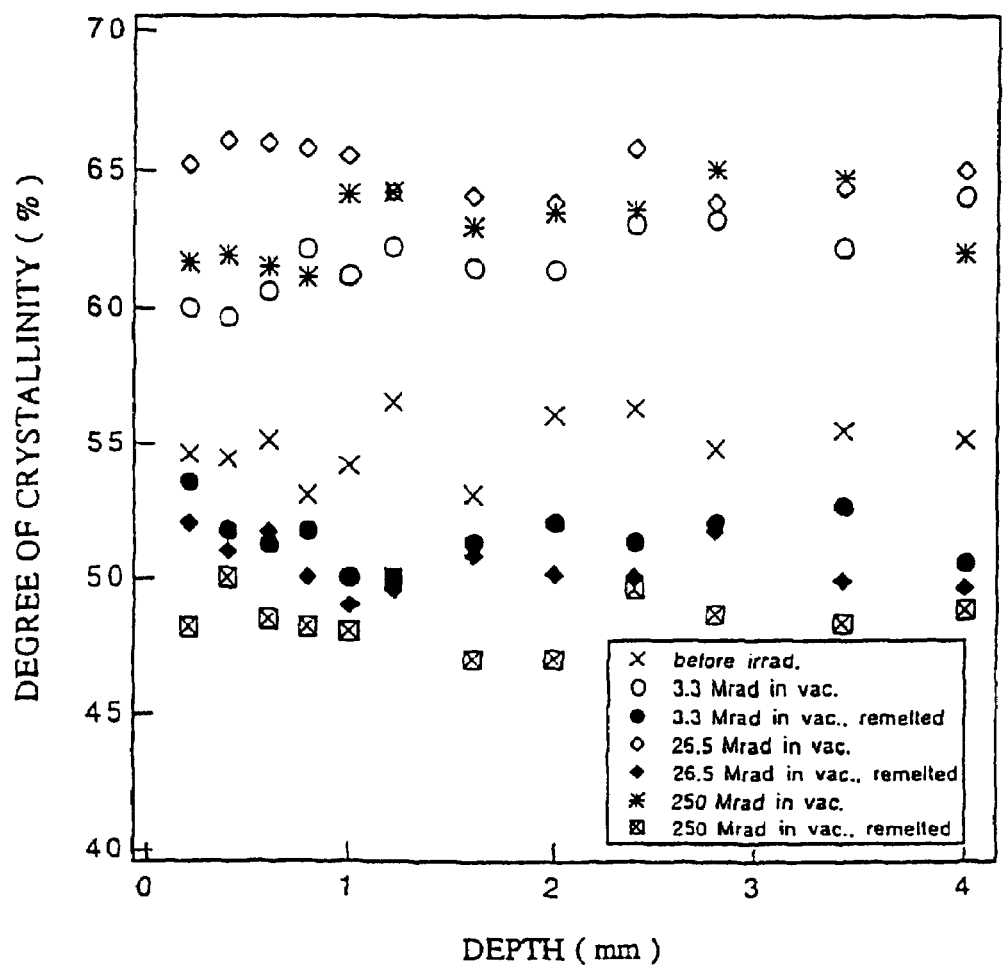
FIG. 4 presents the degree of crystallinity vs. depth at indicated conditions for UHMWPE.

The crystallinity and gel content of the irradiated 8 mm thick disks, with and without remelting, are compared in FIGS. 4 and 5, respectively.

Example 2

Wear Testing of Radiation Crosslinked Cups With and Without Remelting

Experimental Details

Six extruded bars of UHMWPE (GUR 4150), each 3 inches in diameter, were exposed to 3.3 or 28 Mrad of gamma radiation at a dose rate of 0.2 Mrad per hour in ambient air (SteriGenics, Inc., Tustin, Calif.). Two bars for each radiation dose were then remelted by heating in an oven in ambient atmosphere from room temperature to 150° C. at about 0.3° C. per minute and holding at 150° C. for five hours, and then slow-cooling to room temperature. The crystallinity and gel content of these four materials were measured across the cross section of extra samples of each bar using differential scanning calorimetry (DSC) and gel content analysis. The results are summarized in Tables 1 and 2.

Four sets of acetabular cups were machined from bars of each of the four materials at a commercial machining shop (Bradford and Meneghini Manufacturing Co., Santa Fe Springs, Calif.). Each cup had a 2 inch outer diameter (O.D.) and 1.26 inch inner diameter (I.D.), and 1 inch outer radius and 0.633 inch inner radius (FIG. 6). wear tests were run on two sets of three cups for each radiation dose that had been remelted, and two sets of three cups for each dose that had not been remelted. The bars were intentionally used with larger diameters than the final cups so that the process of machining away the outer 0.5 inches of each bar removed the most oxidized, most crystalline, least crosslinked surface layer which is about 0.5 to 1.0 mm thick. In this manner, the bearing surface of each cup consisted of material from near the center of the bar, i.e., the most crosslinked, least crystalline, least oxidized region, which is predicted to be the most wear resistant.

Since acetabular cups used in patients must first be sterilized by some acceptable means, the test cups in this study were sterilized prior to wear testing using ethylene oxide at the appropriate dose for clinical implants. Ethylene oxide was chosen instead of additional gamma irradiation (e.g., 2.5-4.0 Mrad) in order to confine the results to the effects of the original 3.3 or 28 Mrad doses used to crosslink the materials.

Figure 7:
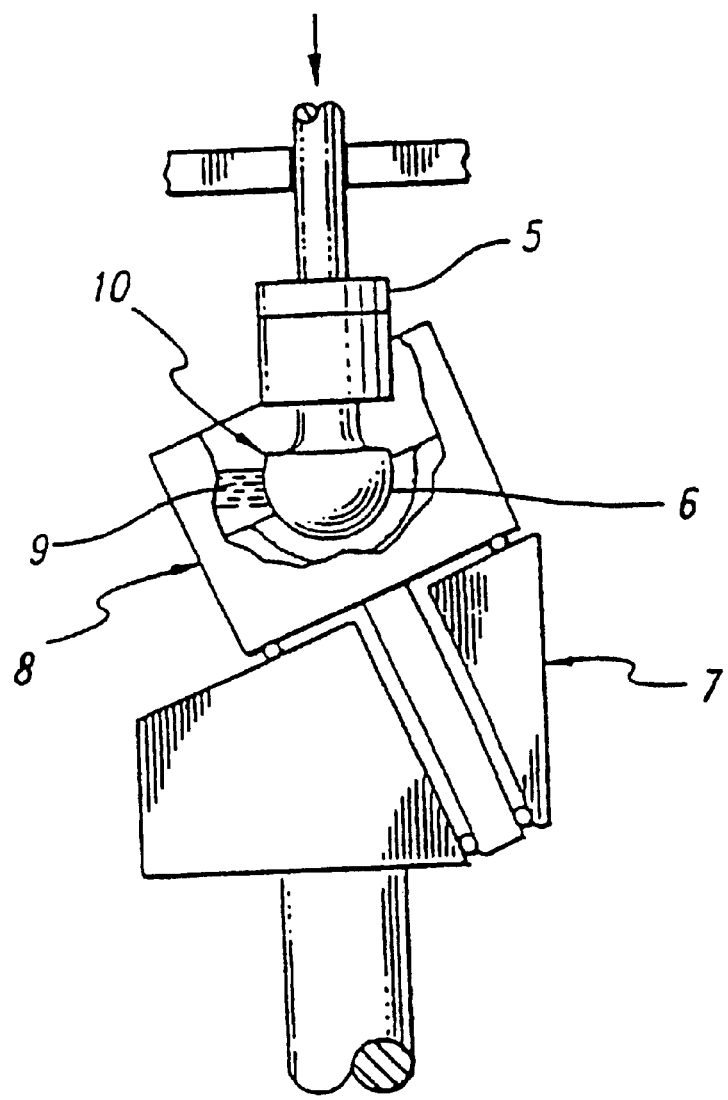
FIG. 7 presents a schematic diagram of the hip joint simulator used in the wear tests.

Prior to wear testing, the cups were pre-soaked in distilled water for three weeks to minimize additional fluid absorption during the wear test, thereby making the weight loss method for wear measurement more accurate. For the wear test, the cups were enclosed in polyurethane molds and pressed into stainless steel holders (FIG. 7). Each holder was fitted with an acrylic chamber wall to contain the lubricant. The chambers were mounted on the hip simulator wear machine, with each cup bearing against a ball of cobalt-chromium alloy (conventional hip replacement femoral balls were used, with implant-quality surface finish). The ball-cup pairs were subjected to a physiological cyclic load with a peak load of about 2000 Newtons (Paul, J P., "Forces transmitted by joints in the human body". *In Lubrication and Wear in Living and Artificial Human Joints*. Proc Instn Mech Engrs 1967; 181 Part 3J:8-15) and the cups were oscillated against the balls through a bi-axial 46° arc at 68 cycles per minute. Each test station on the simulator (FIG. 7) contains a self-centering unit 5, the acetabular cup 6, a dual axis offset drive block 7, a test chamber 8, serum lubricant 9 and a femoral ball 10. The arrow indicates the direction of the computer controlled simulated physiological load applied to the simulated hip joint.

During the test, the bearing surfaces were kept immersed in bovine blood serum to simulate lubrication in the human body. Sodium azide at 0.2% was added to the serum to retard bacterial degradation, and 20 mM ethylene-diaminetetraacetic acid (EDTA) was added to prevent precipitation of calcium phosphate onto the surface of the balls (McKellop, H. and Lu, B., "Friction and Wear of Polyethylene-metal and Polyethylene-ceramic Hip Prostheses on a Joint Simulator, Transactions of the Fourth World Biomaterials Congress, Berlin, April 1992, p. 118). A polyethylene skirt covered each test chamber to minimize airborne contaminants.

At intervals of 250,000 cycles, the cups were removed from the machine, rinsed, inspected under light microscopy and replaced in fresh lubricant. At intervals of 500,000 cycles, the cups were removed, cleaned, dried and weighed to indicate the amount of wear. After inspection under light microscopy, the cups were replaced on the wear machine with fresh lubricant and testing was continued to a total of three million cycles. One million cycles is approximately the equivalent of one year's walking activity of a typical patient.

The weight loss was corrected for the effects of fluid absorption (which masks wear) by increasing the apparent weight loss of the wear test cups by the mean weight gain of three control cups of each material that were also immersed in serum and cyclically loaded on a separate frame, but without oscillation. The corrected rate of weight loss was converted to volume loss by dividing by the approximate density of UHMWPE (0.94 gm/cc). The mean weight loss (after soak correction) and the standard deviation was calculated for each of the four types of materials at each weighing interval. The wear rate of each cup was calculated by applying linear regression to the wear data for the entire three million cycles. The mean wear rates and standard deviations also were calculated for each type of material.

Results

Figure 8:
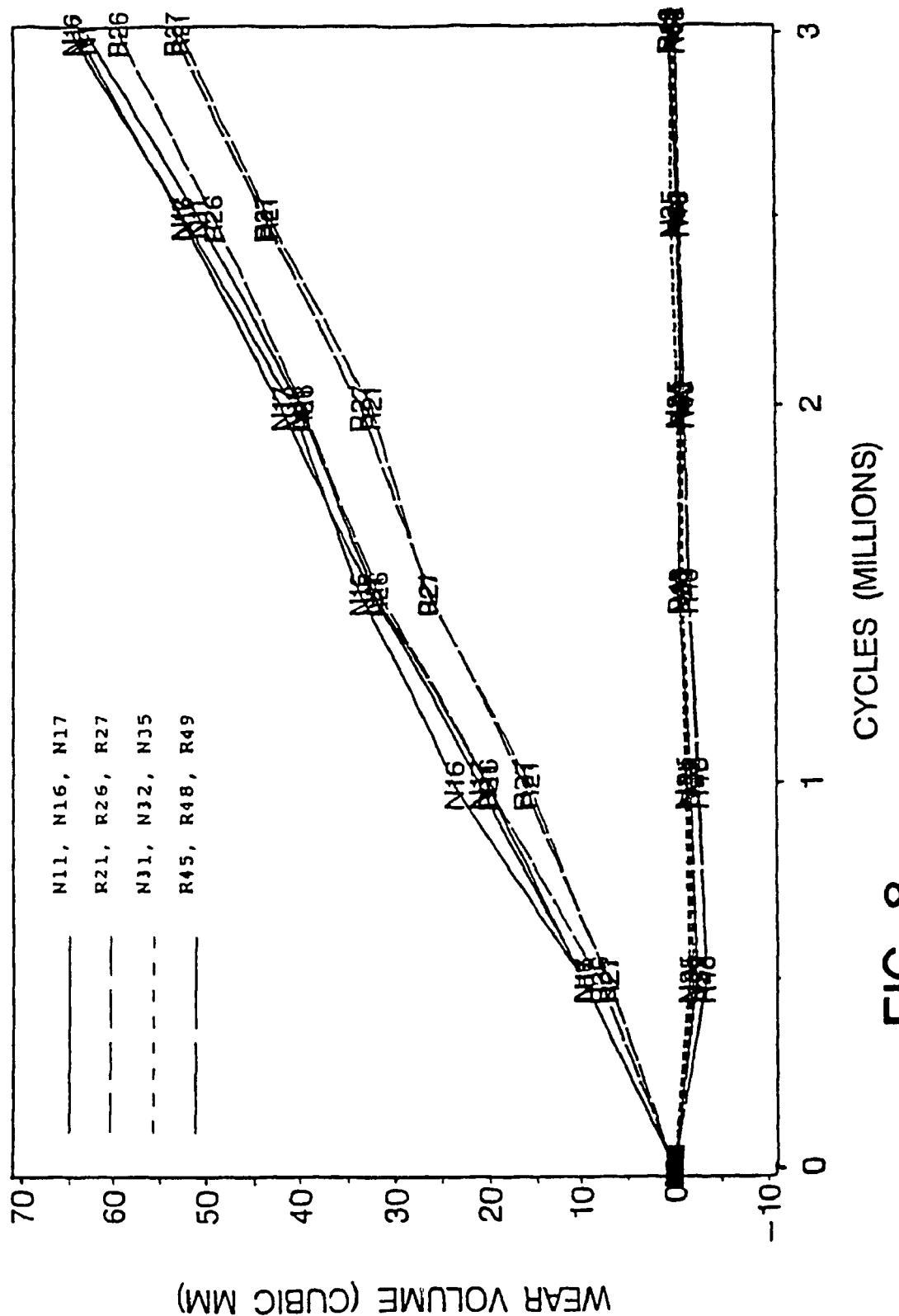
FIG. 8 presents the wear by volume loss of each cup of the four materials. Upper curves: 3.3 Mrad; Lower curves: 28 Mrad.
Figure 9:
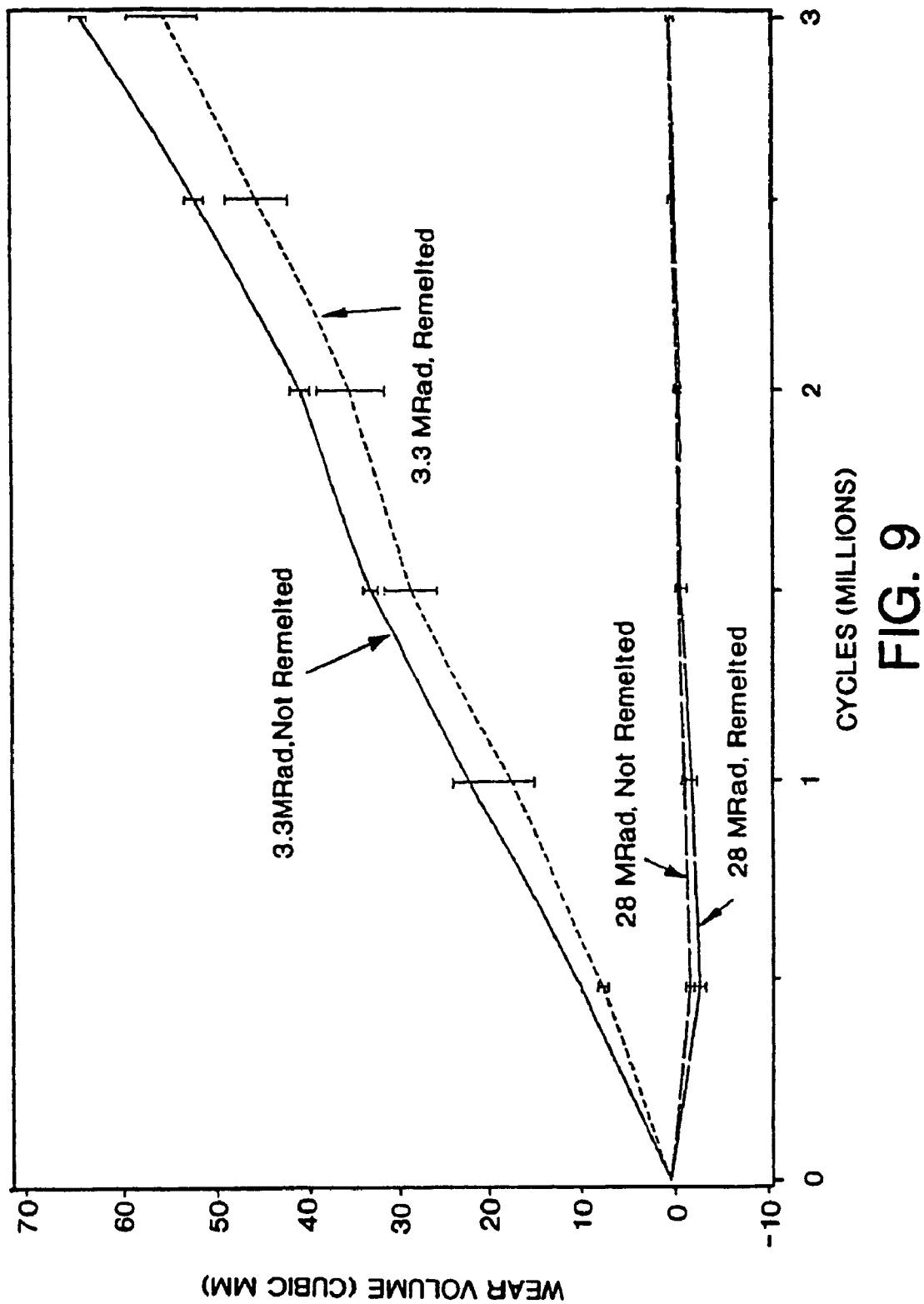
FIG. 9 presents the curves of the average volumetric wear and standard deviations of three cups of each material at each interval.

FIG. 8 shows the soak-corrected wear (volume loss) of three cups of each material as a function of wear cycles. FIG. 9 shows the average wear (volume loss) of three cups of each material as a function of wear cycles. The individual wear races and the mean values for each type of material are listed in Table 3. The most wear occurred with the cups subjected to 3.3 Mrad without remelting. These averaged 21.1 mm$^3$ per million cycles.

The wear of the cups subjected to 3.3 Mrad with remelting averaged 18.6 mm$^3$ per million cycles, or 12% lower wear than for the non-remelted 3.3 Mrad cups. The cups subjected to 28 Mrad had much lower wear rates than the 3.3 Mrad cups, and the rates were similar, whether or not the material had been remelted. That is, the average wear rate of the non-remelted 28 Mrad cups was about 1.2% that of the non-remelted 3.3 Mrad controls, and the average wear rate of the remelted 28 Mrad cups was about 1.7% of the same controls.

Discussion

The results of the wear test clearly demonstrated the improved wear resistance of the UHMWPE acetabular cups that resulted from exposure to 28 Mrad gamma radiation. Apparently, the crosslinking generated by the higher radiation dose reduced the wear rates to less than a few percent of the control value (3.3 Mrad). The minimum amount of wear debris necessary to induce clinically significant osteolysis and other problems in a specific patient has not been established, and it may vary among patients. Nevertheless, a material which reduces the wear rate to the very low levels exhibited by the 28 Mrad cups in this study would be very likely to provide a large margin of safety over currently used materials.

The wear curves for both of the 28 Mrad specimens (FIGS. 8 & 9) were slightly negative on the first weighing at 0.5 million cycles. This was most likely due to a slight under-correction for fluid absorption (that is, the wear test cups absorbed slightly more water than the soak controls, and the error between the two was greater than the weight loss due to wear, producing a negative wear value). If this assumption is correct, then the overall wear rates for the two 28 Mrad sets were somewhat smaller, and possibly closer together, than the values indicated in Table 3.

Example 3

Artificial Aging of Radiation-Crosslinked UHMWPE Materials

Six UHMWPE (GUR 4150) extruded bars (3" diameter) were gamma irradiated in air, three bars each at 3.3 or 28 Mrad, at a dose rate of 0.2 Mrad/hour. For each radiation dose, two bars were then remelted by heating in an oven at ambient atmosphere from room temperature to 150° C. at about 0.3° C./min, holding at 150° C. for 5 hours and slowly cooling to room temperature, and the third bar was not remelted. A 13 mm (0.5 inch) layer of the outer diameter of the treated (remelted) and untreated (non-remelted) bars was machined away to remove the most oxidized, least crosslinked surface layer. The bars were used to produce specimens for the artificial aging tests described here and for the wear tests described in EXAMPLE 2.

To examine the effect of artificial aging on these four materials (3.3 and 28 Mrad, remelted and not remelted), 8 mm thick disks were cut from these 2 inch diameter cores and were heated in an oven slowly (~0.2° C./min) to 80° C. at ambient atmosphere and held at 80° C. for 10, 20 or 30 days. In addition, one acetabular cup for each of the four conditions (3.3 and 28 Mrad, remelted and not remelted) that had been fabricated at the same time as the wear test cups of EXAMPLE 2 and stored in air for about 5 months was cut into four pieces and aged at 80° C. for the same periods.

The gel content analysis and DSC method are as described in EXAMPLE 1, above.

Fourier Transform Infrared Spectroscopy (FTIR)

FTIR measurements were performed on the above specimens. Segments about 5 mm wide were cut from each polyethylene specimen and the segments were microtomed into 200 µm thick slices. The oxidation profiles, as indicated by the carbonyl concentration, were measured using a Mattson Polaris FTIR (model IR 10410) with a Spectra-Tech IR plan microscope. Spectra were collected in 100 µm steps from the surface to the middle of the specimen, using 64 scans summation at a resolution 16 $cm^{-1}$ with a MCT (Mercury Cadmium Telluride) detector. The carbonyl group concentration was indicated by the ratio of the peak height of the ketone absorption band at 1717 $cm^{-1}$ to the height of the reference band at 2022 $cm^{-1}$ (—$CH_2$-vibration)

Results

Figure 10:
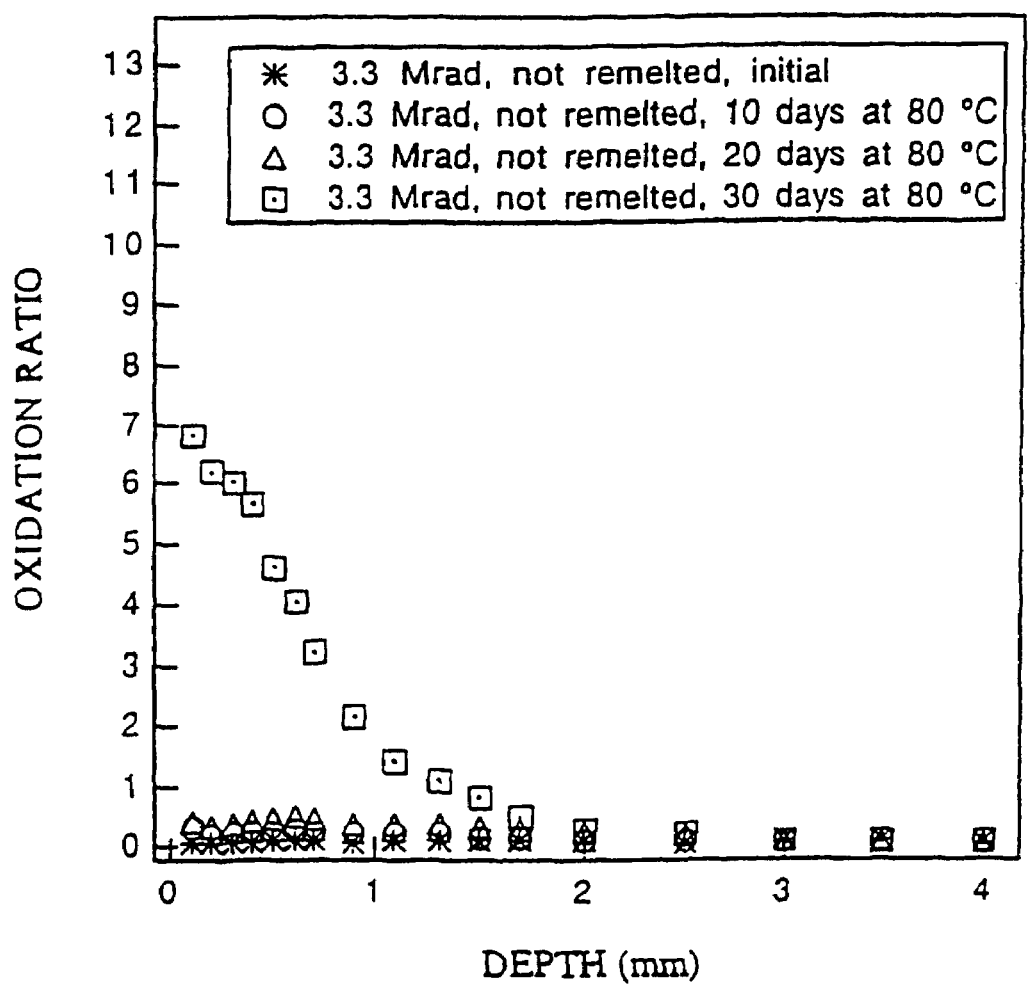
FIG. 10 presents the oxidation profile as a function of depth at various aging times.
Figure 11:
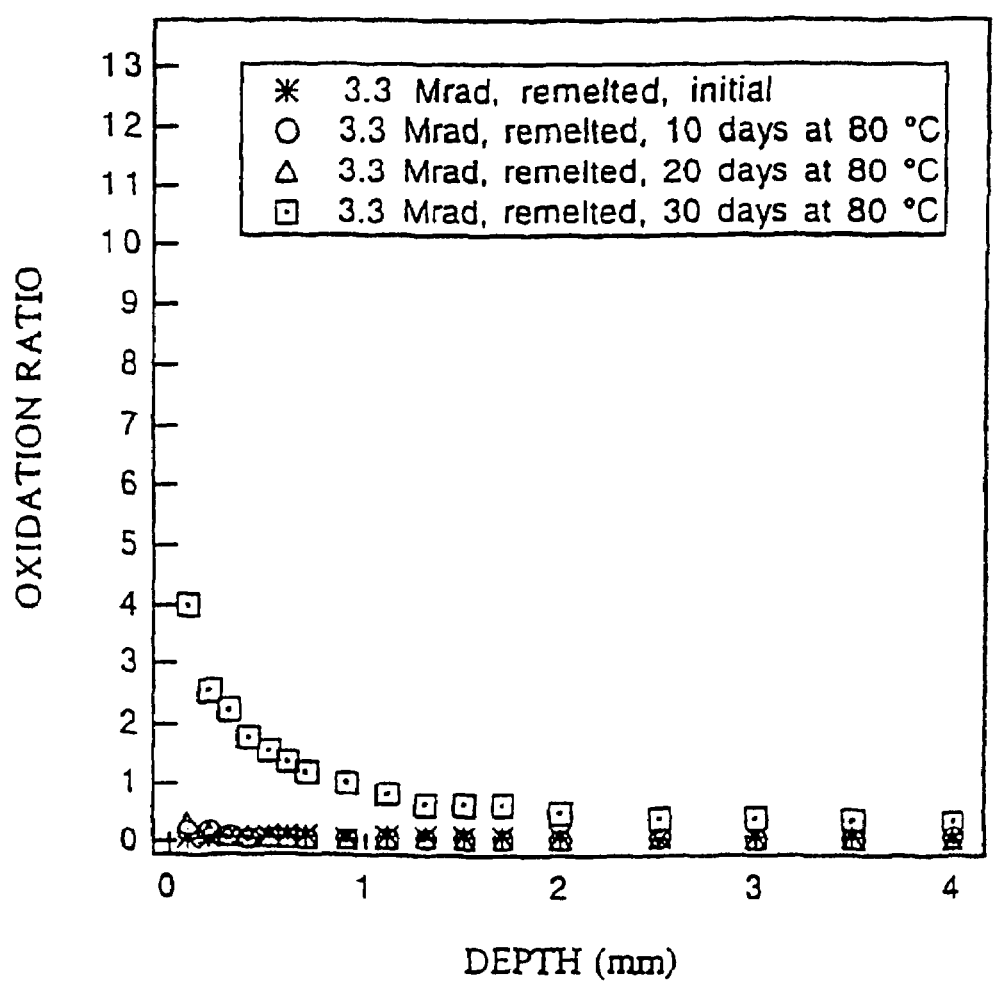
FIG. 11 presents the oxidation profile as a function of depth at various aging times.
Figure 12:
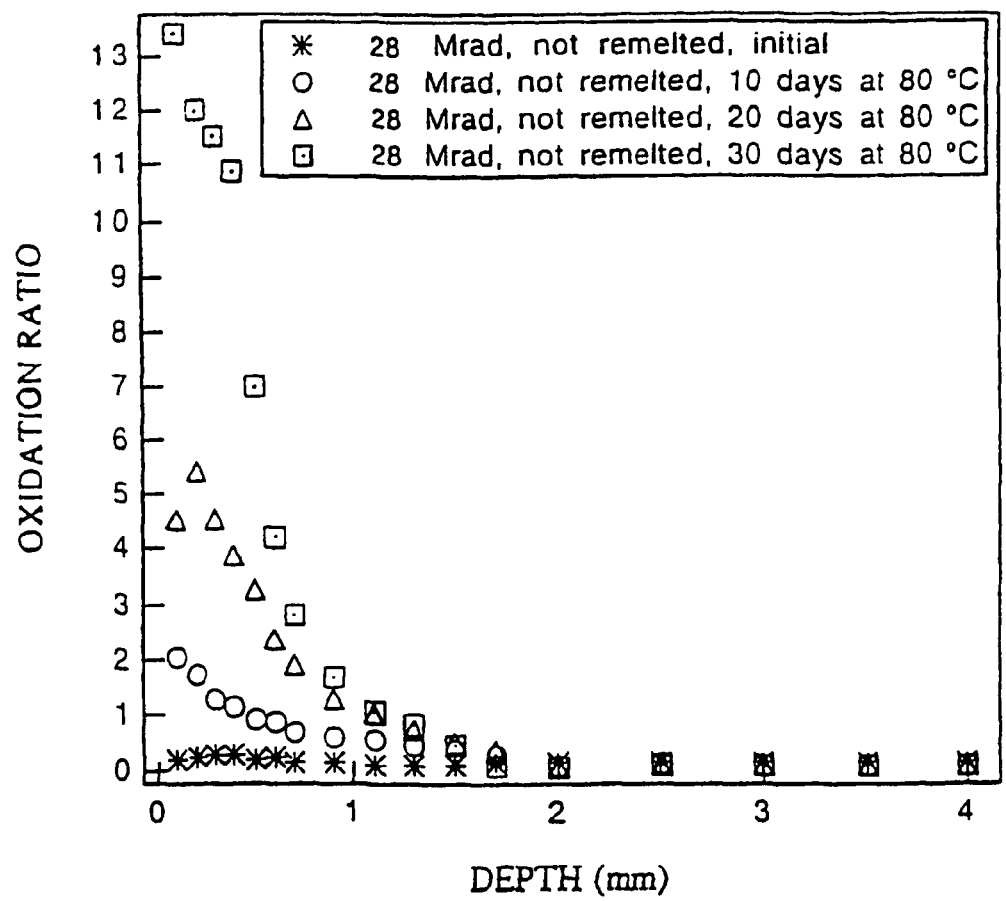
FIG. 12 presents the oxidation profile as a function of depth at various aging times.
Figure 13:
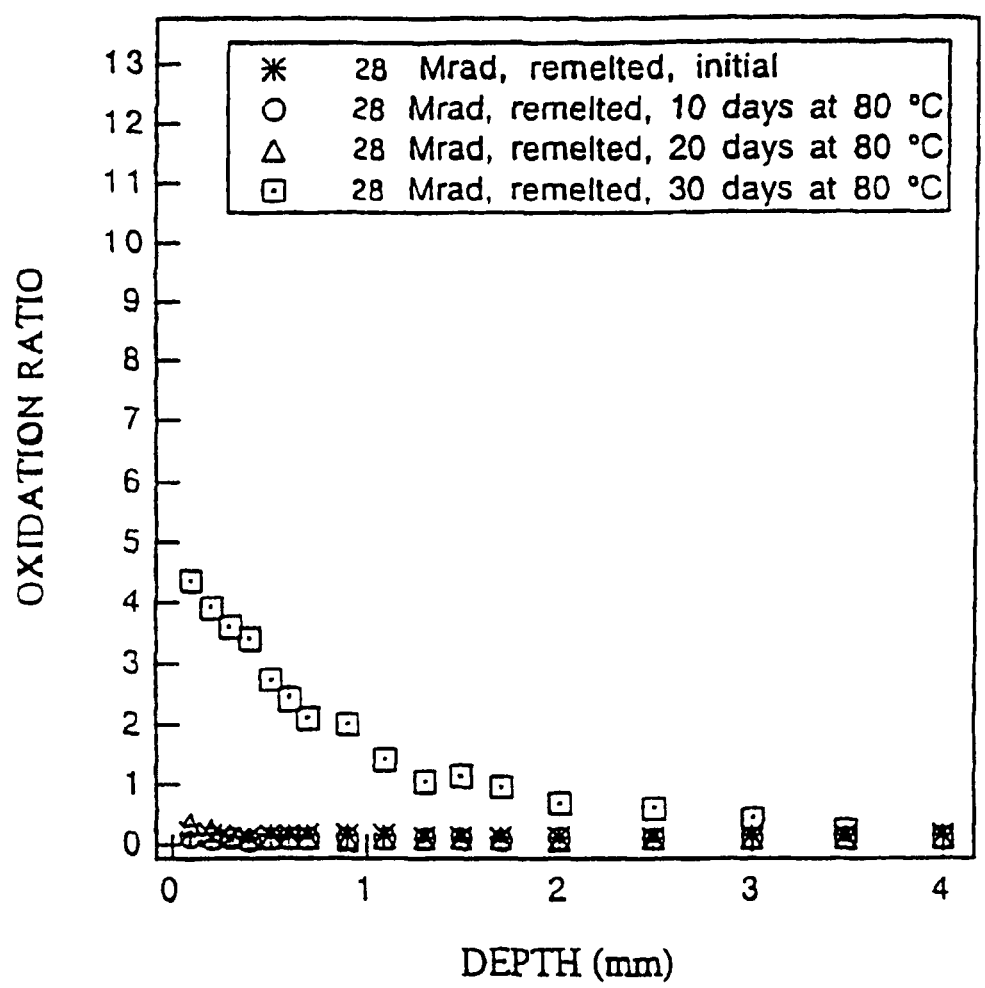
FIG. 13 presents the oxidation profile as a function of depth at various aging times.

The oxidation profiles as a function of depth are shown in FIGS. 10-13. As shown in FIG. 10 for the 3.3 Mrad, non-remelted material, oxidation increased with increasing aging time. In contrast, the 3.3 Mrad, remelted material (FIG. 11) showed almost no oxidation for 10 and 20 days aging, but some oxidation for 30 days aging. However, the oxidation peak at the surface with remelting was about 50% of that at the surface without remelting (FIG. 10). For the 28 Mrad, non-remelted UHMWPE (FIG. 12), the oxidation showed a greater increase with increasing aging time than the 3.3 Mrad, un-remelted material. Again, oxidation was much lower with remelting, i.e., the 28 Mrad, remelted UHMWPE (FIG. 13) essentially exhibited no oxidation after 20 days aging (FIG. 13), and the oxidation peak at the surface after 30 days was only about ⅓ that without remelting (FIG. 12).

Figure 14:
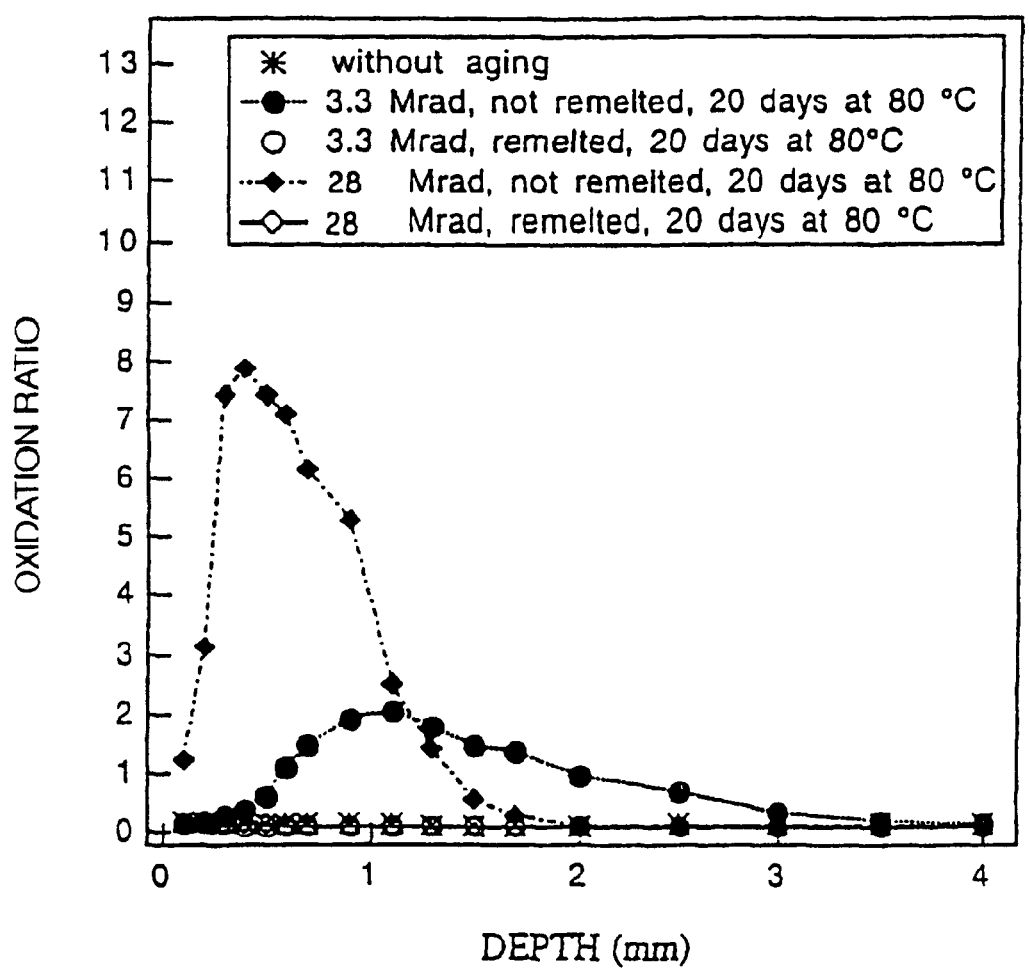
FIG. 14 presents the oxidation profile as a function of depth for various materials. The specimens were stored in air for 5 months and then aged for 20 days at 80° C.

Similarly, with the acetabular cups stored in air for 5 months and then aged for 20 days at 80° C., the remelted materials (3.3 or 28 Mrad) showed no oxidation (FIG. 14), while the non-remelted cups (3.3 or 28 Mrad) showed substantial oxidation (FIG. 14), especially for 28 Mrad UHMWPE, and with a subsurface oxidation peak in both non-remelted materials.

Figure 15:
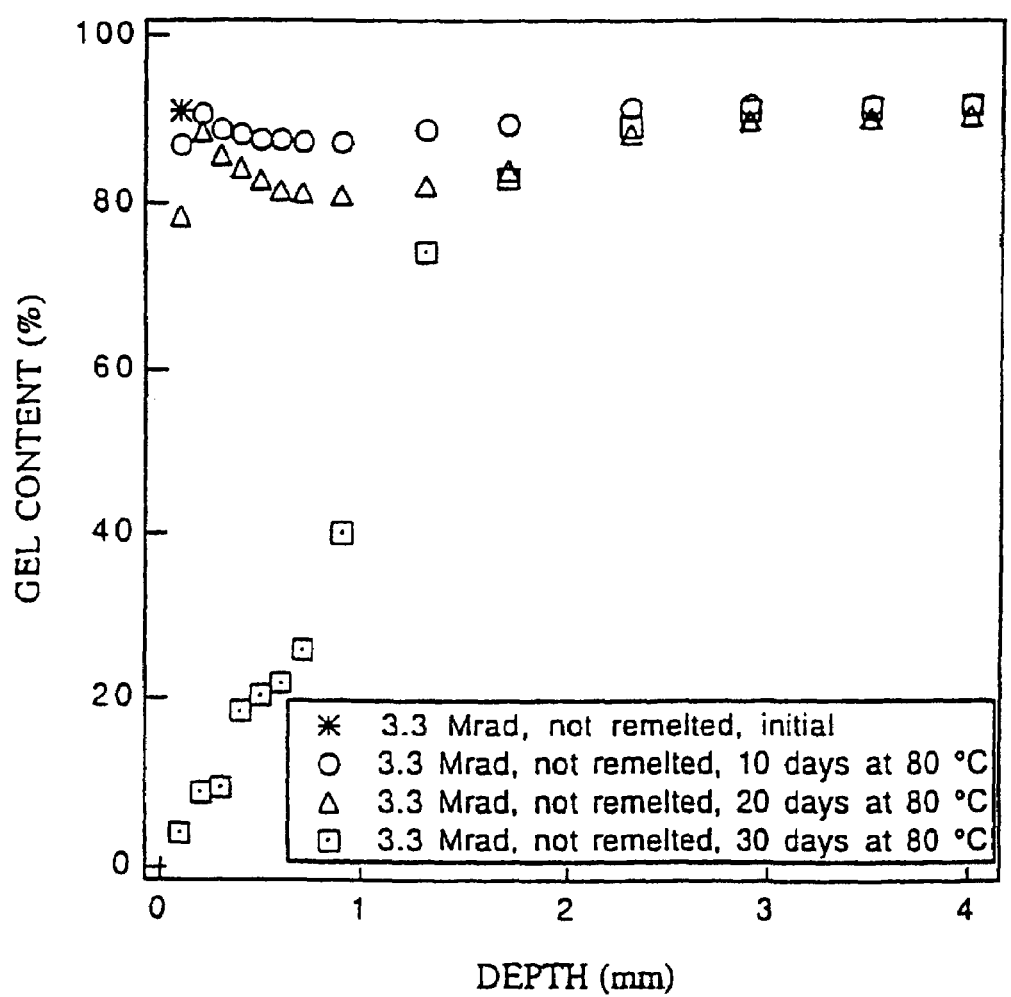
FIG. 15 presents gel content as a function of depth at various aging times.
Figure 16:
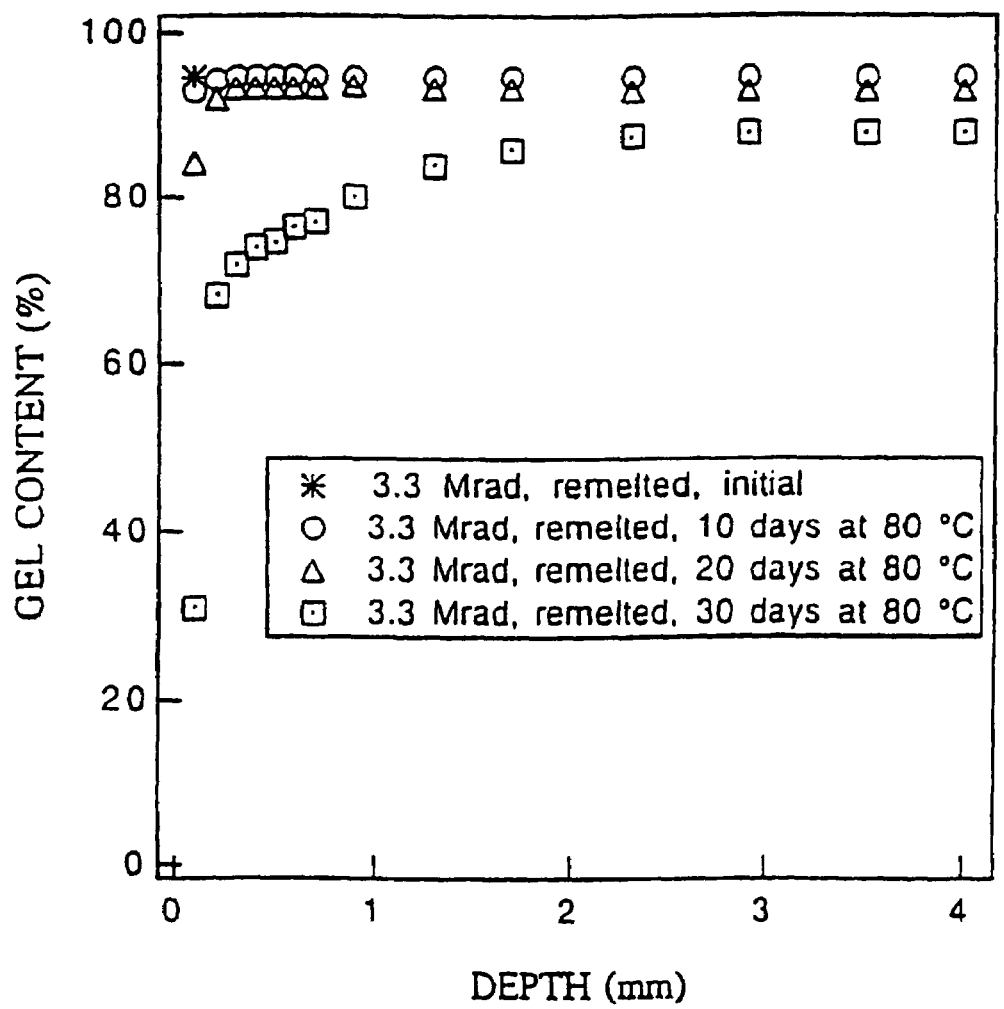
FIG. 16 presents gel content as a function of depth at various aging times.
Figure 17:
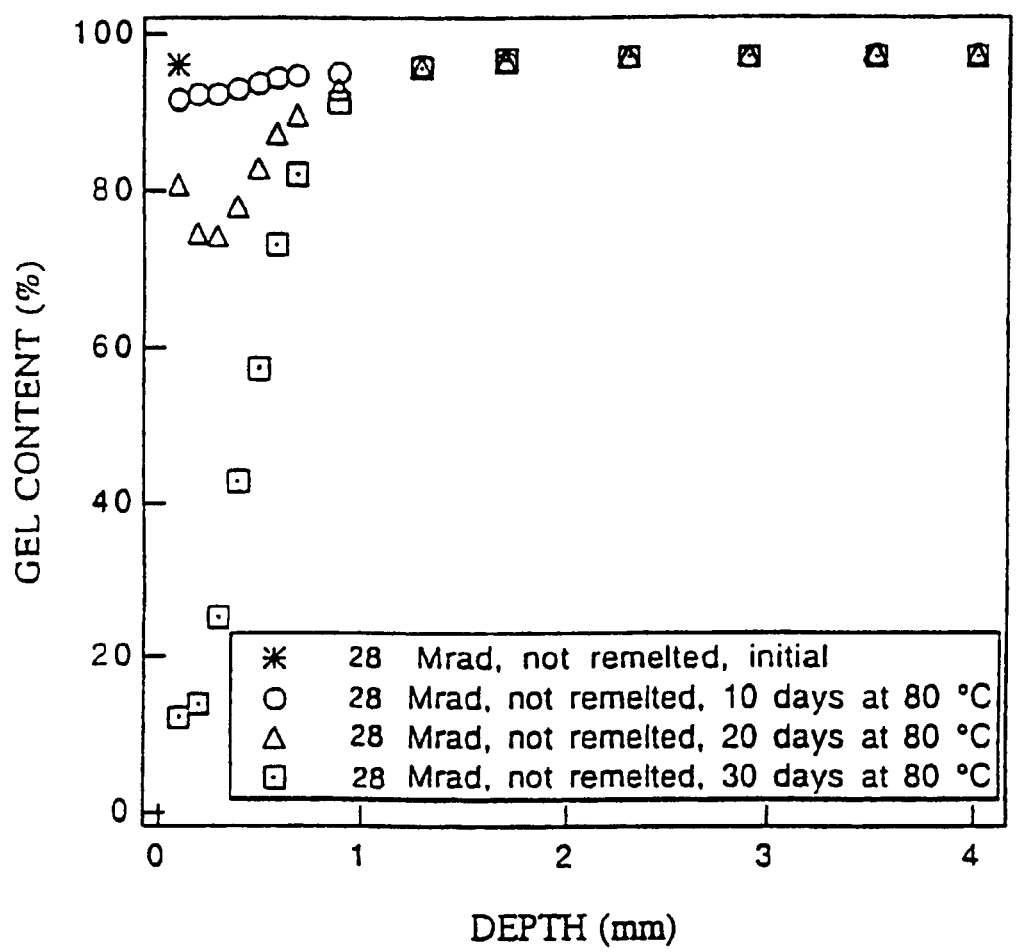
FIG. 17 presents gel content as a function of depth at various aging times.
Figure 18:
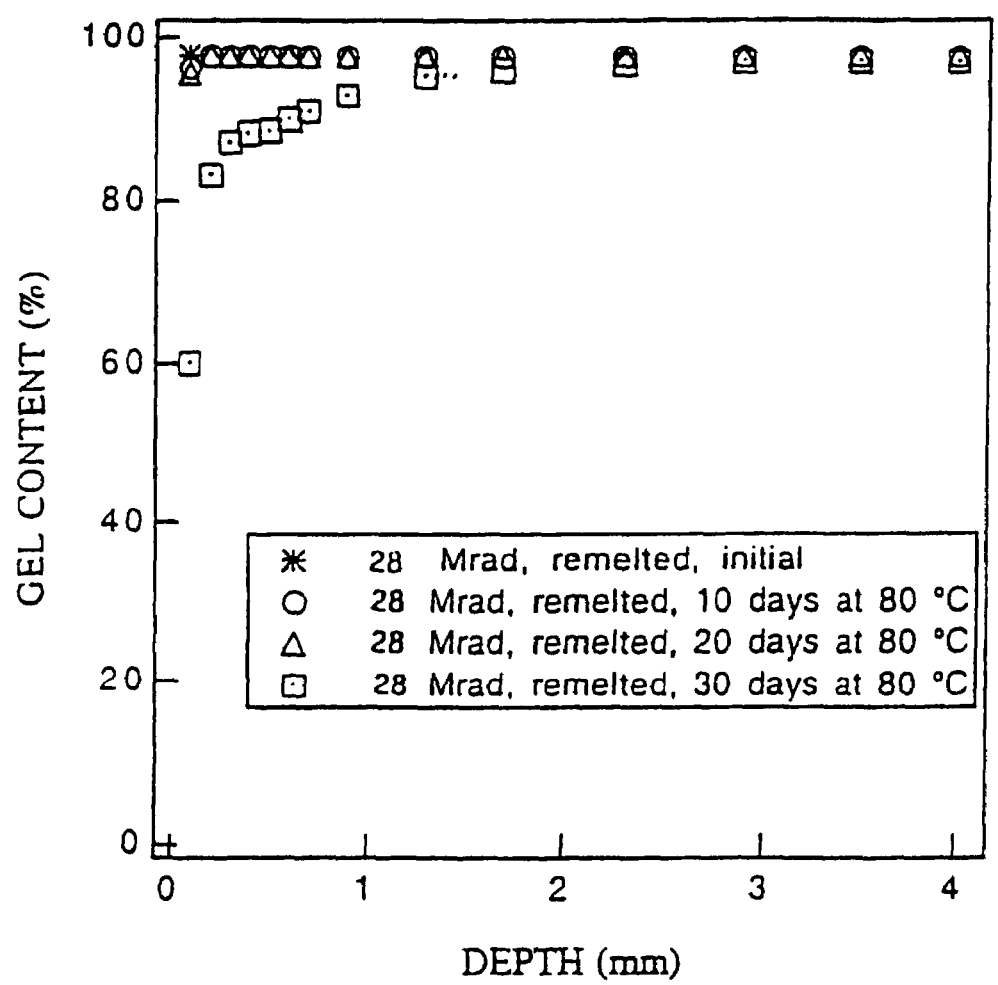
FIG. 18 presents gel content as a function of depth at various aging times.

Since crosslinking of UHMWPE reduces its solubility, the percent of undissolved material (gel content) is an indirect indication of the amount of crosslinking. The gel content as a function of depth for various conditions are shown in FIGS. 15 to 18. As shown in FIG. 15 for 3.3 Mrad, non-remelted material, the gel content (i.e., crosslinking) decreased with increasing aging time. There was a strong gradient of gel content in the highly oxidized surface regions after 30 days aging, i.e., increasing from a minimum on the surface to a maximum about 2 mm below the surface. Near the surface, the gel content was highest (91%) in the un-aged specimen, and decreased with increasing aging time to less than about 5% in the same region for the 30 day aged specimen. In contrast, the remelted materials (FIG. 16) showed much less reduction in gel content in the surface regions than the non-remelted materials. That is, comparison of FIG. 17 (28 Mrad, non-remelted) and FIG. 18 (28 Mrad, remelted) showed that the remelted UHMWPE had much higher retention of gel content (i.e., crosslinking).

Figure 19:
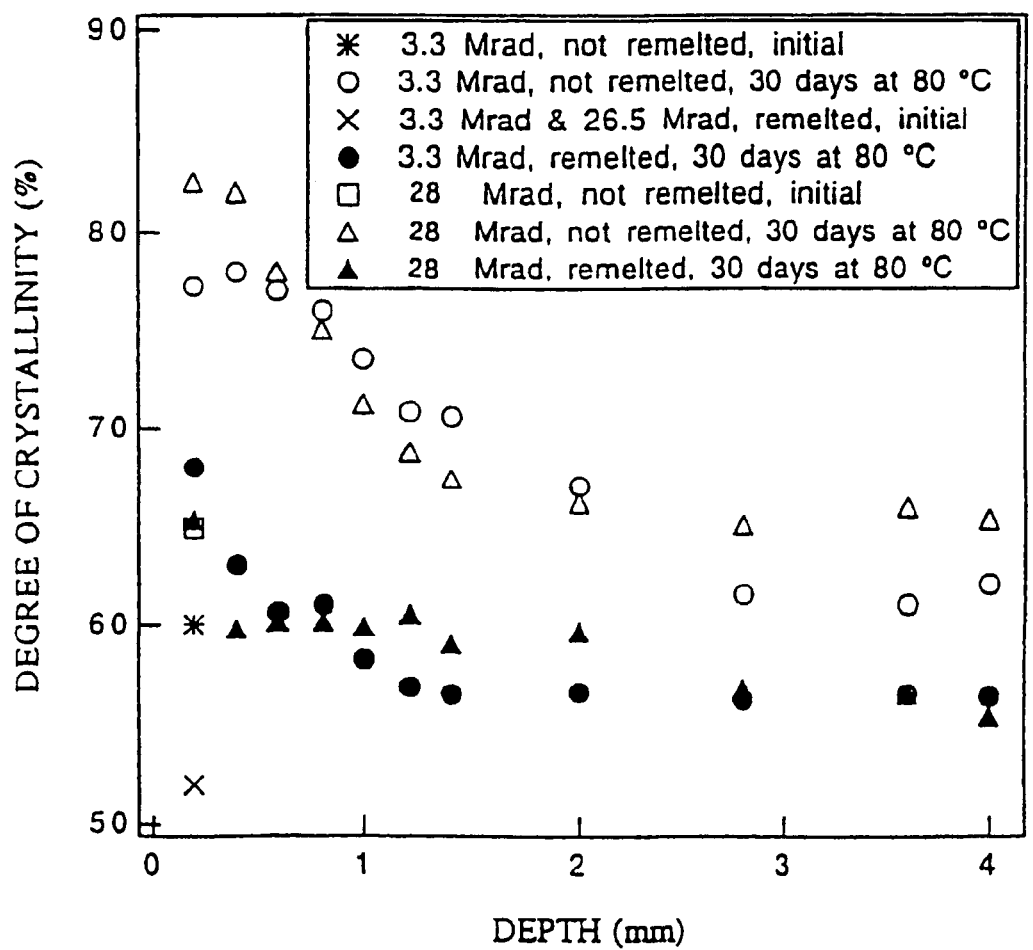
FIG. 19 presents the degree of crystallinity as a function of depth after 30 days' aging.

The results of the DSC measurements indicated the degree of crystallinity as a function of depth for various materials aged for 30 days at 80° C., as shown in FIG. 19. Near she surface, the degree of crystallinity was 83% for the 28 Mrad, non-remelted material after aging, compared to 65% before aging. The high level of crystallinity and increased brittleness of the surface zone of the aged material often resulted in fragmentation of a layer about 1 mm thick during microtoming. In contrast, the 28 Mrad remelted material showed less increase in crystallinity in the surface regions due to aging, and no brittle zone was observed. Similarly, due to aging, the 3.3 Mrad non-remelted material exhibited an increase in crystallinity from 60% to about 78%, and the surface layer was again brittle, although not as brittle as with the 28 Mrad, non-remelted material.

Discussion

Irradiation of UHMWPE produces crosslinking, chain scission and the formation of free radicals. If oxygen is present, it may react with the free radicals to form oxidized species, leading to additional chain scission (reduction in molecular weight) and an increase in crystallinity. Since polymer crystallites melt and become amorphous above the melting temperature, molecular chain movements and rotations are increased, favoring the recombination of free radicals. The results of the present experiments showed that remelting at 150° C. apparently caused the residual free radicals to decay and/or to recombine to form crosslinks, leading to an increased gel content. Therefore, remelting is an effective way to extinguish free radicals, making the material less susceptible to long-term oxidation and potentially improving the long-term wear resistance, as evident from the results of the artificial aging experiments, where there was much less oxidation of the remelted materials.

For a crosslinked polymer, oxidative degradation cleaves the molecules and leads to a reduction in gel content. This was evident in the present experiments from the reduced gel content after aging, particularly with the nonremelted materials (FIGS. 15 to 18). That is, the distribution of oxidation, as indicated by the profiles measured by FTIR, was inverse to the gel content within the material; the higher the oxidation, the lower the gel content (crosslinking). Since remelting extinguishes free radicals and increases gel content, thereby reducing the susceptibility to oxidation, the remelted materials (3.3 and 28 Mrad) had a much greater gel content after artificial aging than the non-remelted materials.

An appropriate amount of crosslinking of UHMWPE can improve its wear resistance. The high level of crosslinking in the UHMWPE caused by the 28 Mrad gamma irradiation, as evident from the high gel content (EXAMPLE 2), apparently contributed to the much greater wear resistance exhibited by the acetabular cups tested in EXAMPLE 2. In addition, as shown in EXAMPLE 3, remelting of the irradiated UHMWPE markedly reduced the residual free radicals, rendering the material much more resistant to subsequent oxidation and, therefore, resistant to a reduction in crosslinking, which can be of substantial benefit for implants in long-term clinical use.

Example 4

Wear Testing of Irradiated Cups With and Without Artificial Aging

Materials and Methods

The wear testing of irradiated cups with and without remelting was described in EXAMPLE 2. Effects of artificial aging on the physical properties of irradiated UHMWPE, with and without remelting, were described in EXAMPLE 3. To examine the resistance of crosslinked cups to thermal-induced oxidation, and the effect of such oxidation on the wear of irradiated cups with and without remelting, two acetabular cups for each of the four conditions (3.3 and 28 Mrad, remelted and not remelted) that had been wear tested for 3 million cycles as described in EXAMPLE 2, were heated in an oven slowly (~0.2° C./min) to 80° C. at ambient atmosphere and held at 80° C. for 20 days, with one acetabular cup for each of the four conditions being stored in ambient air. The oxidation profile after 20-day aging for each condition was shown in FIG. 14, EXAMPLE 3.

Prior to wear testing, the cups were pre-soaked in distilled water for four weeks to minimize additional fluid absorption during the wear test, thereby making the weight loss method for wear measurement more accurate. The details for the wear test were described in EXAMPLE 2.

Results

Figure 20:
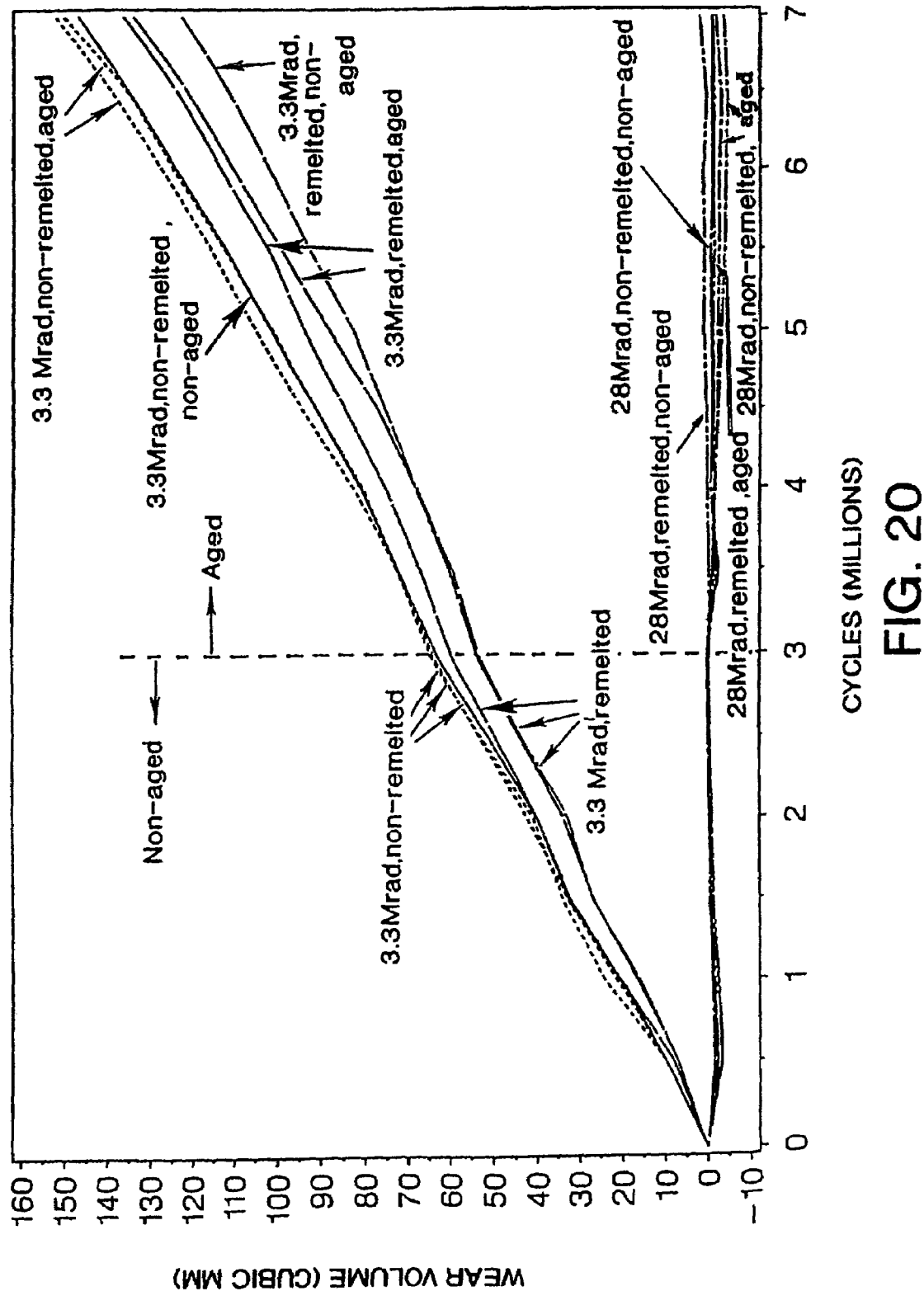
FIG. 20 shows the combined soak-corrected wear for the non-aged and aged cups.

FIG. 20 shows the combined soak-corrected wear (volume loss) for the cups before aging (3.3 and 28 Mrad, remelted and not remelted) during the first 3 million cycles (same data as EXAMPLE 2) and for the same cups, after two cups of each material had been artificially aged, from 3 to 7 million cycles. The individual wear rates and the mean values for each type of material, calculated by linear regression, are listed in Table 4.

All cups subjected to 3.3 Mrad with remelting showed comparable wear rates, whether or not the material had been remelted or remelted and aged. Wear was negligible for all of the cups subjected to 28 Mrad, whether or not these were remelted, and whether or not they were aged.

Discussion

The results of the wear test clearly demonstrated the improved wear resistance of the UHMWPE acetabular cups that resulted from exposure to 28 Mrad gamma radiation. Apparently, the minor oxidation at the surface (FIG. 14) of the highly crosslinked acetabular cups (28 Mrad, without remelting) induced by the artificial aging, had very limited effect on the wear resistance. Although a substantial oxidation peak occurred about 0.4 mm below the surface, because of the very high wear resistance of the 28 Mrad cups, the total penetration due to wear was too shallow to reach this sub-surface oxidized zone, even after 4 million cycles.

For the non-remelted 3.3 Mrad cups, subsurface oxidation, peaking at about 1 mm below the surface (FIG. 14), occurred after aging in air at 80° C. for 20 days. Since the total depth of penetration of these cups was about 300 microns (at 7 million cycles), the full effect of this subsurface oxidation would not become apparent until a much larger number of wear cycles.

Nevertheless, the sub-surface oxidation in the non-remelted cups (EXAMPLE 3, particularly for the 28 Mrad specimen) leads to reduced molecular weight, a reduction in crosslinking (as indicated by gel content) and an increased crystallinity and brittleness, all of which can contribute to reductions in mechanical properties such as fatigue strength and, eventually, a reduction in wear resistance. Although remelting had no apparent effect on the wear resistance of the aged cups in the present example, the elimination of free radicals by remelting improves the long-term resistance to oxidation, thereby improving the long-term wear resistance in vivo.

Example 5

Wear Testing of Gamma-Irradiated UHMWPE With Multiple Doses

Materials and Methods

In EXAMPLE 2, we demonstrated the improved wear resistance of UHMWPE acetabular cups that resulted from exposure to 28 Mrad gamma radiation, as compared to cups irradiated to 3.3 Mrad. The average wear rate of the 28 Mrad cups was less than 2% of that of the 3.3 Mrad cups (i.e., a dose within the normal 2.5 to 4.0 Mrad range used to sterilize implants). To examine the wear as a function of radiation dose and, thereby, determine an optimum dose for reducing wear, extruded bars of GUR 4150 UHMWPE, 3" diameter×15" long, were gamma irradiated in air, three bars at each dose of 4.5, 9.5, 14.5, 20.2 or 24 Mrad (SteriGenics, Inc., Corona, Calif.), at a dose rate of 0.45 Mrad/hour. Additional bars were irradiated in air to 50 or 100 Mrad (SteriGenics Inc., Tustin, Calif.), at a dose rate of 0.67 Mrad/hour. For each radiation dose, two bars were then remelted by heating in an oven in ambient atmosphere from room temperature to 150° C. at about 0.3° C./min, holding at 150° C. for 5 hours and then slowly-cooled to room temperature, with the third bar not being remelted. The irradiated-remelted bars were used to produce acetabular cups for the wear tests.

Figure 6:
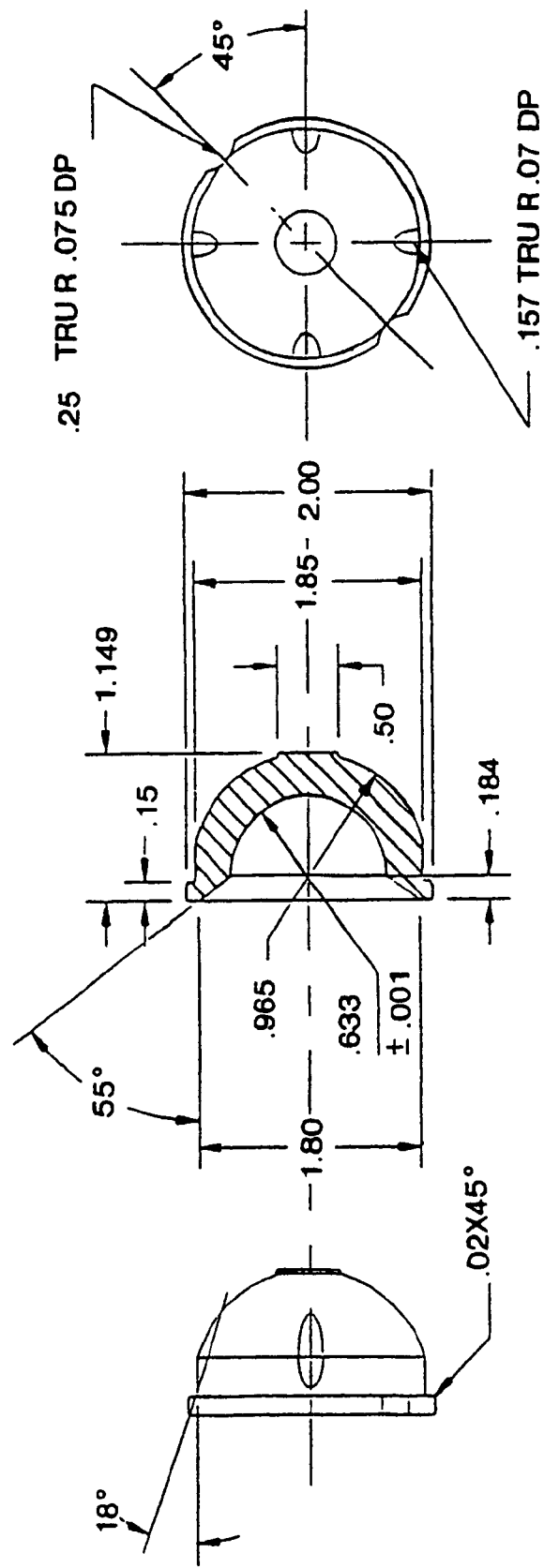
FIG. 6 presents the shape of the acetabular cup fabricated from the irradiated UHMWPE.

Seven sets of acetabular cups were machined from the irradiated-remelted bars for each of the seven doses at a commercial machining shop (Bradford and Meneghini Manufacturing Co., Santa Fe Springs, Calif.). Each cup had a 2" O.D. and 1.26" I.D., with 1" outer radius and 0.63" inner radius (FIG. 6). Wear tests were run on the remelted specimens, using two cups for each radiation dose from 4.5 to 24 Mrad, and one cup each for 50 and 100 Mrad. The bars were intentionally used with larger diameters than the final cups so that the process of machining away the outer layer of each bar, about 0.5 inch thick, effectively removed the most oxidized, most crystalline, least crosslinked surface layer (about 0.5 to 1.0 mm). In this manner the bearing surface of each cup consisted of material from near the center of the bar, i.e., the most crosslinked, least crystalline, least oxidized region, which was expected to be the most wear resistant.

Because acetabular cups used in patients must first be sterilized by some acceptable means, the test cups in this study were sterilized prior to wear testing using ethylene oxide at the appropriate dose for clinical implants. Ethylene oxide was chosen instead of additional gamma irradiation (e.g., 2.5-4.0 Mrad) in order to focus the results on the effects of the radiation doses used to crosslink the materials. Prior to wear testing, the cups were pre-soaked in distilled water for four weeks to minimize additional fluid absorption during the wear test, thereby making the weight loss method for wear measurement more accurate. The details for the wear test method were described in EXAMPLE 2.

Results

Figure 21:
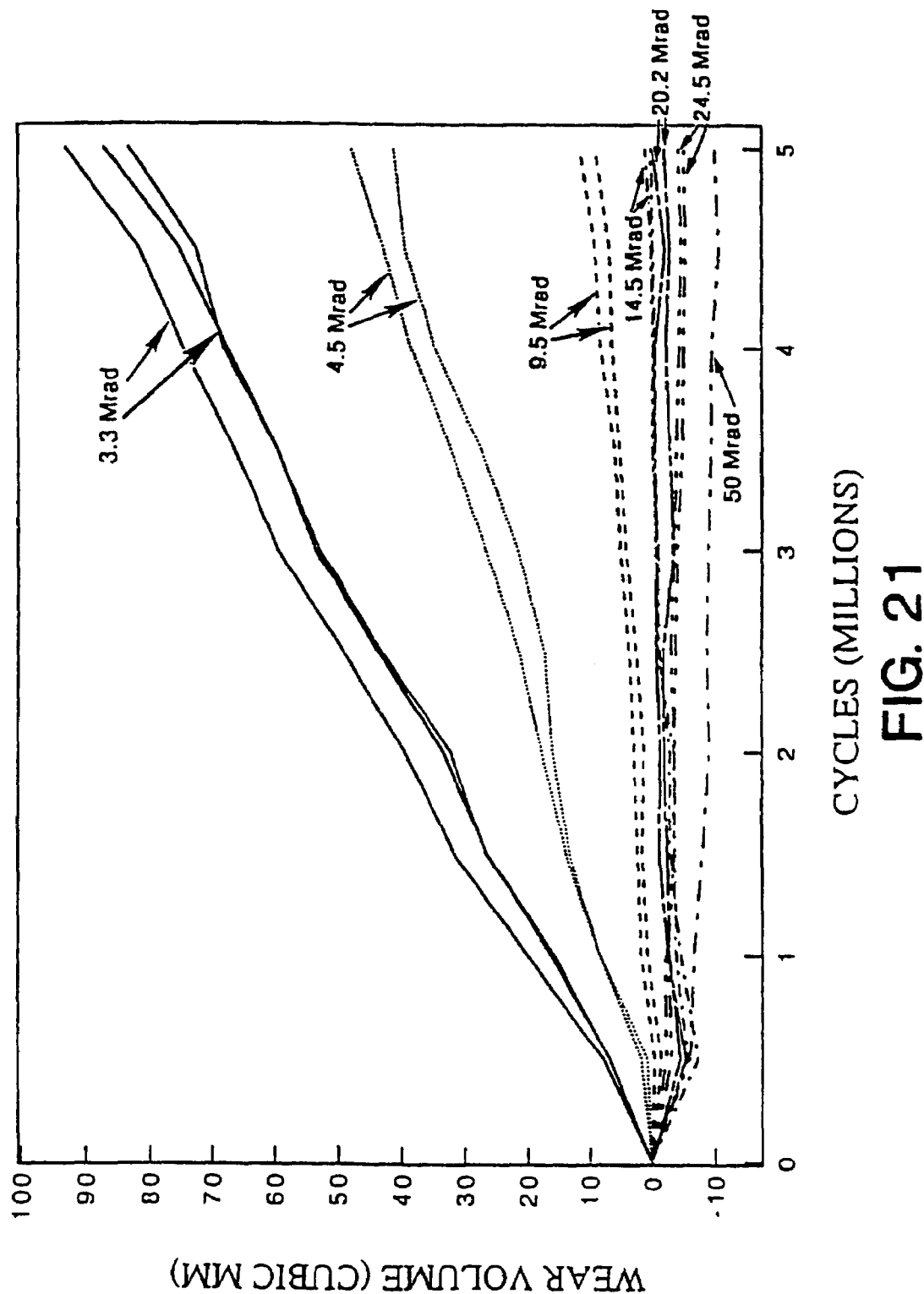
FIG. 21 shows the individual wear for cups irradiated at different doses.

FIG. 21 shows the soak-corrected wear (volume loss) of each material (three cups for 3.3 Mrad from EXAMPLE 2, two cups each for radiation dose from 4.5 to 24.5 Mrad, and one cup each for 50 and 100 Mrad). The individual wear rates, determined by linear regression, and the mean values for each type of material are listed in Table 5. At about 2.1 million cycles, there was a temporary overloading of the test cups, due to a malfunction of the computer controller. Although this overload had only a minor effect on the wear rates of the cups, the cup irradiated to 100 Mrad cracked and was, therefore, removed from the test.

FIG. 22 shows the average wear rate (volume loss from 1 to 5 million) of each type of material, that had been remelted (denoted in the figure by darkened circles) and that had not been re-melted (denoted in the figure by an open circle), as a function of dose.

The wear of the cups subjected to 3.3 or 4.5 Mrad with remelting averaged 17.5 or 9.3 $mm^3$ per million cycles, respectively, showing about 13% or 54% lower wear than for the 3.3 Mrad non-remelted cups (20.1 $mm^3$ per million cycles). In contrast, the wear rate of the 9.5 Mrad remelted cups averaged 2.2 $mm^3$ per million cycles, i.e., about 89% lower than for the 3.3 Mrad non-remelted cups. For radiation doses greater than 9.5 Mrad, minimal systematic wear occurred, such that, compared to that with 3.3 Mrad non-remelted cups, the wear rates were about 94% lower for the 14.5 Mrad remelted cups, and minimal wear (>99% reduction) for the 20.2 Mrad remelted cups.

"Negative" wear rates were calculated for the cups given 24 Mrad or greater doses. Apparently, these cups absorbed more water than the soak control cups, and the error between the two was greater than the weight loss due to wear, giving a net gain in weight.

Discussion

The results clearly demonstrated that the wear resistance of UHMWPE acetabular cups were improved substantially with increasing radiation dose over the range of 4.5 to 9.5 Mrad (i.e., with increasing crosslinking), such that wear was too small to accurately quantify for doses exceeding about 20 Mrad. Since, in addition to improving wear resistance, radiation induced crosslinking may degrade other physical properties, such as elongation to failure and fatigue strength, the dose-response curve developed in the present example provides the opportunity to select an optimum dose, i.e., one that provides the desired amount of improvement in wear resistance with a minimum reduction in other physical properties. The procedure for arriving at the choice of dose for a particular in vivo application is described in this application.

UHMWPE acetabular cups that had been compression molded and then exposed to 3.1 Mrad gamma radiation in air but were not thermally treated (i.e., typical of commercially used implants over the past two decades), showed an approximate wear rate of 33.1 $mm^3$/million cycle using the procedure of the wear test described in EXAMPLE 2, above. When compared to these conventional UHMWPE acetabular cups, the acetabular cups of the present invention (i.e., irradiated bar stock, remelted and machined into cups) show the following percentage reduction in wear rate: for the 3.3 Mrad remelted acetabular cup from EXAMPLE 2, above (about 47% reduction in wear rate); 4.5 Mrad remelted acetabular cup from EXAMPLE 5, above (about 72% reduction in wear rate); 9.5 Mrad remelted acetabular cup from EXAMPLE 5, above (about 93% reduction in wear rate).

Example 6

Physical Characterization of Gamma-Irradiated UHMWPE With or Without Remelting

Materials and Methods

The materials for physical characterization were the same as the wear tested materials described in EXAMPLE 5. The materials included UHMWPE extruded bars (3" in diameter) gamma irradiated to 3.3, 4.5, 9.5, 14.5, 20.2, 24, 50 and 100 Mrad, with or without remelting, and the non-irradiated bars. 8 mm thick disks were cut out of irradiated bars with or without remelting, and sterilized with ethylene oxide. The specimens for DSC and swelling measurements were cut out of the center of the 8 mm thick disks. The DSC measurement for crystallinity and melting temperature with sample weighing about 4 mg was described in EXAMPLE 1. For swelling measurements, 1 mm thick sheet weighing about 0.5 gram was cut out of the center of the 8 mm thick disk, and extraction of the sol-fraction was performed in boiling p-xylene for 72 hours, with 0.5 wt % antioxidant (2,6-di-t-butyl-4-methyl phenol) being added to prevent oxidation. After extraction, the gel was transferred to fresh p-xylene and allowed to equilibrate at 120° C. for 2 hours. The swollen gel was then quickly transferred to a weighing bottle, covered and weighed. The data was obtained as the average of five measurements. After measurements, samples were deswollen in acetone and then dried at 60° C. in a vacuum oven to a constant weight. The gel fraction was determined as the ratio of the weight of the dried extracted to the initial dry non-extracted network. The degree of swelling was calculated as the ratio of the weight of the swollen gel to the dried extracted gel. The degree of swelling was used to calculate the network chain density, number-average molecular weight between crosslinks and crosslink density, according to the theory of Flory and Rehner {Shen et al., *J. Polym. Sci. Polym. Phys.*, 34:1063-1077 (1996)}. For examining the oxidation profiles of the extruded bars irradiated and remelted in air, a two hundred micron thick section was microtomed perpendicular to the bar surface and examined by FTIR as a function of depth from the bar surface.

Results and Discussion

The melting temperature and crystallinity for non-irradiated, and irradiated (with and without remelting) materials are shown in Table 6. The degree of swelling, average molecular weight between crosslinks, crosslink density and gel content are shown in Table 7. After irradiation, the melting temperature and crystallinity increased, ranging from 135.3 to 140.2° C., and about 60 to 71%, respectively, over the dose range studied. Remelting of the irradiated bars resulted in reductions in the melting temperature and crystallinity, ranging from about 131 to 135° C., and about 51 to 53%, respectively.

As shown in Table 7, with increasing radiation dose, the degree of swelling and average molecular weight between crosslinks decreased, while the crosslink density increased. The gel content, in general, increased with radiation dose, but reached a plateau region at about 9.5 Mrad. With remelting, the degree of swelling and average molecular weight between crosslinks for bars irradiated up to 9.5 Mrad were significantly reduced, but remained almost unchanged after 9.5 Mrad. The crosslink density increased, after remelting, with dose up to 9.5 Mrad and then remained almost unchanged. The gel content, generally, increased after remelting.

The oxidation profiles for the 9.5 and 24 Mrad materials, after remelting at 150° C. in air for 5 hours, as a function of depth from the bar surface are shown in FIG. 24. The results clearly showed that the oxidation drops tremendously within 1 mm, and the most oxidized layer is about 1 mm deep below the surface, after irradiation and remelting in air.

Example 7

Tensile Properties of Gamma-Irradiated UHMWPE at Various Doses, With or Without Remelting Materials and Methods The materials for tensile test are the same as the wear tested materials described in EXAMPLE 5, above. The materials included UHMWPE extruded bars (3" in diameter) gamma irradiated to 4.5, 9.5, 14.5, 20.2, and 24 Mrad, with or without remelting, and non-irradiated bars. Five tensile specimens each was machined out of the center of the 3" diameter bars according to ASTM F648-96 and D-638 (type IV). Tensile tests were performed using an servo-hydraulic tensile test machine at speed of 2 inches/min.

Results and Discussion

Figure 27:
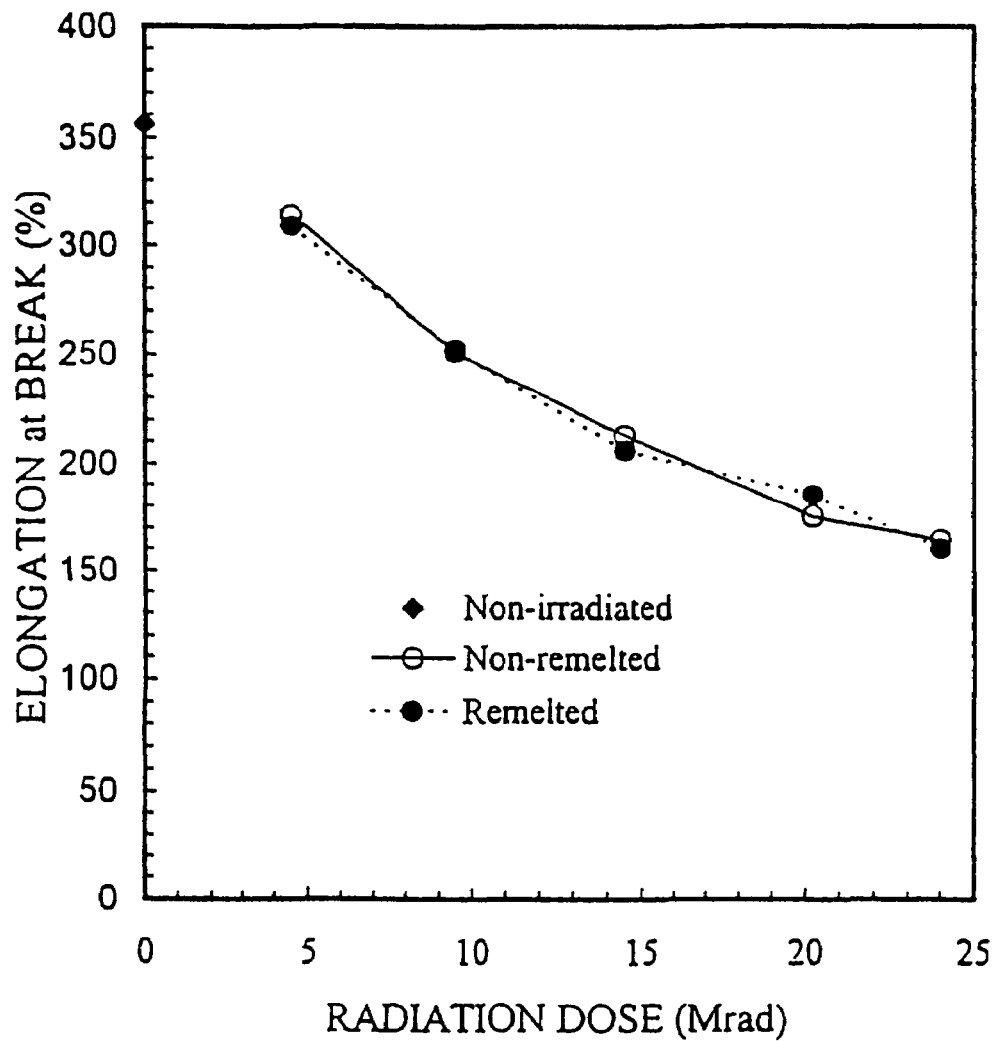
FIG. 27 graphically shows the elongation at break versus radiation dose of irradiated UHMWPE with or without remelting, and non-irradiated and not remelted UHMWPE.

The tensile strength at yield, elongation, and tensile strength (ultimate) at breaks are shown in Table 8. The average tensile properties as a function of radiation dose are shown in FIGS. 25-27. The tensile strength at yield after irradiation was higher than that of non-irradiated material, and slightly increased with radiation dose. Remelting of the irradiated bars resulted in a reduction in tensile strength at yield, and the strength remained almost constant over the dose range studied (FIG. 25). The tensile strength (ultimate) and elongation at break decreased with increasing doses (FIGS. 26-27). Remelting resulted in further reduction in ultimate tensile strength over the dose range. However, remelting had almost no effect on the elongation at break over the same dose range.

All publications and patent applications mentioned in so this Specification are herein incorporated by reference to the same extent as if each of them had been individually indicated to be incorporated by reference.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allows for obvious changes in the basic invention herein are also within the claims.

TABLE 1

3.3 Mrad

| | Before remelting | | | After remelting | | |
|---|---|---|---|---|---|---|
| Distance from surface (mm) | peak melting temperature (° C.) | degree of crystallinity (%) | gel content (%) | peak melting temperature (° C.) | degree of crystallinity (%) | gel content (%) |
| 34.8-35 | 135.3 | 59.6 | 91 | 131.4 | 52.5 | 94.7 |
| 35.8-36 | 135.4 | 60.2 | 91 | 131.5 | 51.2 | 94.7 |
| 36.8-37 | 135.3 | 60.5 | 91 | 131.4 | 51.9 | 94.7 |
| 37.8-38 (center) | 135.3 | 60 | 91.1 | 131.3 | 52 | 95 |

TABLE 2

28 Mrad

| | Before remelting | | | After remelting | | |
|---|---|---|---|---|---|---|
| Distance from surface (mm) | peak melting temperature (° C.) | degree of crystallinity (%) | gel content (%) | peak melting temperature (° C.) | degree of crystallinity (%) | gel content (%) |
| 34.8-35 | 139.8 | 65.1 | 95.8 | 135 | 52 | 97.7 |
| 35.8-36 | 139.8 | 64.2 | 95.8 | 134.8 | 52.1 | 97.7 |
| 36.8-37 | 139.7 | 64.5 | 95.8 | 134.9 | 52.5 | 97.7 |
| 37.8-38 (center) | 139.7 | 65.3 | 95.8 | 134.9 | 52.7 | 97.7 |

TABLE 3

| Cup # | Material | Wear Rate ($mm^3$/million cycles) | Mean Wear Rate ± Std Deviation |
|---|---|---|---|
| N11 | 3.3 Mrad Not remelted | 20.8 | 21.1 ± 0.3 |
| N16 | | 21.2 | |
| N17 | | 21.4 | |
| R21 | 3.3 Mrad Remelted | 17.7 | 18.6 ± 1.3 |
| R26 | | 20.1 | |
| R27 | | 18.0 | |
| N35 | 28 Mrad Not remelted | 0.29 | 0.25 ± 0.03 |
| N31 | | 0.24 | |
| N32 | | 0.24 | |
| R48 | 28 Mrad Remelted | 0.36 | 0.36 ± 0.001 |
| R45 | | 0.35 | |
| R49 | | 0.36 | |

TABLE 4

| Cup # | Material | 0-3 Million Cycles (non-aged) | | Conditions | 3-7 Million Cycles | |
|---|---|---|---|---|---|---|
| | | Wear Rate (mm³/million cycles) | Mean Wear Rate ± Std Deviation | | Wear Rate (mm³/million cycles) | Mean Wear Rate ± Std Deviation |
| N11 | 3.3 Mrad | 20.8 | 21.1 ± 0.3 | non-aged | 21.2 | — |
| N16 | Not | 21.2 | | aged | 21.5 | 21.8 ± 0.5 |
| N17 | remelted | 21.4 | | aged | 22.2 | |
| R21 | 3.3 Mrad | 17.7 | 18.6 ± 1.3 | non-aged | 17.5 | — |
| R26 | Remelted | 20.1 | | aged | 19.2 | 19.8 ± 1.0 |
| R27 | | 18.0 | | aged | 20.5 | |
| N35 | 28 Mrad | 0.29 | 0.25 ± 0.03 | non-aged | 0.03 | — |
| N31 | Not | 0.24 | | aged | −0.47 | −0.71 ± 0.3 |
| N32 | remelted | 0.24 | | aged | −0.93 | |
| R48 | 28 Mrad | 0.36 | 0.36 ± 0.001 | non-aged | 0.47 | — |
| R45 | Remelted | 0.35 | | aged | 0.08 | −0.06 ± 0.2 |
| R49 | | 0.36 | | aged | −0.20 | |

TABLE 5

(1-5 million cycles)

| Cup # | Material | Wear Rate (mm³/million cycles) | Mean Wear Rate ± SD (mm³/million cycles) |
|---|---|---|---|
| N11 | 3.3 Mrad Not remelted | 20.46 | 20.12 ± 0.7* |
| N16 | | 19.32 | |
| N17 | | 20.59 | |
| R21 | 3.3 Mrad Remelted | 17.04 | 17.51 ± 0.48* |
| R26 | | 18.0 | |
| R27 | | 17.49 | |
| RA2 | 4.5 Mrad Remelted | 9.93 | 9.28 ± 0.92 |
| RA3 | | 8.63 | |
| RB3 | 9.5 Mrad Remelted | 2.39 | 2.22 ± 0.24 |
| RB6 | | 2.05 | |
| RC5 | 14.5 Mrad Remelted | 1.26 | 1.17 ± 0.13 |
| RC6 | | 1.08 | |
| RD1 | 20.2 Mrad Remelted | 0.26 | 0.12 ± 0.2 |
| RD6 | | −0.02 | |
| RE3 | 24 Mrad Remelted | −0.49 | −0.59 ± 0.13 |
| RE4 | | −0.68 | |
| RF2 | 50 Mrad Remelted | −0.8 | — |
| RG1 | 100 Mrad Remelted | −6.88** | — |

*The wear data of the 3.3 Mrad materials in Example 2.
**The wear rate in the period of 1-2 million cycles.

TABLE 6

| Samples | Non-remelted | | Remelted | |
|---|---|---|---|---|
| | Melting point (° C.) | Crystallinity (%) | Melting point (° C.) | Crystallinity (%) |
| Non-irrad. | 133.8 | 55 | — | — |
| 3.3 Mrad | 135.3 ± 0.1 | 60.1 ± 0.4 | 131.4 ± 0.1 | 51.8 ± 0.6 |
| 4.5 Mrad | 136.2 ± 0.2 | 65.8 ± 1.6 | 131.6 ± 0.2 | 52.0 ± 1.3 |
| 9.5 Mrad | 137.1 ± 0 | 67.1 ± 2.2 | 134.8 ± 0.2 | 53.3 ± 2.1 |
| 14.5 Mrad | 137.5 ± 0.2 | 69.6 ± 1.6 | 135.0 ± 0.1 | 53.0 ± 1.5 |
| 20.2 Mrad | 137.4 ± 0.1 | 70.8 ± 2.8 | 135.3 ± 0.1 | 52.1 ± 1.8 |
| 24 Mrad | 137.9 ± 0.3 | 68.0 ± 1.3 | 135.2 ± 0.1 | 51.7 ± 1.2 |
| 50 Mrad | 138.9 ± 0.2 | 67.0 ± 1.3 | 135.2 ± 0 | 52.8 ± 0.2 |
| 100 Mrad | 140.2 ± 0.3 | 66.3 ± 2.7 | 130.8 ± 0.2 | 52.3 ± 1.7 |

TABLE 7

| Samples | Non-remelted | | | | Remelted | | | |
|---|---|---|---|---|---|---|---|---|
| | Degree of swelling | M.W. between crosslinks (g/mol) | Crosslink density (mol %) | Gel content (%) | Degree of swelling | M.W. between crosslinks (g/mol) | Crosslink density (mol %) | Gel content (%) |
| 3.3 Mrad | 5.29 | 8400 | 0.17 | 94.7 | 3.21 | 2500 | 0.56 | 98.1 |
| 4.5 Mrad | 3.57 | 3500 | 0.40 | 97.8 | 3.15 | 2400 | 0.58 | 98.4 |
| 9.5 Mrad | 2.82 | 1900 | 0.74 | 98.6 | 2.54 | 1400 | 1.0 | 98.9 |
| 14.5 Mrad | 2.35 | 1100 | 1.27 | 98.7 | 2.36 | 1100 | 1.27 | 99.2 |
| 20.2 Mrad | 2.27 | 1000 | 1.40 | 98.8 | 2.25 | 1000 | 1.40 | 99.2 |
| 24 Mrad | 2.17 | 900 | 1.56 | 98.7 | 2.24 | 1000 | 1.40 | 99.2 |
| 50 Mrad | 1.92 | 600 | 2.33 | 98.7 | 2.17 | 900 | 1.56 | 99.1 |
| 100 Mrad | 1.71 | 400 | 3.50 | 98.6 | 1.71 | 400 | 3.50 | 98.5 |

TABLE 8

| Materials | Tensile Strength at Yield (MPa) | Tensile Strength at Break (MPa) | Elongation at Break (%) |
|---|---|---|---|
| Non-irradiated | 23.3 ± 0.11 | 52.1 ± 4.78 | 356 ± 23 |
| Without remelting | | | |
| 4.5 Mrad | 24.9 ± 0.33 | 46.9 ± 2.91 | 314 ± 12 |
| 9.5 Mrad | 25.3 ± 0.12 | 47.6 ± 2.76 | 251 ± 8 |
| 14.5 Mrad | 25.7 ± 0.25 | 46.4 ± 1.20 | 213 ± 5 |
| 20.2 Mrad | 26.2 ± 0.27 | 40.2 ± 2.72 | 175 ± 7 |
| 24 Mrad | 26.4 ± 0.23 | 40.0 ± 5.42 | 164 ± 17 |
| After remelting | | | |
| 4.5 Mrad | 21.5 ± 0.33 | 45.6 ± 8.89 | 309 ± 20 |
| 9.5 Mrad | 21.3 ± 0.60 | 43.2 ± 2.80 | 252 ± 8 |
| 14.5 Mrad | 21.8 ± 0.29 | 36.8 ± 1.72 | 206 ± 9 |
| 20.2 Mrad | 21.9 ± 0.18 | 34.3 ± 3.61 | 185 ± 8 |
| 24 Mrad | 21.7 ± 0.25 | 32.3 ± 2.81 | 160 ± 19 |

We claim:

1. An implantable bearing component made by the process comprising the steps of:
   (a) crosslinking, by irradiation, a preformed polymer without melting or annealing it;
   (b) subsequently melting the irradiation crosslinked polymer without compression deforming the polymer, and then cooling the melted irradiation crosslinked polymer; and
   (c) fashioning the implantable bearing component from the crosslinked, melted and then cooled polymer, wherein the polymer is selected from the group consisting of: ultra high molecular weight polyethylene (UHMWPE) and high molecular weight polyethylene (HMWPE); and wherein said implantable bearing component possesses a gel content of between about 95% and about 99%.

2. The implantable bearing component of claim 1, wherein the polymer is crosslinked by gamma radiation at a dose of from about 1 to about 100 Mrad.

3. The implantable bearing component of claim 2, wherein the gamma radiation dose is from about 4 to about 15 Mrad.

4. The implantable bearing component of claim 3, wherein the gamma radiation dose is from about 4.5 to about 10 Mrad.

5. The implantable bearing component of claim 3, wherein the implantable bearing component is for use in a joint prosthesis.

6. The implantable bearing component of claim 5, wherein the joint prosthesis is selected from the group consisting of: hip, knee, ankle, elbow, jaw, shoulder, finger and spine joint prostheses.

7. The implantable bearing component of claim 6, wherein the joint prosthesis is selected from the group consisting of: hip and knee joint prostheses.

8. The implantable bearing component of claim 3, wherein the implantable bearing component is selected from the group consisting of: an acetabular cup and a liner of an acetabular cup.

9. A joint prosthesis comprising:
   a first member that can be secured to a first bone constituting a first portion of a joint;
   an articulating surface on the first member;
   a second member that can be secured to a second bone constituting a second portion of the joint; and
   the implantable bearing component of claim 3, said implantable bearing component can be disposed between the second member and the articulating surface, said implantable bearing component can receive said articulating surface for movement therein.

10. The joint prosthesis of claim 9, wherein the joint prosthesis is selected from the group consisting of: hip, knee, ankle, elbow, jaw, shoulder, finger and spine joint prostheses.

11. The joint prosthesis of claim 10, wherein the joint prosthesis is selected from the group consisting of: hip and knee joint prostheses.

12. The joint prosthesis of claim 9, wherein the joint prosthesis is for use in a hip joint replacement wherein:
   (a) the first bone is a femur;
   (b) the second bone is a pelvic bone;
   (c) the first member is a prosthetic stem;
   (d) the second member is a prosthetic acetabular shell;
   (e) the articulating surface is a prosthetic femoral ball; and
   (f) the implantable bearing component is an acetabular cup liner.

13. The joint prosthesis of claim 9, wherein said articulating surface and said first member are separate units.

14. A joint prosthesis comprising:
   a first member that can be secured to a first bone constituting a first portion of the joint;
   an articulating surface on the first member;
   the implantable bearing component of claim 3 that can be secured to a second bone constituting a second portion of the joint, said implantable bearing component can receive said articulating surface for movement therein.

15. The joint prosthesis of claim 14, wherein the joint prosthesis is selected from the group consisting of: hip, knee, ankle, elbow, jaw, shoulder, finger and spine joint prostheses.

16. The joint prosthesis of claim 15, wherein the joint prosthesis is selected from the group consisting of: hip and knee joint prostheses.

17. The joint prosthesis of claim 14, wherein the joint prosthesis is for use in a hip joint replacement wherein:
   (a) the first bone is a femur;
   (b) the second bone is a pelvic bone;
   (c) the first member is a prosthetic stem;
   (d) the implantable bearing component is a prosthetic acetabular cup; and
   (e) the articulating surface is a prosthetic femoral ball.

18. The joint prosthesis of claim 14, wherein said articulating surface and said first member are separate units.

19. The joint prosthesis of claim 12, wherein said prosthetic femoral ball and said prosthetic stem are separate units.

20. The joint prosthesis of claim 17, wherein said prosthetic femoral ball and said prosthetic stem are separate units.

21. The implantable bearing component of claim 1, wherein the implantable bearing component is for use in a joint prosthesis.

22. The implantable bearing component of claim 21, wherein the joint prosthesis is selected from the group consisting of: hip, knee, ankle, elbow, jaw, shoulder, finger and spine joint prostheses.

23. The implantable bearing component of claim 22, wherein the joint prosthesis is selected from the group consisting of: hip and knee joint prostheses.

24. The implantable bearing component of claim 3, wherein the implantable bearing component is selected from the group consisting of: an acetabular cup, and a liner of an acetabular cup.

25. The implantable bearing component of claim 3, wherein the polymer is crosslinked by radiation selected from the group consisting of: gamma radiation, electron beam radiation, and photon radiation.

26. The implantable bearing component of claim 3, wherein the preformed polymer is in the form of a polyethylene bar or polyethylene block.

27. A method for making an implant comprising the steps of:
   (a) crosslinking, by irradiation, a preformed polymer without melting or annealing it;
   (b) subsequently melting the irradiation crosslinked polymer without compression deforming the polymer, and then cooling the melted irradiation crosslinked polymer; and
   (c) removing an outer most oxidized layer of the crosslinked, melted and then cooled polymer, before or during fashioning the polymer into the implant; wherein the implant is an implantable bearing component having a bearing surface and the polymer is polyethylene.

28. The method of claim 27, wherein the polymer is selected from the group consisting of ultra high molecular weight polyethylene (UHMWPE) and high molecular weight polyethylene (HMWPE).

29. The method of claim 28, wherein the outer layer is removed by machining the surface of the crosslinked, melted and then cooled polymer before or during fashioning the implant from the remaining crosslinked, melted and then cooled polymer.

30. The method of claim 28, wherein the bearing surface of the implant possesses a gel content of between about 95% and about 99%.

31. The method of claim 29, wherein the bearing surface of the implant possesses a gel content of between about 95% and about 99%.

32. The implant made according to the method of claim 27.

33. The implant made according to the method of claim 28.

34. The implant made according to the method of claim 31.

35. A joint prosthesis comprising the implant of claim 33 and an articulating surface, the implant receives said articulating surface for movement within the implant.

* * * * *